US010292710B2

(12) United States Patent
Clark, III et al.

(10) Patent No.: US 10,292,710 B2
(45) Date of Patent: May 21, 2019

(54) DEVICES AND METHODS FOR LEFT ATRIAL APPENDAGE CLOSURE

(71) Applicant: SentreHEART, Inc., Redwood City, CA (US)

(72) Inventors: Robert L. Clark, III, Hayward, CA (US); Alan L. Bradley, San Francisco, CA (US); Gregory W. Fung, Redwood Shores, CA (US)

(73) Assignee: SentreHEART, Inc., Redwood City, CA (US)

( * ) Notice: Subject to any disclaimer, the term of this patent is extended or adjusted under 35 U.S.C. 154(b) by 260 days.

(21) Appl. No.: 15/442,216

(22) Filed: Feb. 24, 2017

(65) Prior Publication Data
US 2017/0245861 A1   Aug. 31, 2017

Related U.S. Application Data

(60) Provisional application No. 62/300,608, filed on Feb. 26, 2016.

(51) Int. Cl.
*A61B 17/04* (2006.01)
*A61B 17/12* (2006.01)
(Continued)

(52) U.S. Cl.
CPC .... *A61B 17/12013* (2013.01); *A61B 17/0483* (2013.01); *A61B 17/221* (2013.01);
(Continued)

(58) Field of Classification Search
CPC ............ A61B 17/221; A61B 17/32056; A61B 17/0483; A61B 17/12013;
(Continued)

(56) References Cited

U.S. PATENT DOCUMENTS 3,496,932 A    2/1970  Prisk et al.
3,677,597 A    7/1972  Stipek
(Continued)

FOREIGN PATENT DOCUMENTS

CN    101242785 A    8/2008
CN    101262823 B    12/2011
(Continued)

OTHER PUBLICATIONS afibfacts.com (Date Unknown). "Cox-Maze III: The Gold Standard Treatment for Atrial Fibrillation: Developing a Surgical Option for Atrial Fibrillation," located at <http://www.afibfacts.com/Treatment_Options_for_Atrial_Fibrillation/Cox-Maze_III%_3a_The_Gold_Standard_Treatment_for_Atrial_Fibrillation >, last visited on Apr. 20, 2007, 4 pages.
(Continued)

*Primary Examiner* — Julian W Woo
(74) *Attorney, Agent, or Firm* — Cooley LLP

(57) ABSTRACT

Closure devices and methods are provided for ligating tissue, such as the left atrial appendage. Generally, the closure devices include an elongate body, a snare loop assembly comprising a snare and a suture loop, and a shuttle connected to the snare and releasably coupled to the elongate body and retractable therein. In some variations, the shuttle may be configured to fit into the lumen. In other variations, a handle may be attached to the elongate body, and the handle may comprise a track and a snare control coupled to the track. The handle may be configured to release the shuttle from the elongate body and allow movement of the snare control along the track to retract the snare loop and the shuttle into a lumen of the elongate body.

21 Claims, 35 Drawing Sheets

(51) Int. Cl.
  *A61B 17/3205* (2006.01)
  *A61B 17/221* (2006.01)
  *A61B 90/00* (2016.01)

(52) U.S. Cl.
  CPC .... *A61B 17/32056* (2013.01); *A61B 17/0482* (2013.01); *A61B 2017/0475* (2013.01); *A61B 2017/0496* (2013.01); *A61B 2017/2212* (2013.01); *A61B 2090/034* (2016.02)

(58) Field of Classification Search
  CPC ...... A61B 2017/2212; A61B 2090/034; A61B 2017/0475; A61B 17/0482; A61B 2017/0496
  See application file for complete search history.

(56) References Cited

U.S. PATENT DOCUMENTS

| | | |
|---|---|---|
| 3,802,074 A | 4/1974 | Hoppe |
| 3,841,685 A | 10/1974 | Kolodziej |
| 3,999,555 A | 12/1976 | Person |
| 4,018,229 A | 4/1977 | Komiya |
| 4,030,509 A | 6/1977 | Heilman et al. |
| 4,078,305 A | 3/1978 | Akiyama |
| 4,181,123 A | 1/1980 | Crosby |
| 4,249,536 A | 2/1981 | Vega |
| 4,257,278 A | 3/1981 | Papadofrangakis et al. |
| 4,319,562 A | 3/1982 | Crosby |
| 4,428,375 A | 1/1984 | Ellman |
| 4,596,530 A | 6/1986 | McGlinn |
| 4,662,377 A | 5/1987 | Heilman et al. |
| 4,765,341 A | 8/1988 | Mower et al. |
| 4,817,608 A | 4/1989 | Shapland et al. |
| 4,901,405 A | 2/1990 | Grover et al. |
| 4,944,753 A | 7/1990 | Burgess et al. |
| 4,991,578 A | 2/1991 | Cohen |
| 4,991,603 A | 2/1991 | Cohen et al. |
| 4,998,975 A | 3/1991 | Cohen et al. |
| 5,033,477 A | 7/1991 | Chin et al. |
| 5,108,406 A | 4/1992 | Lee |
| 5,163,942 A | 11/1992 | Rydell |
| 5,163,946 A | 11/1992 | Li |
| 5,176,691 A | 1/1993 | Pierce |
| 5,181,123 A | 1/1993 | Swank |
| 5,181,919 A | 1/1993 | Bergman et al. |
| 5,226,535 A | 7/1993 | Roshdy et al. |
| 5,226,908 A | 7/1993 | Yoon |
| 5,242,459 A | 9/1993 | Buelna |
| 5,243,977 A | 9/1993 | Trabucco et al. |
| 5,269,326 A | 12/1993 | Verrier |
| 5,279,539 A | 1/1994 | Bohan et al. |
| 5,281,238 A | 1/1994 | Chin et al. |
| 5,300,078 A | 4/1994 | Buelna |
| 5,306,234 A | 4/1994 | Johnson |
| 5,318,578 A | 6/1994 | Hasson |
| 5,336,229 A | 8/1994 | Noda |
| 5,336,231 A | 8/1994 | Adair |
| 5,336,252 A | 8/1994 | Cohen |
| 5,385,156 A | 1/1995 | Oliva |
| 5,387,219 A | 2/1995 | Rappe |
| 5,398,944 A | 3/1995 | Holster |
| 5,403,331 A | 4/1995 | Chesterfield et al. |
| 5,405,351 A | 4/1995 | Kinet et al. |
| 5,417,684 A | 5/1995 | Jackson et al. |
| 5,423,821 A | 6/1995 | Pasque |
| 5,423,830 A | 6/1995 | Schneebaum et al. |
| 5,433,457 A | 7/1995 | Wright |
| 5,433,730 A | 7/1995 | Alt |
| 5,443,481 A | 8/1995 | Lee |
| 5,449,361 A | 9/1995 | Preissman |
| 5,449,637 A | 9/1995 | Kadry |
| 5,465,731 A | 11/1995 | Bell et al. |
| 5,494,240 A | 2/1996 | Waugh |
| 5,498,228 A | 3/1996 | Royalty et al. |
| 5,540,711 A | 7/1996 | Kieturakis et al. |
| 5,545,178 A | 8/1996 | Kensey et al. |
| 5,571,161 A | 11/1996 | Starksen |
| 5,591,177 A | 1/1997 | Lehrer |
| 5,609,597 A | 3/1997 | Lehrer |
| 5,624,430 A | 4/1997 | Eton et al. |
| 5,624,453 A | 4/1997 | Ahmed |
| 5,634,895 A | 6/1997 | Igo et al. |
| 5,636,780 A | 6/1997 | Green et al. |
| 5,676,162 A | 10/1997 | Larson, Jr. et al. |
| 5,676,651 A | 10/1997 | Larson, Jr. et al. |
| 5,678,547 A | 10/1997 | Faupel et al. |
| 5,681,278 A | 10/1997 | Igo et al. |
| 5,682,906 A | 11/1997 | Sterman et al. |
| 5,683,348 A | 11/1997 | Diener |
| 5,683,364 A | 11/1997 | Zadini et al. |
| 5,683,445 A | 11/1997 | Swoyer |
| 5,693,059 A | 12/1997 | Yoon |
| 5,693,091 A | 12/1997 | Larson, Jr. et al. |
| 5,699,748 A | 12/1997 | Linskey, Jr. et al. |
| 5,702,430 A | 12/1997 | Larson, Jr. et al. |
| 5,707,336 A | 1/1998 | Rubin |
| 5,716,367 A | 2/1998 | Koike et al. |
| 5,716,392 A | 2/1998 | Bourgeois et al. |
| 5,727,569 A | 3/1998 | Benetti et al. |
| 5,728,151 A | 3/1998 | Garrison et al. |
| 5,735,877 A | 4/1998 | Pagedas |
| 5,741,281 A | 4/1998 | Martin |
| 5,752,526 A | 5/1998 | Cosgrove |
| 5,766,151 A | 6/1998 | Valley et al. |
| 5,766,216 A | 6/1998 | Gangal et al. |
| 5,766,217 A | 6/1998 | Christy |
| 5,769,863 A | 6/1998 | Garrison |
| 5,779,727 A | 7/1998 | Orejola |
| 5,788,715 A | 8/1998 | Watson, Jr. et al. |
| 5,792,151 A | 8/1998 | Heck et al. |
| 5,797,870 A | 8/1998 | March et al. |
| 5,797,929 A | 8/1998 | Andreas et al. |
| 5,797,946 A | 8/1998 | Chin |
| 5,799,661 A | 9/1998 | Boyd et al. |
| 5,810,845 A | 9/1998 | Yoon |
| 5,814,052 A | 9/1998 | Nakao et al. |
| 5,823,946 A | 10/1998 | Chin |
| 5,827,216 A | 10/1998 | Igo et al. |
| 5,840,059 A | 11/1998 | March et al. |
| 5,855,586 A | 1/1999 | Habara et al. |
| 5,865,791 A | 2/1999 | Whayne et al. |
| 5,871,531 A | 2/1999 | Struble |
| 5,873,876 A | 2/1999 | Christy |
| 5,879,375 A | 3/1999 | Larson, Jr. et al. |
| 5,882,299 A | 3/1999 | Rastegar et al. |
| 5,893,869 A | 4/1999 | Barnhart et al. |
| 5,895,298 A | 4/1999 | Faupel et al. |
| 5,897,487 A * | 4/1999 | Ouchi ............... A61B 17/12013 600/127 |
| 5,897,586 A | 4/1999 | Molina |
| 5,900,433 A | 5/1999 | Igo et al. |
| 5,906,579 A | 5/1999 | Vander Salm et al. |
| 5,906,620 A | 5/1999 | Nakao et al. |
| 5,908,429 A | 6/1999 | Yoon |
| 5,908,435 A | 6/1999 | Samuels |
| 5,910,124 A | 6/1999 | Rubin |
| 5,910,129 A | 6/1999 | Koblish et al. |
| 5,921,994 A | 7/1999 | Andreas et al. |
| 5,924,424 A | 7/1999 | Stevens et al. |
| RE36,269 E | 8/1999 | Wright |
| 5,941,819 A | 8/1999 | Chin |
| 5,957,936 A | 9/1999 | Yoon et al. |
| 5,961,440 A | 10/1999 | Schweich, Jr. et al. |
| 5,964,699 A | 10/1999 | Rullo et al. |
| 5,968,010 A | 10/1999 | Waxman et al. |
| 5,972,013 A | 10/1999 | Schmidt |
| 5,984,866 A | 11/1999 | Rullo et al. |
| 5,984,917 A | 11/1999 | Fleischman et al. |
| 5,991,668 A | 11/1999 | Leinders et al. |
| 5,997,525 A | 12/1999 | March et al. |
| 6,006,122 A | 12/1999 | Smits |
| 6,010,531 A | 1/2000 | Donlon et al. |
| 6,015,382 A | 1/2000 | Zwart et al. |
| 6,045,570 A | 4/2000 | Epstein et al. |

(56) References Cited

U.S. PATENT DOCUMENTS

| | | | |
|---|---|---|---|
| 6,048,329 A | 4/2000 | Thompson et al. | |
| 6,059,750 A | 5/2000 | Fogarty et al. | |
| 6,067,942 A | 5/2000 | Fernandez | |
| 6,068,603 A * | 5/2000 | Suzuki | A61B 10/04 |
| | | | 600/564 |
| 6,071,281 A | 6/2000 | Burnside et al. | |
| 6,081,738 A | 6/2000 | Hinohara et al. | |
| 6,083,153 A | 7/2000 | Rullo et al. | |
| 6,090,042 A | 7/2000 | Rullo et al. | |
| 6,095,968 A | 8/2000 | Snyders | |
| 6,110,170 A | 8/2000 | Taylor et al. | |
| 6,120,431 A | 9/2000 | Magovern et al. | |
| 6,132,438 A | 10/2000 | Fleischman et al. | |
| 6,148,230 A | 11/2000 | KenKnight | |
| 6,149,595 A | 11/2000 | Seitz et al. | |
| 6,152,144 A | 11/2000 | Lesh et al. | |
| 6,152,920 A | 11/2000 | Thompson et al. | |
| 6,152,936 A | 11/2000 | Christy et al. | |
| 6,155,968 A | 12/2000 | Wilk | |
| 6,157,852 A | 12/2000 | Selmon et al. | |
| 6,161,543 A | 12/2000 | Cox et al. | |
| 6,162,195 A | 12/2000 | Igo et al. | |
| 6,167,889 B1 | 1/2001 | Benetti | |
| 6,199,556 B1 | 3/2001 | Benetti et al. | |
| 6,200,303 B1 | 3/2001 | Verrior et al. | |
| 6,206,004 B1 | 3/2001 | Schmidt et al. | |
| 6,224,584 B1 | 5/2001 | March et al. | |
| 6,231,518 B1 | 5/2001 | Grabek et al. | |
| 6,237,605 B1 | 5/2001 | Vaska et al. | |
| 6,241,667 B1 | 6/2001 | Vetter et al. | |
| 6,258,021 B1 | 7/2001 | Wilk | |
| 6,266,550 B1 | 7/2001 | Selmon et al. | |
| 6,280,415 B1 | 8/2001 | Johnson | |
| 6,283,127 B1 | 9/2001 | Sterman et al. | |
| 6,290,674 B1 | 9/2001 | Roue et al. | |
| 6,293,906 B1 | 9/2001 | Vanden Hoek et al. | |
| 6,296,630 B1 | 10/2001 | Altman et al. | |
| 6,311,692 B1 | 11/2001 | Vaska et al. | |
| 6,311,693 B1 | 11/2001 | Sterman et al. | |
| 6,314,962 B1 | 11/2001 | Vaska et al. | |
| 6,314,963 B1 | 11/2001 | Vaska et al. | |
| 6,319,201 B1 | 11/2001 | Wilk | |
| 6,333,347 B1 | 12/2001 | Hunter et al. | |
| 6,346,074 B1 | 2/2002 | Roth | |
| 6,379,366 B1 | 4/2002 | Fleischman et al. | |
| 6,423,051 B1 | 7/2002 | Kaplan et al. | |
| 6,474,340 B1 | 11/2002 | Vaska et al. | |
| 6,485,407 B2 | 11/2002 | Alferness et al. | |
| 6,488,689 B1 | 12/2002 | Kaplan et al. | |
| 6,494,211 B1 | 12/2002 | Boyd et al. | |
| 6,551,303 B1 | 4/2003 | Van Tassel et al. | |
| 6,561,969 B2 | 5/2003 | Frazier et al. | |
| 6,592,552 B1 | 7/2003 | Schmidt | |
| 6,610,055 B1 | 8/2003 | Swanson et al. | |
| 6,610,072 B1 | 8/2003 | Christy et al. | |
| 6,613,062 B1 | 9/2003 | Leckrone et al. | |
| 6,632,229 B1 | 10/2003 | Yamanouchi | |
| 6,652,555 B1 | 11/2003 | VanTassel et al. | |
| 6,656,175 B2 | 12/2003 | Francischelli et al. | |
| 6,666,861 B1 | 12/2003 | Grabek | |
| 6,692,491 B1 | 2/2004 | Phan | |
| 6,733,509 B2 | 5/2004 | Nobles et al. | |
| 6,736,774 B2 | 5/2004 | Benetti et al. | |
| 6,755,338 B2 | 6/2004 | Hahnen et al. | |
| 6,786,898 B2 | 9/2004 | Guenst | |
| 6,789,509 B1 | 9/2004 | Motsinger | |
| 6,830,174 B2 | 12/2004 | Hillstead et al. | |
| 6,830,576 B2 | 12/2004 | Fleischman et al. | |
| 6,985,776 B2 | 1/2006 | Kane et al. | |
| 7,011,671 B2 | 3/2006 | Welch | |
| 7,041,111 B2 | 5/2006 | Chu | |
| 7,056,294 B2 | 6/2006 | Khairkhahan et al. | |
| 7,063,682 B1 | 6/2006 | Whayne et al. | |
| 7,063,693 B2 | 6/2006 | Guenst | |
| 7,175,619 B2 | 2/2007 | Koblish et al. | |
| 7,186,214 B2 | 3/2007 | Ness | |
| 7,207,988 B2 | 4/2007 | Leckrone et al. | |
| 7,226,440 B2 | 6/2007 | Gelfand et al. | |
| 7,226,458 B2 | 6/2007 | Kaplan et al. | |
| 7,264,587 B2 | 9/2007 | Chin | |
| 7,294,115 B1 | 11/2007 | Wilk | |
| 7,297,144 B2 | 11/2007 | Fleischman et al. | |
| 7,309,328 B2 | 12/2007 | Kaplan et al. | |
| 7,318,829 B2 | 1/2008 | Kaplan et al. | |
| 7,326,221 B2 | 2/2008 | Sakamoto et al. | |
| 7,331,979 B2 | 2/2008 | Khosravi et al. | |
| 7,473,260 B2 | 1/2009 | Opolski et al. | |
| 7,507,200 B2 * | 3/2009 | Okada | A61B 1/012 |
| | | | 600/104 |
| 7,597,705 B2 | 10/2009 | Forsberg et al. | |
| 7,608,091 B2 | 10/2009 | Goldfarb et al. | |
| 7,610,104 B2 | 10/2009 | Kaplan et al. | |
| 7,618,425 B2 | 11/2009 | Yamamoto et al. | |
| 7,722,641 B2 | 5/2010 | van der Burg et al. | |
| 7,828,810 B2 | 11/2010 | Liddicoat et al. | |
| 7,846,168 B2 | 12/2010 | Liddicoat et al. | |
| 7,905,900 B2 | 3/2011 | Palermo et al. | |
| 7,918,865 B2 | 4/2011 | Liddicoat et al. | |
| 7,967,808 B2 | 6/2011 | Fitzgerald et al. | |
| 8,070,693 B2 | 12/2011 | Ayala et al. | |
| 8,105,342 B2 | 1/2012 | Onuki et al. | |
| 8,157,818 B2 | 4/2012 | Gartner et al. | |
| 8,287,561 B2 | 10/2012 | Nunez et al. | |
| 8,469,983 B2 | 6/2013 | Fung et al. | |
| 8,636,767 B2 | 1/2014 | McClain | |
| 8,715,302 B2 | 5/2014 | Ibrahim et al. | |
| 8,721,663 B2 | 5/2014 | Kaplan et al. | |
| 8,771,297 B2 | 7/2014 | Miller et al. | |
| 8,795,297 B2 | 8/2014 | Liddicoat et al. | |
| 8,795,310 B2 | 8/2014 | Fung et al. | |
| 8,814,778 B2 | 8/2014 | Kiser et al. | |
| 8,932,276 B1 | 1/2015 | Morriss et al. | |
| 8,961,543 B2 | 2/2015 | Friedman et al. | |
| 8,986,325 B2 | 3/2015 | Miller et al. | |
| 9,089,324 B2 | 7/2015 | McCaw et al. | |
| 9,186,174 B2 | 11/2015 | Krishnan et al. | |
| 9,198,664 B2 | 12/2015 | Fung et al. | |
| 9,198,683 B2 | 12/2015 | Friedman et al. | |
| 9,271,819 B2 | 3/2016 | Liddicoat et al. | |
| 9,339,295 B2 | 5/2016 | Fung et al. | |
| 9,408,608 B2 | 8/2016 | Clark et al. | |
| 10,045,784 B2 | 8/2018 | Friedman et al. | |
| 2001/0025132 A1 | 9/2001 | Alferness et al. | |
| 2002/0017306 A1 | 2/2002 | Cox et al. | |
| 2002/0022860 A1 | 2/2002 | Borillo et al. | |
| 2002/0049457 A1 | 4/2002 | Kaplan et al. | |
| 2002/0058925 A1 | 5/2002 | Kaplan et al. | |
| 2002/0062136 A1 | 5/2002 | Hillstead et al. | |
| 2002/0068970 A1 | 6/2002 | Cox et al. | |
| 2002/0099390 A1 | 7/2002 | Kaplan et al. | |
| 2002/0103492 A1 | 8/2002 | Kaplan et al. | |
| 2002/0107531 A1 | 8/2002 | Schreck et al. | |
| 2002/0111636 A1 | 8/2002 | Fleischman et al. | |
| 2002/0111637 A1 | 8/2002 | Kaplan et al. | |
| 2002/0147456 A1 | 10/2002 | Diduch et al. | |
| 2003/0014049 A1 | 1/2003 | Koblish et al. | |
| 2003/0024537 A1 | 2/2003 | Cox et al. | |
| 2003/0045900 A1 | 3/2003 | Hahnen et al. | |
| 2003/0069577 A1 | 4/2003 | Vaska et al. | |
| 2003/0083542 A1 | 5/2003 | Alferness et al. | |
| 2003/0083674 A1 | 5/2003 | Gibbens, III | |
| 2003/0109863 A1 | 6/2003 | Francischelli et al. | |
| 2003/0120264 A1 | 6/2003 | Lattouf | |
| 2003/0158464 A1 | 8/2003 | Bertolero | |
| 2003/0181942 A1 | 9/2003 | Sutton et al. | |
| 2003/0187460 A1 | 10/2003 | Chin et al. | |
| 2003/0236535 A1 | 12/2003 | Onuki et al. | |
| 2004/0030335 A1 | 2/2004 | Zenati et al. | |
| 2004/0034347 A1 | 2/2004 | Hall et al. | |
| 2004/0044361 A1 | 3/2004 | Frazier et al. | |
| 2004/0049210 A1 | 3/2004 | VanTassel et al. | |
| 2004/0059352 A1 | 3/2004 | Burbank et al. | |
| 2004/0064138 A1 | 4/2004 | Grabek | |
| 2004/0068267 A1 | 4/2004 | Harvie et al. | |

(56) References Cited

U.S. PATENT DOCUMENTS

| | | |
|---|---|---|
| 2004/0078069 A1 | 4/2004 | Francischelli et al. |
| 2004/0102804 A1 | 5/2004 | Chin |
| 2004/0106918 A1 | 6/2004 | Cox et al. |
| 2004/0111101 A1 | 6/2004 | Chin |
| 2004/0116943 A1 | 6/2004 | Brandt et al. |
| 2004/0158127 A1 | 8/2004 | Okada |
| 2004/0162579 A1 | 8/2004 | Foerster |
| 2004/0225212 A1 | 11/2004 | Okerlund et al. |
| 2004/0225300 A1 | 11/2004 | Goldfarb et al. |
| 2004/0243176 A1 | 12/2004 | Hahnen et al. |
| 2004/0260273 A1 | 12/2004 | Wan |
| 2005/0033280 A1 | 2/2005 | Francischelli et al. |
| 2005/0033287 A1 | 2/2005 | Sra |
| 2005/0033321 A1 | 2/2005 | Fleischman et al. |
| 2005/0043743 A1 | 2/2005 | Dennis |
| 2005/0043745 A1 | 2/2005 | Alferness et al. |
| 2005/0080454 A1 | 4/2005 | Drews et al. |
| 2005/0085843 A1 | 4/2005 | Opolski et al. |
| 2005/0107824 A1 | 5/2005 | Hillstead et al. |
| 2005/0149068 A1 | 7/2005 | Williams et al. |
| 2005/0149069 A1 | 7/2005 | Bertolero et al. |
| 2005/0154376 A1 | 7/2005 | Riviere et al. |
| 2005/0165466 A1 | 7/2005 | Morris et al. |
| 2005/0256532 A1 | 11/2005 | Nayak et al. |
| 2006/0004323 A1 | 1/2006 | Chang et al. |
| 2006/0004388 A1 | 1/2006 | Whayne et al. |
| 2006/0009715 A1 | 1/2006 | Khairkhahan et al. |
| 2006/0020162 A1 | 1/2006 | Whayne et al. |
| 2006/0020271 A1 | 1/2006 | Stewart et al. |
| 2006/0020336 A1 | 1/2006 | Liddicoat |
| 2006/0034930 A1 | 2/2006 | Khosravi et al. |
| 2006/0100545 A1 | 5/2006 | Ayala et al. |
| 2006/0200169 A1 | 9/2006 | Sniffin |
| 2006/0212045 A1 | 9/2006 | Schilling et al. |
| 2006/0247672 A1 | 11/2006 | Vidlund et al. |
| 2006/0253128 A1 | 11/2006 | Sekine et al. |
| 2007/0010829 A1 | 1/2007 | Nobles et al. |
| 2007/0016228 A1 | 1/2007 | Salas |
| 2007/0027456 A1 | 2/2007 | Gartner et al. |
| 2007/0038229 A1 | 2/2007 | de la Torre |
| 2007/0060951 A1 | 3/2007 | Shannon |
| 2007/0083082 A1 | 4/2007 | Kiser et al. |
| 2007/0083225 A1 | 4/2007 | Kiser et al. |
| 2007/0083232 A1 | 4/2007 | Lee |
| 2007/0088369 A1 | 4/2007 | Shaw et al. |
| 2007/0100405 A1 | 5/2007 | Thompson et al. |
| 2007/0135822 A1 | 6/2007 | Onuki et al. |
| 2007/0149988 A1 | 6/2007 | Michler et al. |
| 2007/0179345 A1 | 8/2007 | Santilli |
| 2007/0249991 A1 | 10/2007 | Whayne et al. |
| 2007/0260278 A1 | 11/2007 | Wheeler et al. |
| 2007/0270637 A1 | 11/2007 | Takemoto et al. |
| 2007/0270891 A1 | 11/2007 | McGuckin, Jr. |
| 2008/0009843 A1 | 1/2008 | de la Torre |
| 2008/0015406 A1 | 1/2008 | Dlugos et al. |
| 2008/0033241 A1 | 2/2008 | Peh et al. |
| 2008/0033457 A1 | 2/2008 | Francischelli et al. |
| 2008/0039879 A1 | 2/2008 | Chin et al. |
| 2008/0097489 A1 | 4/2008 | Goldfarb et al. |
| 2008/0154260 A1 | 6/2008 | Hoof |
| 2008/0228265 A1 | 9/2008 | Spence et al. |
| 2008/0245371 A1 | 10/2008 | Gruber |
| 2008/0269782 A1 | 10/2008 | Stefanchik et al. |
| 2008/0294174 A1 | 11/2008 | Bardsley et al. |
| 2008/0294175 A1 | 11/2008 | Bardsley et al. |
| 2008/0312664 A1 | 12/2008 | Bardsley et al. |
| 2009/0043317 A1 | 2/2009 | Cavanaugh et al. |
| 2009/0088778 A1 | 4/2009 | Miyamoto et al. |
| 2009/0157118 A1 | 6/2009 | Miller et al. |
| 2009/0182326 A1 | 7/2009 | Zenati et al. |
| 2009/0196696 A1 | 8/2009 | Otsuka et al. |
| 2010/0069925 A1 | 3/2010 | Friedman et al. |
| 2010/0094314 A1 | 4/2010 | Hernlund |
| 2010/0174296 A1* | 7/2010 | Vakharia ............. A61B 17/0487 606/144 |
| 2010/0191253 A1 | 7/2010 | Oostman et al. |
| 2010/0331820 A1 | 12/2010 | Giuseppe et al. |
| 2011/0060350 A1 | 3/2011 | Powers et al. |
| 2011/0087270 A1 | 4/2011 | Penner et al. |
| 2011/0092997 A1 | 4/2011 | Kang |
| 2011/0106107 A1 | 5/2011 | Binmoeller et al. |
| 2011/0112537 A1 | 5/2011 | Bernstein et al. |
| 2011/0144660 A1 | 6/2011 | Liddicoat et al. |
| 2011/0295060 A1 | 12/2011 | Zenati et al. |
| 2012/0022558 A1 | 1/2012 | Friedman et al. |
| 2012/0209300 A1 | 8/2012 | Torrie |
| 2012/0330351 A1 | 12/2012 | Friedman et al. |
| 2013/0144311 A1 | 6/2013 | Fung et al. |
| 2014/0018831 A1 | 1/2014 | Kassab et al. |
| 2014/0171733 A1 | 6/2014 | Sternik |
| 2014/0222138 A1 | 8/2014 | Machold et al. |
| 2014/0276911 A1 | 9/2014 | Smith et al. |
| 2014/0303721 A1 | 10/2014 | Fung et al. |
| 2014/0336572 A1 | 11/2014 | Heisel et al. |
| 2014/0336676 A1 | 11/2014 | Pong et al. |
| 2014/0364901 A1 | 12/2014 | Kiser et al. |
| 2014/0364907 A1 | 12/2014 | White et al. |
| 2015/0018853 A1 | 1/2015 | Friedman et al. |
| 2015/0025312 A1 | 1/2015 | de Canniere |
| 2015/0173765 A1 | 1/2015 | Friedman et al. |
| 2015/0119884 A1 | 4/2015 | Fung et al. |
| 2015/0157328 A1 | 6/2015 | Miller et al. |
| 2015/0182225 A1 | 7/2015 | Morejohn et al. |
| 2015/0190135 A1 | 7/2015 | Ibrahim et al. |
| 2015/0223813 A1 | 8/2015 | Williamson et al. |
| 2015/0250482 A1 | 9/2015 | Slaughter et al. |
| 2015/0272618 A1 | 10/2015 | Fung et al. |
| 2015/0374380 A1 | 12/2015 | Miller et al. |
| 2016/0008001 A1 | 1/2016 | Winkler et al. |
| 2016/0106421 A1 | 4/2016 | Eliachar et al. |
| 2016/0120549 A1 | 5/2016 | Fung et al. |
| 2016/0278781 A1 | 9/2016 | Fung et al. |
| 2016/0302793 A1 | 10/2016 | Fung et al. |
| 2016/0310144 A1 | 10/2016 | Kimura et al. |
| 2016/0310145 A1 | 10/2016 | Clark et al. |
| 2016/0317155 A1 | 11/2016 | Kimura et al. |
| 2016/0346028 A1 | 12/2016 | Rogers et al. |
| 2017/0100183 A1* | 4/2017 | Iaizzo ............... A61B 18/02 |
| 2018/0325523 A1 | 11/2018 | Friedman et al. |

FOREIGN PATENT DOCUMENTS

| | | |
|---|---|---|
| EP | 0 598 219 A2 | 5/1994 |
| EP | 0 598 219 A3 | 5/1994 |
| EP | 0 598 219 B1 | 5/1994 |
| EP | 0 625 336 A2 | 11/1994 |
| EP | 0 705 566 A1 | 4/1996 |
| EP | 1 010 397 A | 6/2000 |
| GB | 1 506 142 A | 4/1978 |
| JP | H-6-319742 A | 11/1994 |
| JP | 7-296645 A2 | 11/1995 |
| JP | 7-299073 A | 11/1995 |
| JP | 11-507262 A | 6/1999 |
| JP | 2001-120560 A | 5/2001 |
| JP | 2002-512071 A | 4/2002 |
| JP | 2002-540834 A | 12/2002 |
| JP | 2002-540901 A | 12/2002 |
| JP | 2003-225241 A | 8/2003 |
| JP | 2004-000601 A | 1/2004 |
| JP | 2005-110860 A | 4/2005 |
| JP | 2005-296645 A | 10/2005 |
| JP | 2005-531360 A | 10/2005 |
| JP | 2007-504886 A | 3/2007 |
| WO | WO-94/01045 A1 | 1/1994 |
| WO | WO-94/04079 A1 | 3/1994 |
| WO | WO-94/08514 A1 | 4/1994 |
| WO | WO-96/04854 A1 | 2/1996 |
| WO | WO-96/40356 A1 | 12/1996 |
| WO | WO-97/11644 A1 | 4/1997 |
| WO | WO-97/43957 A1 | 11/1997 |
| WO | WO-99/53845 A1 | 10/1999 |
| WO | WO-00/59383 A1 | 10/2000 |
| WO | WO-00/61202 A1 | 10/2000 |
| WO | WO-2004/002327 A1 | 1/2004 |

(56) References Cited

FOREIGN PATENT DOCUMENTS

| | | |
|---|---|---|
| WO | WO-2004/066828 A2 | 8/2004 |
| WO | WO-2004/066828 A3 | 8/2004 |
| WO | WO-2005/034767 A1 | 4/2005 |
| WO | WO-2005/034802 A2 | 4/2005 |
| WO | WO-2005/034802 A3 | 4/2005 |
| WO | WO-2006/096805 A1 | 9/2006 |
| WO | WO-2006/110734 A2 | 10/2006 |
| WO | WO-2006/110734 A3 | 10/2006 |
| WO | WO-2006/115689 A1 | 11/2006 |
| WO | WO-2007/001936 A2 | 1/2007 |
| WO | WO-2007/001936 A3 | 1/2007 |
| WO | WO-2007/037516 A2 | 4/2007 |
| WO | WO-2007/037516 A3 | 4/2007 |
| WO | WO-2007/056502 A1 | 5/2007 |
| WO | WO-2008/036408 A2 | 3/2008 |
| WO | WO-2008/036408 A3 | 3/2008 |
| WO | WO-2008/091612 A2 | 7/2008 |
| WO | WO-2008/091612 A3 | 7/2008 |
| WO | WO-2008/121278 A2 | 10/2008 |
| WO | WO-2008/121278 A3 | 10/2008 |
| WO | WO-2009/039191 A2 | 3/2009 |
| WO | WO-2009/039191 A3 | 3/2009 |
| WO | WO-2009/094237 A1 | 7/2009 |
| WO | WO-2010/006061 A2 | 1/2010 |
| WO | WO-2010/006061 A3 | 1/2010 |
| WO | WO-2010/048141 A2 | 4/2010 |
| WO | WO-2010/048141 A3 | 4/2010 |
| WO | WO-2010/115030 A1 | 10/2010 |
| WO | WO-2012/170652 A1 | 12/2012 |
| WO | WO-2014/164028 A1 | 10/2014 |

OTHER PUBLICATIONS

Al-Saady, N.M. et al. (1999). "Left Atrial Appendage: Structure, Function, and Role in Thromboembolism," *Heart* 82:547-554.

Albers, G.W. (Jul. 11, 1994). "Atrial Fibrillation and Stroke: Three New Studies, Three Remaining Questions," *Arch Intern Med* 154:1443-1448.

Alonso, M. et al. (Mar. 4, 2003). "Complications With Femoral Access in Cardiac Catheterization. Impact of Previous Systematic Femoral Angiography and Hemostasis With VasoSeal-Es® Collagen Plug," *Rev. Esp. Cardiol.* 56(6):569-577.

Aronow, W.S. et al. (Apr. 2009). "Atrial Fibrillation: The New Epidemic of the Age-ing World," *Journal of Atrial Fibrillation* 1(6):337-361.

Babaliaros, V.C. et al. (Jun. 3, 2008). "Emerging Applications for Transseptal Left Heart Catheterization: Old Techniques for New Procedures," *Journal of the American College of Cardiology* 51(22):2116-2122.

Bath, P.M.W. et al. (2005). "Current Status of Stroke Prevention in Patients with Atrial Fibrillation," *European Heart Journal Supplements* 7(Supplement C):C12-C18.

Benjamin, B.A. et al. (1994). "Effect of Bilateral Atrial Appendectomy on Postprandial Sodium Excretion in Conscious Monkeys," *Society for Experimental Biology and Medicine* 2006: 1 page.

Beygui, F. et al. (2005, e-pub. Oct. 21, 2005). "Multimodality Imaging of Percutaneous Closure of the Left Atrial Appendage," *Clinical Vignette*, 1 page.

Bisleri, G. et al. (Jun. 3, 2005). "Innovative Monolateral Approach for Closed-Chest Atrial Fibrillation Surgery," *The Annals of Thoracic Surgery* 80:e22-e25.

Björk, V.O. et al. (Aug. 1961). "Sequelae of Left Ventricular Puncture with Angiocardiography," *Circulation* 24:204-212.

Blackshear, J.L. et al. (Feb. 1996). "Appendage Obliteration to Reduce Stroke in Cardiac Surgical Patients With Atrial Fibrillation," *Ann. Thorac. Surg.* 61(2), 13 pages.

Blackshear, J.L. et al. (Oct. 1, 2003). "Thoracscopic Extracardiac Obliteration of the Left Atrial Appendage for Stroke Risk Reduction in Atrial Fibrillation," *J. Am. Coll. Cardiol.* 42(7):1249-1252.

Bonanomi, G. et al. (Jan. 1, 2003). "Left Atrial Appendectomy and Maze," *Journal of the American College of Cardiology* 41(1):169-171.

Bonow, R.O. et al. (1998). "Guidelines for the Management of Patients With Valvular Heart Disease: Executive Summary: A Report of the American College of Cardiology/American Heart Association Task Force on Practice Guidelines (Committee on Management of Patients With Valvular Heart Disease)," *Journal of the American Heart Association* 98:1949-1984.

Botham, R.J. et al. (May 1959). "Pericardial Tamponade Following Percutaneous Left Ventricular Puncture," *Circulation* 19:741-744.

Brock, R. et al. (1956). "Percutaneous Left Ventricular Puncture in the Assessment of Aortic Stenosis," *Thorax* 11:163-171.

Burke, R.P. et al. (1992). "Improved Surgical Approach to Left Atrial Appendage Aneurysm," *Journal of Cardiac Surgery* 7(2):104-107.

Canaccord Adams (Aug. 11, 2008). "A-Fib: Near a Tipping Point," 167 pages.

Chung, M.K. (Jul. 2003). "Current Clinical Issues in Atrial Fibrillation," *Cleveland Clinic Journal of Medicine* 70(Supp. 3):S6-S11.

Coffin, L.H. (Jun. 1985). "Use of the Surgical Stapler to Obliterate the Left Atrial Appendage," *Surgery, Gynecology & Obstetric* 160:565-566.

Connolly, S.J. (Sep. 7, 1999). "Preventing Stroke in Atrial Fibrillation: Why Are So Many Eligible Patients Not Receiving Anticoagulant Therapy?" *Canadian Medical Association* 161(5):533-534.

Costa, R. et al. (2006). "Bi-Atrial Subxiphoid Epicardial Pacemaker in Superior Vena Cava Syndrome," *Arq. Bras. Cardiol.* 87:e45-e47.

Cox, J.L. et al. (Apr. 1991). "The Surgical Treatment of Atrial Fibrillation: IV. Surgical Technique," *J. Thorac. Cardiovasc. Surg.* 101(4):584-592.

Cox, J.L. et al. (Aug. 1995). "Modification of the Maze Procedure for Atrial Flutter and Atrial Fibrillation I. Rationale and Surgical Results," *J. Thorac. Cardiovasc. Surg.* 110(2):473-484.

Cox, J.L. et al. (Aug. 1995). "Modification of the Maze Procedure for Atrial Flutter and Atrial Fibrillation II. Surgical Technique of the Maze III Procedure," *J. Thorac. Cardiovasc. Surg.* 110(2):485-495.

Cox, J.L. et al. (Nov. 1999). "Impact of the Maze Procedure on the Stroke Rate in Patients with Atrial Fibrillation," *J. Thorac. Cardiovasc. Surg.* 118:833-840.

Cox, J.L. et al. (2004). "The Role of Surgical Intervention in the Management of Atrial Fibrillation," *Texas Heart Institute Journal* 31(3):257-265.

Crystal, E. et al. (Jan. 2003). "Left Atrial Appendage Occlusion Study (LAAOS): A Randomized Clinical Trial of Left Atrial Appendage Occlusion During Routine Coronary Artery Bypass Graft Surgery for Long-term Stroke Prevention," *Am Heart J* 145(1):174-178.

D'Avila, A. et al. (Apr. 2003). "Pericardial Anatomy for the Interventional Electrophysiologist," *Journal of Cardiovascular Electrophysiology* 14(4):422-430.

D'Avila, A. et al. (Nov. 2007). "Experimental Efficacy of Pericardial Instillation of Anti-inflammatory Agents During Percutaneous Epicardial Catheter Ablation to Prevent Postprocedure Pericarditis," *Journal of Cardiovascular Electrophysiology* 18(11):1178-1183.

DeMaria, A.N. et al. (Dec. 17, 2003). "Highlights of the Year JACC 2003," *Journal of the American College of Cardiology* 42(12):2156-2166.

Deneu, S. et al. (Jul. 11, 1999). "Catheter Entrapment by Atrial Suture During Minimally Invasive Port-access Cardiac Surgery," *Canadian Journal of Anesthesia* 46(10):983-986.

Deponti, R. et al. (Mar. 7, 2006). "Trans-Septal Catheterization in the Electrophysiology Laboratory: Data From a Multicenter Survey Spanning 12 Years," *Journal of the American College of Cardiology* 47(5):1037-1042.

Donal, E. et al. (Sep. 2005). "The Left Atrial Appendage, a Small, Blind-Ended Structure: A Review of Its Echocardiographic Evaluation and Its Clinical Role," *Chest* 128(3):1853-1862.

Donnino, R. et al. (2007). "Left Atrial Appendage Thrombus Outside of a 'Successful' Ligation," *European Journal of Echocardiography* pp. 1-2.

Dullum, M.K.C. et al. (1999). "Xyphoid MIDCAB: Report of the Technique and Experience with a Less Invasive MIDCAB Procedure," *Heart Surgery Forum* 2(1):77-81.

(56) References Cited

OTHER PUBLICATIONS

Feinberg, W.M. et al. (Mar. 13, 1995). "Prevalence, Age Distribution, and Gender of Patients With Atrial Fibrillation," *Arch Intern Med* 155:469-473.

Fieguth, H.G. et al. (1997). "Inhibition of Atrial Fibrillation by Pulmonary Vein Isolation and Auricular Resection—Experimental Study in a Sheep Model," *European Journal of Cardio-Thoracic Surgery* 11:714-721.

Fisher, D.C. et al. (Dec. 1998). "Large Gradient Across a Partially Ligated Left Atrial Appendage," *Journal of the American Society of Echocardiography* 11(12):1163-1165.

Friberg, L. et al. (2006). "Stroke Prophylaxis in Atrial Fibrillation: Who Gets it and Who Does Not?" *European Heart Journal* 27:1954-1964.

Friedman, P.A. et al. (Aug. 2009). "Percutaneous Epicardial Left Atrial Appendage Closure: Preliminary Results of an Electrogram Guided Approach," *Journal of Cardiovascular Electrophysiology* 20(8):908-915.

Fuster, V. et al. (Oct. 2001). "ACC/AHA/ESC Guidelines for the Management of Patients with Atrial Fibrillation," *European Heart Journal* 22(20):1852-1923.

Garcia-Fernandez, M.A. et al. (Oct. 1, 2003). "Role of Left Atrial Appendage Obliteration in Stroke Reduction in Patients With Mitral Valve Prosthesis," *Journal of the American College of Cardiology* 42(7):1253-1258.

Gardiner, G.A. Jr. et al. (Apr. 1986). "Complications of Transluminal Angioplasty," *Radiology* 159:201-208.

Gillinov, A.M. (2007). "Advances in Surgical Treatment of Atrial Fibrillation," *Stroke* 38(part 2):618-623.

Gilman, R.A. et al. (Apr. 1963). "Direct Left Ventricular Puncture," *California Medicine* 98(4):200-203.

Goodwin, W.E. et al. (Nov. 1950). "Translumbar Aortic Puncture and Retrograde Catheterization of the Aorta in Aortography and Renal Arteriography," *Annals of Surgery* 132(5):944-958.

Gottlieb, L.K. et al. (Sep. 12, 1994). "Anticoagulation in Atrial Fibrillation," *Arch Intern Med.* 154:1945-1953.

Graffigna, A. et al. (1993). "Surgical Treatment of Wolff-Parkinson-White Syndrome: Epicardial Approach Without the Use of Cardiopulmonary Bypass," *J. Card. Surg.* 8:108-116.

Haissaguerre, M. et al. (Nov. 2005). "Catheter Ablation of Long-Lasting Persistent Atrial Fibrillation: Clinical Outcome and Mechanisms of Subsequent Arrhythmias," *Journal of Cardiovascular Electrophysiology* 16(11):1138-1147.

Halperin, J.L. et al. (Aug. 1988). "Atrial Fibrillation and Stroke: New Ideas, Persisting Dilemmas," *Journal of the American Heart Association* 19(8):937-941.

Halperin, J.L. et al. (Oct. 1, 2003). "Obliteration of the Left Atrial Appendage for Prevention of Thromboembolism," *Journal of the American College of Cardiology* 42(7):1259-1261.

Hammill, S.C. (May 2006). "Epicardial Ablation: Reducing the Risks," *J. Cardiovasc. Electrophysiol.* 17:550-552.

Hara, H. et al. (Jan. 2008). "Percutaneous Left Atrial Appendage Obliteration," *JACC: Cardiovascular Imagin* 1(1):92-93.

Hart, R.G. et al. (Nov. 2, 1999). "Atrial Fibrillation and Thromboembolism: A Decade of Progress in Stroke Prevention," *Annals of Internal Medicine* 131(9):688-695.

Hart, R.G. et al. (2001). "Atrial Fibrillation and Stroke: Concepts and Controversies," *Stroke* 32:803-808.

Hart, R.G. (Sep. 11, 2003). "Atrial Fibrillation and Stroke Prevention," *The New England Journal of Medicine* 49(11):1015-1016.

Healey, J.S. et al. (Oct. 2003). "Surgical Closure of the Left Atrial Appendage for the Prevention of Stroke: A Randomized Pilot Trial of Safety and Efficacy (The Left Atrial Appendage Occlusion Study—LAAOS)," presented at the Canadian Cardiovascular Congress 2003, Toronto, Canada, Abstract No. 666, 2 pages.

Healey, J.S. et al. (Aug. 2005). "Left Atrial Appendage Occlusion Study (LAAOS): Results of a Randomized Controlled Pilot Study of Left Atrial Appendage Occlusion During Coronary Bypass Surgery in Patients at Risk for Stroke," *American Heart Journal* 150(2):288-293.

Hein, R. et al. (2005). "Patent Foramen Ovale and Left Atrial Appendage: New Devices and Methods for Closure," *Pediatric Cardiology* 26(3):234-240.

Heist, E.K. et al. (Nov. 2006). "Analysis of the Left Atrial Appendage by Magnetic Resonance Angiography in Patients with Atrial Fibrillation," *Heart Rhythm* 3(11):1313-1318.

Ho, I. et al. (Apr. 24, 2007). "Percutaneous Epicardial Mapping Ablation of a Posteroseptal Accessory Pathway," *Circulation* 115:e418-e421.

Ho, S.Y. et al. (Nov. 1999). "Anatomy of the Left Atrium: Implications for Radiofrequency Ablation of Atrial Fibrillation," *Journal of Cardiovascular Electrophysiology* 10(11):1525-1533.

Hoit, B.D. et al. (Jan. 1993). "Altered Left Atrial Compliance After Atrial Appendectomy. Influence on Left Atrial and Ventricular Filling," *Circulation Research* 72(1):167-175.

Inoue, Y. et al. (Jul.-Aug. 1997). "Video Assisted Thoracoscopic and Cardioscopic Radiofrequency Maze Ablation," *Asaio Journal* 43(4):334-337, Abstract Only.

Jaïs, P. et al. (2003). "Radiofrequency Ablation for Atrial Fibrillation," *European Society of Cardiology* 5(Supplement H):H34-H39.

Johnson, W.D. et al. (2000). "The Left Atrial Appendage: Our Most Lethal Human Attachment! Surgical Implications," *Euro. J. Cardiothoracic. Surg.* 17:718-722.

Jongbloed, M.R.M. et al. (2005). "Clinical Applications of Intracardiac Echocardiography in Interventional Procedures," *Heart* 91:981-990.

Kamohara, K. et al. (Aug. 2006). "Evaluation of a Novel Device for Left Atrial Appendage Exclusion: The Second-generation Atrial Exclusion Device," *The Journal of Thoracic and Cardiovascular Surgery* 132(2):340-346.

Kanderian, A.S. et al. (2008). "Success of Surgical Left Atrial Appendage Closure: Assessment by Transesophageal Echocardiography," *Journal of the American College of Cardiology* 52(11): 924-929.

Kato, H. et al. (Aug. 1, 1996). "Evaluation of Left Atrial Appendage Stasis in Patients With Atrial Fibrillation Using Transesophageal Echocardiography With an Intravenous Albumin-Contrast Agent," *The American Journal of Cardiology* 78:365-369.

Katz, E.S. et al. (Aug. 2000). "Surgical Left Atrial Appendage Ligation is Frequently Incomplete: A Transesophageal Echocardiographic Study," *Journal of the American College of Cardiology* 36(2):468-471.

Kenner, H.M. et al. (Dec. 1966). "Intrapericardial, Intrapleural, and Intracardiac Pressures During Acute Heart Failure in Dogs Studied without Thoracotomy," *Circulation Research* 19:1071-1079.

Kerut, E.K. et al. (Jul. 2008). "Anatomy of the Left Atrial Appendage," *Echocardiography* 25(6):669-673.

Khargi, K. et al. (2005). "Surgical Treatment of Atrial Fibrillation: A Systematic Review," *European Journal of Cardiothoracic Surgery* 27:258-265.

Kim, K.B. et al. (Jan. 1998). "Effect of the Cox Maze Procedure on the Secretion of Atrial Natriuretic Peptide," *J. Thorac. Cardiovasc. Surg.* 115(1):139-146; discussion 146-147.

Kistler, P.M. et al. (May 2007). "The Left Atrial Appendage: Not Just an Innocent Bystander," *J. Cardiovasc Electrophysiol* 18(5):465-466.

Klein, H. et al. (Apr. 1990). "The Implantable Automatic Cardioverter-Defibrillator," *Herz* 15(2):111-125, Abstract Only.

Kolb, C. et al. (Feb. 2004). "Incidence of Antitachycardia Therapy Suspension Due to Magnet Reversion in Implantable Cardioverter Defibrillators," *Pace* 27:221-223.

Krikorian, J.G. et al. (Nov. 1978). "Pericardiocentesis," *Am. J. Med.* 65(5):808-814.

Krum, D. et al. (2004). "Visualization of Remnants of the left Atrial Appendage Following Epicardial Surgical Removal," *Heart Rhythm* 1:249.

Lacomis, J.M. et al. (Oct. 2003). "Multi-Detector Row CT of the Left Atrium and Pulmonary Veins before Radio-frequency Catheter Ablation for Atrial Fibrillation," *Radio Graphics* 23:S35-S48.

Lacomis, J.M. et al. (2007, e-pub. Oct. 17, 2007). "Dynamic Multidimensional Imaging of the Human Left Atrial Appendage," *Europace* 9:1134-1140.

(56) References Cited

OTHER PUBLICATIONS

Lee, R. et al. (1999). "The Closed Heart MAZE: A Nonbypass Surgical Technique," *The Annals of Thoracic Surgery* 67:1696-1702.
Levinson, M.L. et al. (1998). "Minimally Invasive Atrial Septal Defect Closure Using the Subxyphoid Approach," *Heart Surg. Forum* 1(1):49-53, Abstract Only.
Lewis, D.R. et al. (1999). "Vascular Surgical Intervention for Complications of Cardiovascular Radiology: 13 Years' Experience in a Single Centre," *Ann. R. Coll. Surg. Engl.* 81:23-26.
Li, H. (2007). "Magnet Decoration, Beautiful but Potentially Dangerous for Patients with Implantable Pacemakers or Defibrillators," *Heart Rhythm* 4(1):5-6.
Lindsay, B.D. (1996). "Obliteration of the Left Atrial Appendage: A Concept Worth Testing," *The Annals of Thoracic Surgery* 61:515.
Lip, G.Y.H. et al. (Jun. 2001). "Thromboprophylaxis for Atrial Flutter," *European Heart Journal* 22(12):984-987.
Lustgarten, D.L. et al. (May/Jun. 1999). "Cryothermal Ablation: Mechanism of Tissue Injury and Current Experience in the Treatment of Tachyarrhythmias," *Progress in Cardiovascular Diseases* 41(6):481-498.
Macris, M. et al. (Jan. 1999). "Minimally Invasive Access of the Normal Pericardium: Initial Clinical Experience with a Novel Device," *Clin. Cardiol.* 22(Suppl. I)I-36-I-39.
Maisch, B. et al. (Jan. 1999). "Intrapreicardial Treatment of Inflammatory and Neoplastic Pericarditis Guided by Pericardioscopy and Epicardial Biopsy-Results from a Pilot Study," *Clin. Cardiol.* 22(Supp. I):I-17-I-22.
Mannam, A.P. et al. (Apr. 1, 2002). "Safety of Subxyphoid Pericardial Access Using a Blunt-Tip Needle," *The American Journal of Cardiology* 89:891-893.
Mattox, K.L. et al. (May 1997). "Newer Diagnostic Measure and Emergency Management," *Ches Surg Clin N Am.* 7(2):213-226, Abstract Only.
McCarthy, P.M. et al. (2008). "Epicardial Atrial Fibrillation Ablation," Chapter 23 in *Contemporary Cardiology: Atrial Fibrillation, From Bench to Bedside,* Natale, A. et al. eds., Humana Press,: Totowa, NJ, pp. 323-332.
McCaughan, J.J. Jr., et al. (Nov. 1957). "Aortography Utilizing Percutaneous Left Ventricular Puncture," located at <http://www.archsurg.com>, last visited on Apr. 7, 2009, 73:746-751, Abstract Only.
McClelland, R.R. (1978). "Congenital Aneurysmal Dilatation of the Left Auricle Demonstrated by Sequential Cardiac Blood-Pool Scintiscanning," *J. Nucl. Med.* 19(5):507-509.
Melo, J. et al. (Apr. 21, 2008). "Surgery for Atrial Fibrillation in Patients with Mitral Valve Disease: Results at Five Years from the International Registry of Atrial Fibrillation Surgery," *The Journal of Thoracic and Cardiovascular Surgery* 135(4):863-869.
Miller, P.S.J. et al. (Feb. 2005). "Are Cost Benefits of Anticoagulation for Stroke Prevention in Atrial Fibrillation Underestimated?" *Stroke* 36:360-366.
Miyasaka, Y. et al. (Jul. 11, 2006). "Secular Trends in Incidence of Atrial Fibrillation in Olmsted County, Minnesota, 1980 to 2000, and Implications on the Projections for Future Prevalence," *Circulation* 114:119-125.
Morris, J.J. Jr. (1979). "Transvenous versus Transthoracic Cardiac Pacing," Chapter 16 in *Cardiac Pacing: A Concise Guide to Clinical Practice*, pp. 239-245.
Mráz, T. et al. (Apr. 2007). "Role of Echocardiography in Percutaneous Occlusion of the left Atrial Appendage," *Echocardiography* 24(4):401-404.
Naclerio, E.A. et al. (1979). "Surgical Techniques for Permanent Ventricular Pacing," Chapter 10 in *Cardiac Pacing: A Concise Guide to Clinical Practice*, pp. 145-168.
Nakai, T. et al. (May 7, 2002). "Percutaneous Left Atrial Appendage Occlusion (PLAATO) for Preventing Cardioembolism: First Experience in Canine Model," *Circulation* 105:2217-2222.

Nakajima, H. et al. (2004). "Consequence of Atrial Fibrillation and the Risk of Embolism After Percutaneous Mitral Commissurotomy: The Necessity of the Maze Procedure," *The Annals of Thoracic Surgery* 78:800-806.
Odell, J.A. et al. (1996). "Thorascopic Obliteration of the Left Atrial Appendage: Potential for Stroke Reduction?" *Ann. Thorac. Surg.* 61:565-569.
O'Donnell, M. et al. (2005). "Emerging Therapies for Stroke Prevention in Atrial Fibrillation," *European Heart Journal* 7(Supplement C):C19-C27.
Omran, H. et al. (1997). "Left Atrial Appendage Function in Patients with Atrial Flutter," *Heart* 78:250-254.
Onalan, O. et al. (2005). "Nonpharmacologic Stroke Prevention in Atrial Fibrillation," *Expert Rev. Cardiovasc. Ther.* 3(4):619-633.
Onalan, O. et al. (2007). "Left Atrial Appendage Exclusion for Stroke Prevention in Patients With Nonrheumatic Atrial Fibrillation," *Stroke* 38(part 2):624-630.
Ostermayer, S. et al. (2003). "Percutaneous Closure of the Left Atrial Appendage," *Journal of Interventional Cardiology* 16(6):553-556.
Ota, T. et al. (2006). "Epicardial Atrial Ablation Using a Novel Articulated Robotic Medical Probe via a Percutaneous Subxiphoid Approach," *National Institute of Health* 1(6):335-340.
Ota, T. et al. (Oct. 2007). "Impact of Beating Heart left Atrial Ablation on Left-sided Heart Mechanics," *The Journal of Thoracic and Cardiovascular Surgery* 134:982-988.
Pennec, P-Y. et al. (2003). "Assessment of Different Procedures for Surgical Left Atrial Appendage Exclusion," *The Annals of Thoracic Surgery* 76:2167-2168.
Perk, G. et al. (Aug. 2009). "Use of Real Time Three-Dimensional Transesophageal Echocardiography in Intracardiac Catheter Based Interventions," *J. Am Soc Echocardiogr* 22(8):865-882.
Pollick C. (Feb. 2000). "Left Atrial Appendage Myopathy," *Chest* 117(2):297-308.
Poulsen, T.S. et al. (Feb. 15, 2005). "Is Aspirin Resistance or Female Gender Associated With a High Incidence of Myonecrosis After Nonurgent Percutaneous Coronary Intervention?" *J. Am. Coll. Cardiol.* 45(4):635-636.
Reznik, G. et al. (Oct. 1992). "Percutaneous Endoscopic Implantation of Automatic Implantable Cardioverter/Defibrillator (AICD): An Animal Study of a New Nonthoracotomy Technique," *J. Laparoendosc. Surg.* 2(5):255-261, Abstract Only.
Robicsek, F. (1987). "Closed-Chest Decannulation of Transthoracically Inserted Aortic Balloon Catheter without Grafting," *Journal of Cardiac Surgery* 2(2):327-329.
Ross, J. Jr. et al. (Jun. 3, 2008). "Transseptal Left Heart Catheterization: A 50-Year Odyssey," *Journal of the American College of Cardiology* 51 (22):2107-2115.
Rubin, D.N. et al. (Oct. 1, 1996). "Evaluation of Left Atrial Appendage Anatomy and Function in Recent-Onset Atrial Fibrillation by Transesophageal Echocardiography," *Am J Cardiol* 78:774-778.
Ruchat, P. et al. (2002). "Off-pump Epicardial Compartmentalization for Ablation of Atrial Fibrillation," *Interactive Cardio Vascular and Thoracic Surgery* 1:55-57.
Salzberg, S.P. et al. (2008). "Surgical Left Atrial Appendage Occlusion: Evaluation of a Novel Device with Magnetic Resonance Imaging," *European Journal of Cardiothoracic Surgery* 34:766-770.
Sapp, J. et al. (Dec. 2001). "Electrophysiology and Anatomic Characterization of an Epicardial Accessory Pathway," *Journal of Cardiovascular Electrophysiology* 12(12):1411-1414.
Scharf, C. et al. (2005). "Catheter Ablation for Atrial Fibrillation: Pathophysiology, Techniques, Results and Current Indications," *Continuous Medical Education* 8:53-61.
Scherr, D. et al. (Apr. 2009). "Incidence and Predictors of left Atrial Thrombus Prior to Catheter Ablation of Atrial Fibrillation," *Journal of Cardiovascular Electrophysiology* 20(4):379-384.
Schmidt, H. et al. (Sep. 2001). "Prevalence of Left Atrial Chamber and Appendage Thrombi in Patients With Atrial Flutter and Its Clinical Significance," *Journal of the American College of Cardiology* 38(3):778-784.

(56) References Cited

OTHER PUBLICATIONS

Schneider, B. et al. (2005, e-pub. Aug. 22, 2005). "Surgical Closure of the Left Atrial Appendage—A Beneficial Procedure?" *Cardiology* 104:127-132.
Schweikert, R.A. et al. (Sep. 16, 2003). "Percutaneous Pericardial Instrumentation for Endo-Epicardial Mapping of Previously Failed Ablation," *Circulation* 108:1329-1335.
Schweikert, R.A. et al. (2005). "Epicardial Access: Present and Future Applications for Interventional Electrophysiologists," Chapter 25 in *New Arrhythmia Technolgies*, Wang, P.J. ed., Blackwell Publishing, pp. 242-256.
Seferovic, P. et al. (Jan. 1999). "Initial Clinical Experience with the PerDUCER® Device: Promising New Tool in the Diagnosis and Treatment of Pericardial Disease," *Clin. Cardiol.* 22(Supp I):I-30-I-35.
Sengupta, P.P. et al. (2005). "Transoesophageal Echocardiography," *Heart* 91:541-547.
Sharada, K. et al. (2005). "Non-Surgical Transpericardial Catheter Ablation of Post-Infarction Ventricular Tachycardia," *Indian Heart J* 57:58-61.
Sievert, H. et al. (Apr. 23, 2002). "Percutaneous Left Atrial Appendage Transcatheter Occlusion to Prevent Stroke in High-Risk Patients With Atrial Fibrillation," *Circulation* 105:1887-1889.
Singer, D.E. et al. (Sep. 2004). "Antithrombotic Therapy in Atrial Fibrillation: The Seventh ACCP Conference on Antithrombotic and Thrombolytic Therapy," *Chest* 126(3):429S-456S.
Smith, P.W. et al. (Nov. 1956). "Diagnosis of Mitral Regurgitation by Cardioangiography," *Circulation* 14:847-853.
Soejima, K. et al. (2004). "Subxiphoid Surgical Approach for Epicardial Catheter-Based Mapping and Ablation in Patients With Prior Cardiac Surgery or Difficult Pericardial Access," *Circulation* 110:1197-1201.
Sosa, E. et al. (1996). "A New Technique to Perform Epicardial Mapping in the EP Laboratory," *J. Cardiovasc. Electrophysiol.* 7(6):531-536.
Sosa, E. et al. (Mar. 1998). "Endocardial and Epicardial Ablation Guided by Nonsurgical Transthoracic Epicardial Mapping to Treat Recurrent Ventricular Tachycardia," *J. Cardiovasc. Elecytophysiol.* 9(3):229-239.
Sosa, E. et al. (Dec. 14, 1999). "Different Ways of Approaching the Normal Pericardial Space," *Circulation* 100(24):e115-e116.
Sosa, E. et al. (Jul. 15, 2002). "Gaining Access to the Pericardial Space," *The American Journal of Cardiology* 90:203-204.
Sosa, E. et al. (Apr. 2005). "Epicardial Mapping and Ablation Techniques to Control Centricular Tachycardia," *Journal of Cardiovasc. Electrphsiol.* 16(4):449-452.
Sparks, P.B. et al. (2001). "Is Atrial Flutter a Risk Factor for Stroke?" *Journal of the American College of Cardiology* 38(3):785-788.
Spodick, D.H. (Nov. 1970). "Medical History of the Pericardium," *The American Journal of Cardiology* 26:447-454.
Stewart, J.M. et al. (Apr. 1992). "Bilateral Atrial Appendectomy Abolishes Increased Plasma Atrial Natriuretic Peptide Release and Blunts Sodium and Water Excretion During Volume Loading in Conscious Dogs," *Circulation Research* 70(4):724-732.
Stewart, S. (1974). "Placement of the Sutureless Epicardial Pacemaker Lead by the Subxiphoid Approach," *Ann. of Thoracic Surg.* 18(3):308-313.
Stoddard, M.F. et al. (1995). "Left Atrial Appendage Thrombus is not Uncommon in Patients with Acute Atrial Fibrillation and a Recent Embolic Event: A Transesophageal Echocardiographic Study," *J. Am. Coll. Cardiol.* 25:452-459, Abstract Only.
Stokes, K. (Jun. 1990). "Implantable Pacing Lead Technology," *IEEE Engineering in Medicine and Biology* pp. 43-49.
Stöllberger, C. et al. (2000). "Is the Left Atrial Appendage Our Most Lethal Attachment?" *European Journal of Cardio-Thoracic Surgery* 18:625-626.
Stöllberger, C. et al. (Dec. 2003). "Elimination of the Left Atrial Appendage to Prevent Stroke or Embolism?: Anatomic, Physiologic, and Pathophysiologic Considerations," 124(6):2356-2362.

Stöllberger, C. et al. (2006). "Stroke Prevention by Means of Epicardial Occlusion of the Left Atrial Appendage," *Journal of Thoracic and Cardiovascular Surgery* 132(1):207-208.
Stöllberger, C. et al. (2007). "Arguments Against Left Atrial Appendage Occlusion for Stroke Prevention," *Stroke* 38:e77.
Stöllberger, C. et al. (2007). "Leave the Left Atrial Appendage Untouched for Stroke Prevention!" *Journal of Thoracic and Cardiovascular Surgery* 134(2):549-550.
Su, P. et al. (Sep. 2008, e-pub. May 8, 2007). "Occluding the Left Atrial Appendage: Anatomical Considerations," *Heart* 94(9):1166-1170.
Subramanian, V.A. (Jun. 1997). "Less Invasive Arterial CABG on a Beating Heart," *Ann. Thorac. Surg.* 63(6 Suppl.):S68-S71.
Subramanian, V.A. et al. (Dec. 1997). "Minimally Invasive Direct Coronary Artery Bypass Grafting: two-Year Clinical Experience," *Ann. Thorac. Surg.* 64(6):1648-1653, Abstract Only.
Suehiro, S. et al. (1996). "Echocardiography-Guided Pericardiocentesis With a Needle Attached to a Probe," *Ann. Thoracic Surg.* 61:741-742.
Sun, F. et al. (Feb. 2006). "Subxiphoid Access to Normal Pericardium with Micropuncture Set: Technical Feasibility Study in Pigs," *Radiology* 238(2):719-724.
Szili-Torok, T. et al. (2001). "Transseptal Left heart Catheterisation Guided by Intracardiac Echocardiography," *Heart* 86:e11-e15.
Tabata, T. et al. (Feb. 1, 1998). "Role of Left Atrial Appendage in left Atrial Reservoir Function as Evaluated by Left Atrial Appendage Clamping During Cardiac Surgery," *The American Journal of Cardiology* 81:327-332.
Tomar, M. et al. (Jul.-Aug. 2006). "Transcatheter Closure of Fossa Ovalis Atrial Septal Defect: A Single Institutional Experience," *Indian Heart Journal* 58(4):325-329.
Troughton, R.W. et al. (Feb. 28, 2004). "Pericarditis," *The Lancet* 363:717-727.
Ulicny K.S. et al. (Jun. 1992). "Conjoined Subrectus Pocket for Permanent Pacemaker Placement in the Neonate," *Ann Thorac Surg.* 53(6):1130-1131, Abstract Only.
Valderrabano, M. et al. (Sep. 2004). "Percutaneous Epicardial Mapping During Ablation of Difficult Accessory Pathways as an Alternative to Cardiac Surgery," *Heart Rhythm* 1(3):311-316.
Von Korn, H. et al. (2006). "Simultaneous Combined Interventional Percutaneous Left Atrial Auricle and Atrial Septal Defect Closure," *Heart* 92:1462.
Wang, T.J. et al. (Aug. 27, 2003). "A Risk Score for Predicting Stroke or Death in Individuals With New-Onset Atrial Fibrillation in the Community," *American Medical Association* 290(8):1049-1056.
Watkins, L. et al. (Nov. 1982). "Implantation of the Automatic Defibrillator: The Subxiphoid Approach," *Ann. of Thoracic Surg.* 34(5):515-520.
W.L. Gore & Associates (Aug. 11, 2006). "Gore Helex™ Septal Occluder," located at <http://www.fda.gov/cdrh/pdf5/p050006a.pdf>, last visited on Jun. 14, 2007, 3 pages.
Wolber, T. et al. (Jan. 2007). "Potential Interference of Small Neodymium Magnets with Cardiac pacemakers and Implantable Cardioverter-defibrillators," *Heart Rhythm* 4(1):1-4.
Wolf, P.A. et al. (Oct. 1978). "Epidemiologic Assessment of Chronic Atrial Fibrillation and Risk of Stroke: The Fiamingham Study," *Neurology* 28:973-977.
Wolf, P.A. et al. (Aug. 1991). "Atrial Fibrillation as an Independent Risk Factor for Stroke: The Framingham Study," *Stroke* 22(8):983-988.
Wolf, P.A. et al. (Feb. 9, 1998). "Impact of Atrial Fibrillation on Mortality, Stroke, and Medical Costs," *Arch Intern Med* 158:229-234.
Wong, J.W.W. et al. (2006). "Impact of Maze and Concomitant Mitral Valve Surgery on Clinical Outcomes," *The Annals of Thoracic Surgery* 82:1938-1947.
Wongcharoen, W. et al. (Sep. 2006). "Morphologic Characteristics of the Left Atrial Appendage, Roof, and Septum: Implications for the Ablation of Atrial Fibrillation," *Journal of Cardiovascular Electrophysiology* 17(9):951-956.

(56) References Cited

OTHER PUBLICATIONS

Wood, M.A. (Jan. 2006). "Percutaneous Pericardial Instrumentation in the Electrophysiology Laboratory: A Case of Need," *Heart Rhythm* 3(1):11-12.
Wudel, J.H. et al. (Apr. 3, 2008). "Video-Assisted Epicardial Ablation and left Atrial Appendage Exclusion for Atrial Fibrillation: Extended Follow-Up," *The Annals of Thoracic Surgery* 85:34-38.
Wyse, D.G. et al. (Dec. 5, 2002). "Of 'Left Atrial Appendage Amputation, Ligation, or Occlusion in Patients with Atrial Fibrillation'," *N Engl J Med* 347(23):1825-1833, Abstract Only.
Yamada, Y. et al. (Aug. 2006). "Video-Assisted Thoracoscopy to Treat Atrial Tachycardia Arising from Left Atrial Appendage," *Journal of Cardiovascular Electrophysiology* 17(8):895-898.
Zapolanski, A. et al. (May 2008). "Safe and Complete Exclusion of the left Atrial Appendage, A Simple Epicardial Approach," *Innovations* 3(3):161-163.
Zenati, M.A. et al. (Sep. 2003). "Left Heart Pacing Lead Implantation Using Subxiphoid Videopericardioscopy," *Journal of Cardiovascular Electrophysiology* 14(9):949-953.
Zenati, M.A. et al. (2004). "Mechanical Function of the Left Atrial Appendage Following Epicardial Bipolar Radiofrequency Ablation," *Cardiothoracic Techniques and Technologies X*, Abstract 121A, p. 176.
Zenati, M.A. et al. (2005). "Modification of the Left Atrial Appendage," Chapter 12 in *Innovative Management of Atrial Fibrillation*, Schwartzman, David ed., Blackwell Science Ltd., 5 pages.
Extended European Search Report dated Jul. 10, 2015, for European Patent Application No. 15153029.2, filed on Mar. 25, 2008, 6 pages.
Extended European Search Report dated Jun. 9, 2015, for EP Application No. 12 797 543.1, filed on Jun. 7, 2012, 6 pages.
Extended European Search Report dated Oct. 14, 2016, for EP Application No. 14 779 388.9 filed on Mar. 3, 2014, 7 pages.
Extended European Search Report dated Feb. 10, 2017, for EP Application No. 10 759 425.1, filed on Apr. 1, 2010, 7 pages.
International Search Report dated May 19, 2008, for PCT Application No. PCT/US06/013459, filed on Apr. 7, 2006, 1 page.
International Search Report dated Feb. 27, 2007, for PCT Application No. PCT/US2008/003938, filed on Mar. 25, 2008, 5 pages.
International Search Report dated Jul. 30, 2010, for PCT Application No. PCT/US2008/076703, filed on Sep. 17, 2008, 2 pages.
International Search Report dated Jun. 1, 2010, for PCT Application No. PCT/US2010/029668, filed on Apr. 1, 2010, 2 pages.
International Search Report dated Sep. 14, 2012, for PCT Patent Application No. PCT/US2012/41285, filed on Jun. 7, 2012, 2 pages.
International Search Report dated Aug. 8, 2014, for PCT Application No. PCT/US2014/020030, filed on Mar. 3, 2014, 4 pages.
International Search Report dated May 4, 2017, for PCT Application No. PCT/US2017/019495, filed on Feb. 24, 2017, 2 pages.
Supplementary Search Report dated Mar. 14, 2011, for EP Application No. 04 794 730.4, filed on Oct. 11, 2004, 4 pages.
Written Opinion dated May 19, 2008, for PCT Application No. PCT/US06/013459, filed on Apr. 7, 2006, 6 pages.
Written Opinion of the International Searching Authority dated Feb. 27, 2007, for PCT Application No. PCT/US2008/003938, filed on Mar. 25, 2008, 10 pages.
Written Opinion of the International Searching Authority dated Jul. 30, 2010, for PCT Application No. PCT/US2008/076703, filed on Sep. 17, 2008, 8 pages.
Written Opinion of the International Searching Authority dated Jun. 1, 2010, for PCT Application No. PCT/US2010/029668, filed on Apr. 1, 2010, 8 pages. (5.40).
Written Opinion from the International Searching Authority dated Sep. 14, 2012, for PCT Patent Application No. PCT/US2012/41285, filed on Jun. 7, 2012; 6 pages (9.40).
Written Opinion of the International Searching Authority dated Aug. 8, 2014, for PCT Application No. PCT/US2014/020030, filed on Mar. 3, 2014, 6 pages (13.40).
Written Opinion of the International Searching Authority dated May 4, 2017, for PCT Application No. PCT/US2017/019495, filed on Feb. 24, 2017, 7 pages.
Non-Final Office Action dated Mar. 13, 2008 for U.S. Appl. No. 10/963,371, filed Oct. 11, 2004, 13 pages.
Non-Final Office Action dated Aug. 6, 2008 for U.S. Appl. No. 10/963,371, filed Oct. 11, 2004, 12 pages.
Final Office Action dated Jun. 22, 2009, for U.S. Appl. No. 10/963,371, filed Oct. 11, 2004, 11 pages.
Notice of Allowance dated Sep. 17, 2010, for U.S. Appl. No. 10/963,371, filed Oct. 11, 2004, 7 pages.
Non-Final Office Action dated Jun. 26, 2009, for U.S. Appl. No. 11/600,671, filed Nov. 15, 2006, 9 pages.
Final Office Action dated Apr. 14, 2010, for U.S. Appl. No. 11/600,671, filed Nov. 15, 2006, 7 pages.
Notice of Allowance dated Sep. 17, 2010, for U.S. Appl. No. 11/600,671, filed Nov. 15, 2006, 7 pages.
Non-Final Office Action dated Jul. 22, 2010, for U.S. Appl. No. 12/037,802, filed Feb. 26, 2008, 10 pages.
Final Office Action dated Apr. 26, 2011, for U.S. Appl. No. 12/037,802, filed Feb. 26, 2008, 9 pages.
Non-Final Office Action dated Jan. 16, 2013, for U.S. Appl. No. 12/037,802, filed Feb. 26, 2008, 11 pages.
Final Office Action dated Nov. 8, 2013, for U.S. Appl. No. 12/037,802, filed Feb. 26, 2008, 15 pages.
Notice of Allowance dated Apr. 3, 2014, for U.S. Appl. No. 12/037,802, filed Feb. 26, 2008, 8 pages.
Non-Final Office Action dated Mar. 7, 2012, for U.S. Appl. No. 12/124,023, filed May 20, 2008, 13 pages.
Final Office Action dated Oct. 18, 2012, for U.S. Appl. No. 12/124,023, filed May 20, 2008, 15 pages.
Non-Final Office Action dated May 31, 2013, for U.S. Appl. No. 12/124,023, filed May 20, 2008, 14 pages.
Non-Final Office Action dated May 4, 2015, for U.S. Appl. No. 12/124,023, filed May 20, 2008, 8 pages.
Notice of Allowance dated Oct. 21, 2015, for U.S. Appl. No. 12/124,023, filed May 20, 2008, 9 pages.
Non-Final Office Action dated Dec. 30, 2009, for U.S. Appl. No. 11/400,714, filed Apr. 7, 2006, 8 pages.
Final Office Action dated Jul. 21, 2010, for U.S. Appl. No. 11/400,714, filed Apr. 7, 2006, 10 pages.
Notice of Allowance dated Nov. 24, 2010, for U.S. Appl. No. 11/400,714, filed Apr. 7, 2006, 8 pages.
Non-Final Office Action dated Dec. 22, 2011, for U.S. Appl. No. 13/033,532, filed Feb. 23, 2011, 8 pages.
Final Office Action dated Jul. 11, 2012, for U.S. Appl. No. 13/033,532, filed Feb. 23, 2011, 8 pages.
Non-Final Office Action dated Apr. 2, 2014, for U.S. Appl. No. 13/033,532, filed Feb. 23, 2011, 8 pages.
Final Office Action dated Aug. 12, 2014, for U.S. Appl. No. 13/033,532, filed Feb. 23, 2011, 7 pages.
Non-Final Office Action dated Oct. 28, 2015, for U.S. Appl. No. 13/033,532, filed Feb. 23, 2011, 9 pages.
Final Office Action dated Apr. 1, 2016, for U.S. Appl. No. 13/033,532, filed Feb. 23, 2011, 8 pages.
Non-Final Office Action dated Nov. 15, 2010, for U.S. Appl. No. 12/055,213, filed Mar. 25, 2008, 18 pages.
Non-Final Office Action dated Apr. 28, 2011, for U.S. Appl. No. 12/055,213, filed Mar. 25, 2008, 20 pages.
Final Office Action dated Oct. 28, 2011, for U.S. Appl. No. 12/055,213, filed Mar. 25, 2008, 15 pages.
Non-Final Office Action dated Sep. 18, 2013, for U.S. Appl. No. 12/055,213, filed Mar. 25, 2008, 15 pages.
Notice of Allowance dated Mar. 4, 2014, for U.S. Appl. No. 12/055,213, filed Mar. 25, 2008, 9 pages.
Non-Final Office Action dated Oct. 27, 2011, for U.S. Appl. No. 12/363,359, filed Jan. 30, 2009, 11 pages.
Final Office Action dated May 4, 2012, for U.S. Appl. No. 12/363,359, filed Jan. 30, 2009, 10 pages.
Non-Final Office Action dated Jun. 17, 2014, for U.S. Appl. No. 12/363,359, filed Jan. 30, 2009, 7 pages.
Final Office Action dated Nov. 14, 2014, for U.S. Appl. No. 12/363,359, filed Jan. 30, 2009, 10 pages.
Non-Final Office Action dated Sep. 10, 2015, for U.S. Appl. No. 12/363,359, filed Jan. 30, 2009, 13 pages.

(56) References Cited

OTHER PUBLICATIONS

Final Office Action dated Mar. 17, 2016, for U.S. Appl. No. 12/363,359, filed Jan. 30, 2009, 10 pages.
Non-Final Office Action dated Nov. 9, 2011, for U.S. Appl. No. 12/363,381, filed Jan. 30, 2009, 10 pages.
Final Office Action dated May 16, 2012, for U.S. Appl. No. 12/363,381, filed Jan. 30, 2009, 8 pages.
Notice of Allowance dated Apr. 1, 2014, for U.S. Appl. No. 12/363,381, filed Jan. 30, 2009, 9 pages.
Notice of Allowance dated Dec. 29, 2014, for U.S. Appl. No. 12/363,381, filed Jan. 30, 2009, 9 pages.
Non-Final Office Action dated Feb. 17, 2011, for U.S. Appl. No. 12/212,511, filed Sep. 17, 2008, 14 pages.
Final Office Action dated Sep. 20, 2011, for U.S. Appl. No. 12/212,511, filed Sep. 17, 2008, 8 pages.
Non-Final Office Action dated Apr. 2, 2012, for U.S. Appl. No. 12/212,511, filed Sep. 17, 2008, 5 pages.
Final Office Action dated Jul. 24, 2012, for U.S. Appl. No. 12/212,511, filed Sep. 17, 2008, 6 pages.
Notice of Allowance dated Feb. 22, 2013, for U.S. Appl. No. 12/212,511, filed Sep. 17, 2008, 8 pages.
Notice of Allowance dated Mar. 18, 2013, for U.S. Appl. No. 12/212,511, filed Sep. 17, 2008, 6 pages.
Non-Final Office Action dated Mar. 29, 2013, for U.S. Appl. No. 12/752,873, filed Apr. 1, 2010, 16 pages.
Non-Final Office Action dated Dec. 2, 2016, for U.S. Appl. No. 14/625,540, filed Feb. 18, 2015, 20 pages.
Final Office Action dated Jan. 13, 2014, for U.S. Appl. No. 12/752,873, filed Apr. 1, 2010, 10 pages.
Non-Final Office Action dated Nov. 10, 2014, for U.S. Appl. No. 12/752,873, filed Apr. 1, 2010, 10 pages.
Notice of Allowance dated Jul. 22, 2015, for U.S. Appl. No. 12/752,873, filed Apr. 1, 2010, 8 pages.
Non-Final Office Action dated Mar. 31, 2015, for U.S. Appl. No. 13/490,919, filed Jun. 7, 2012, 14 pages.
Final Office Action dated Nov. 18, 2015, for U.S. Appl. No. 13/490,919, filed Jun. 7, 2012, 10 pages.
Notice of Allowance dated Apr. 11, 2016, for U.S. Appl. No. 14/195,797, filed Mar. 3, 2014, 14 pages.
Notice of Allowance dated Jul. 19, 2016, for U.S. Appl. No. 13/490,919, filed Jun. 7, 2012, 10 pages.
Extended European Search Report dated Aug. 21, 2018, for EP Application No. 18168824.3, 5 pages.
Final Office Action dated Jun. 8, 2017, for U.S. Appl. No. 14/625,540, filed Feb. 18, 2015, 14 pages.
Final Office Action dated Sep. 6, 2018, for U.S. Appl. No. 14/625,540, filed Feb. 18, 2015, 15 pages.
Non-Final Office Action dated Jan. 12, 2018, for U.S. Appl. No. 14/928,836, filed Oct. 30, 2015, 12 pages.
Non-Final Office Action dated Jan. 26, 2018, for U.S. Appl. No. 14/625,540, filed Feb. 18, 2015, 15 pages.
Non-Final Office Action dated Feb. 12, 2018, for U.S. Appl. No. 15/203,652, filed Jul. 6, 2016, 9 pages.
Final Office Action dated Aug. 30, 2018, for U.S. Appl. No. 15/203,652, filed Jul. 6, 2016, 11 pages.
Notice of Allowance dated Nov. 20, 2018, for U.S. Appl. No. 15/203,652, filed Jul. 6, 2016, 8 pages.
Final Office Action dated Nov. 23, 2018, for U.S. Appl. No. 14/928,838, filed Oct. 30, 2015, 10 pages.

\* cited by examiner

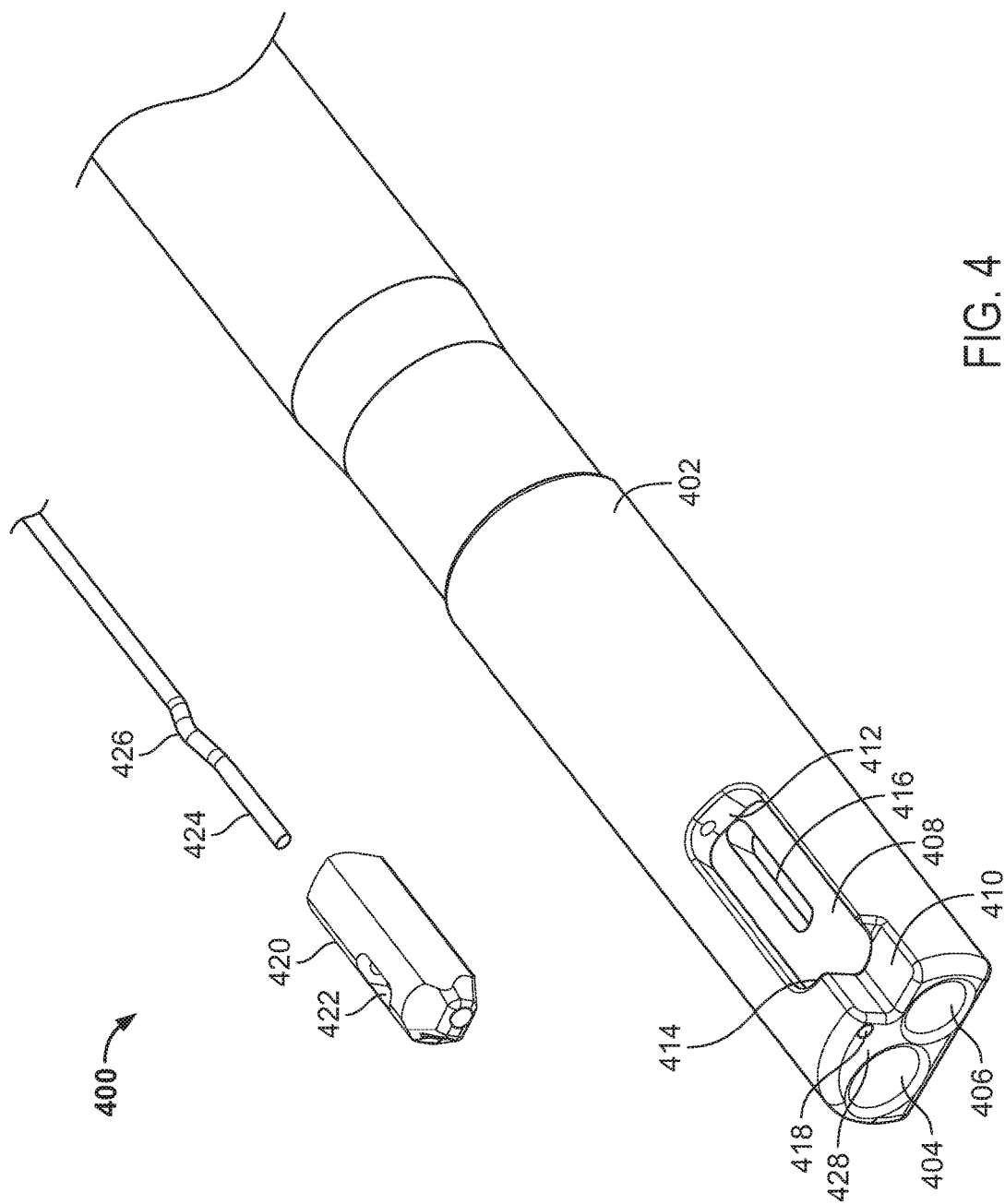

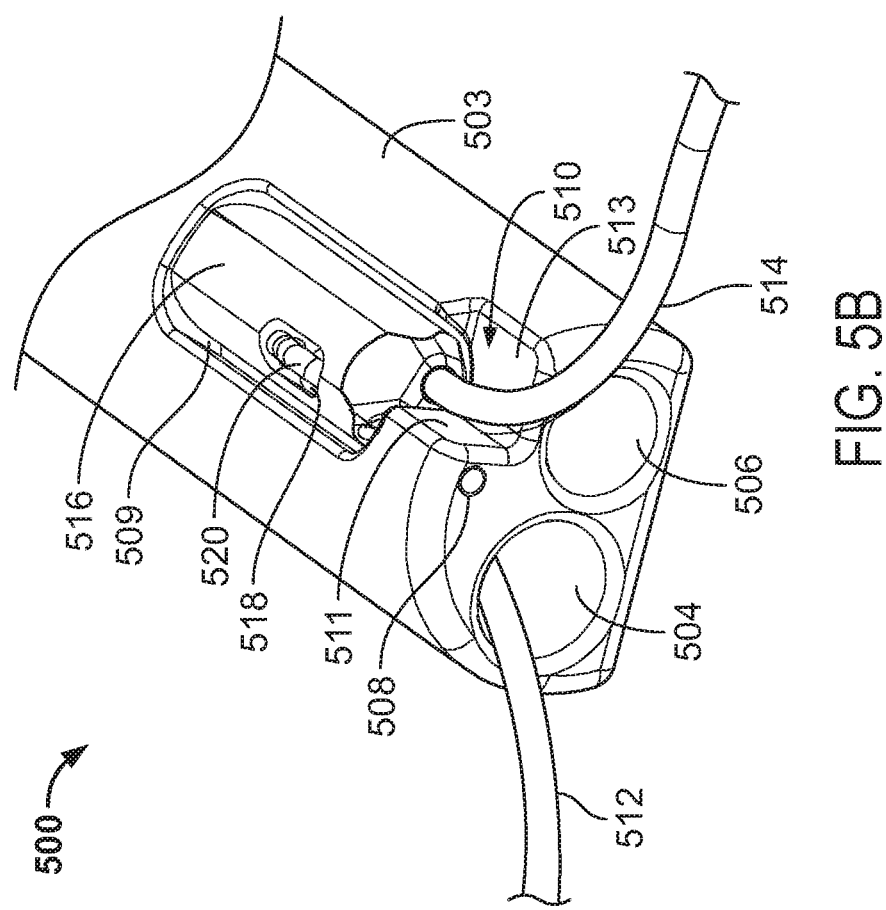

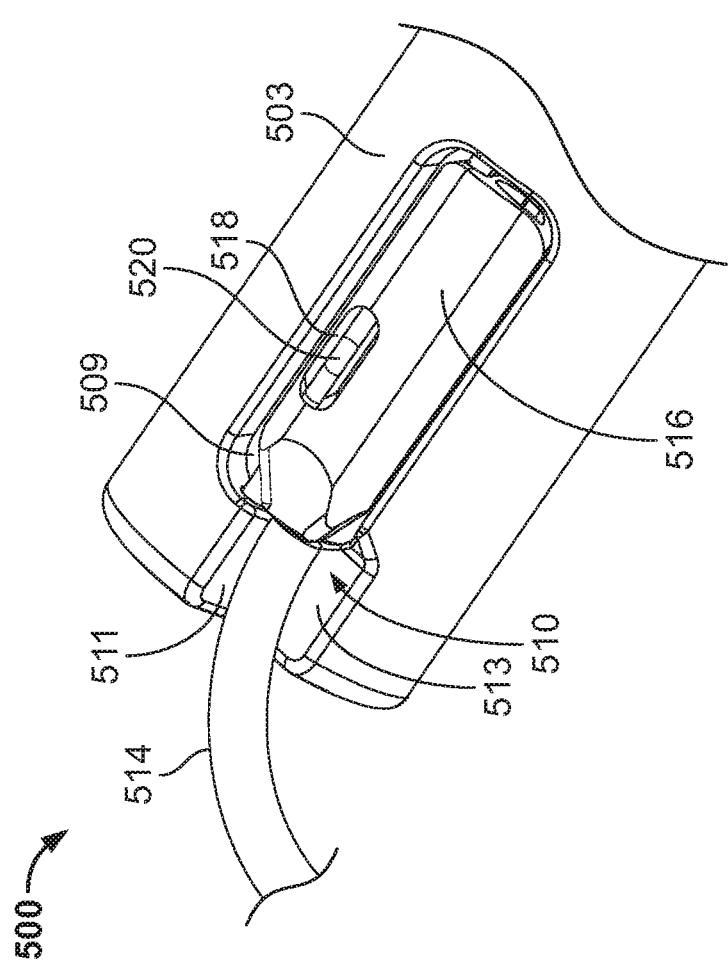

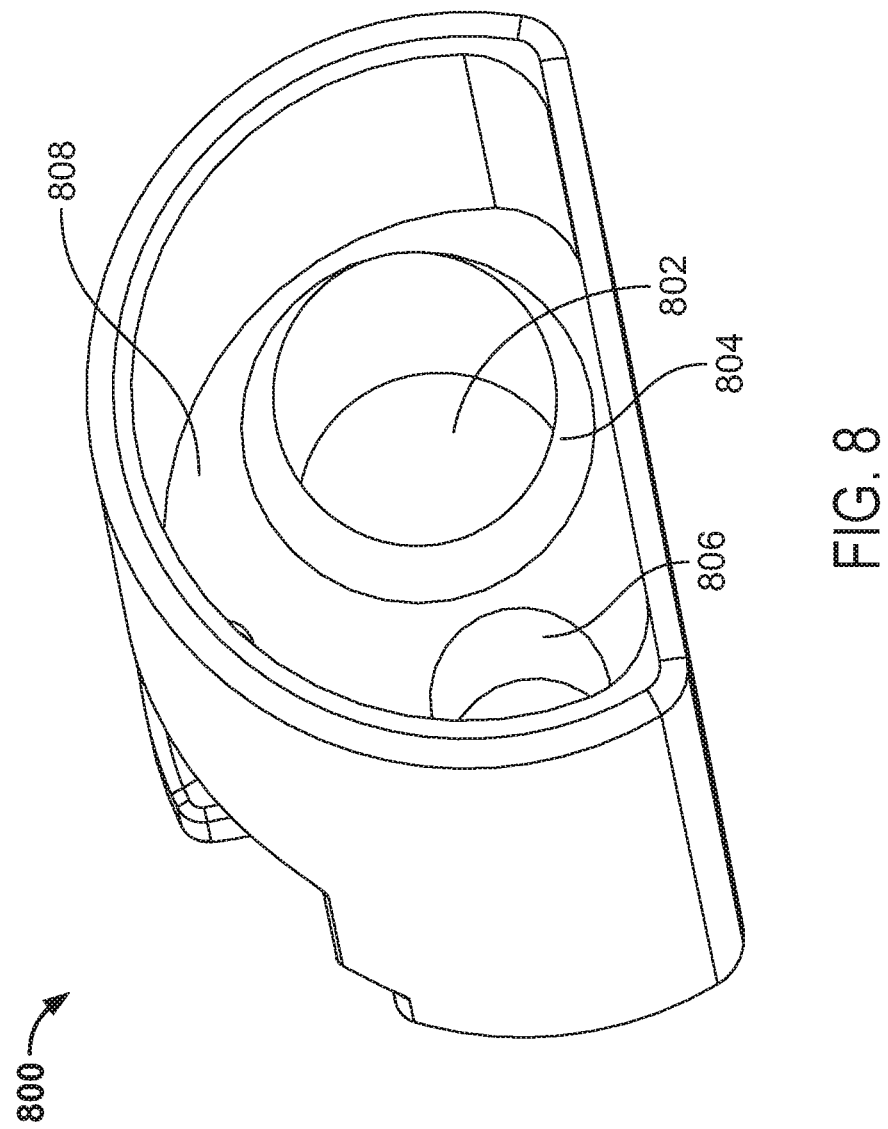

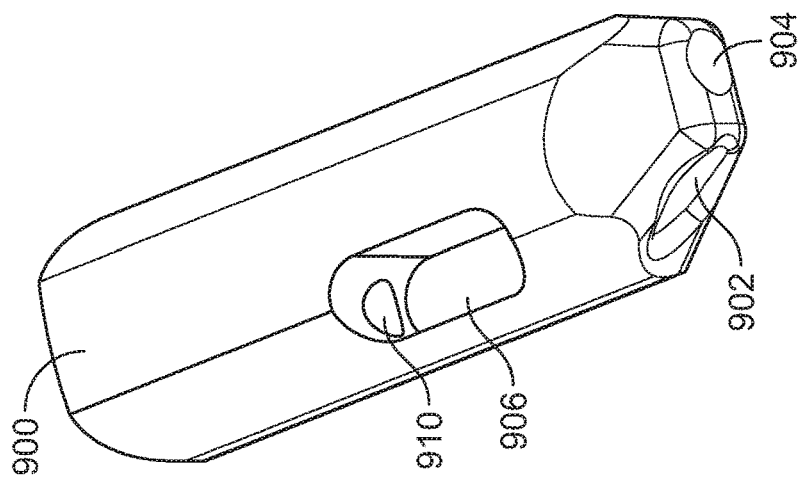
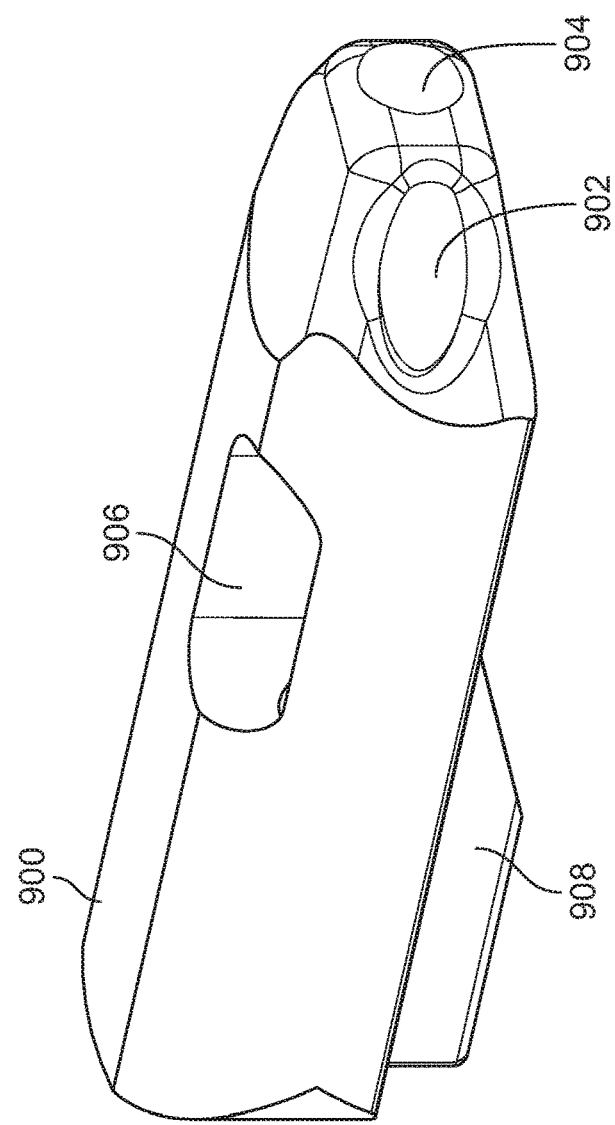
FIG. 9B
FIG. 9A

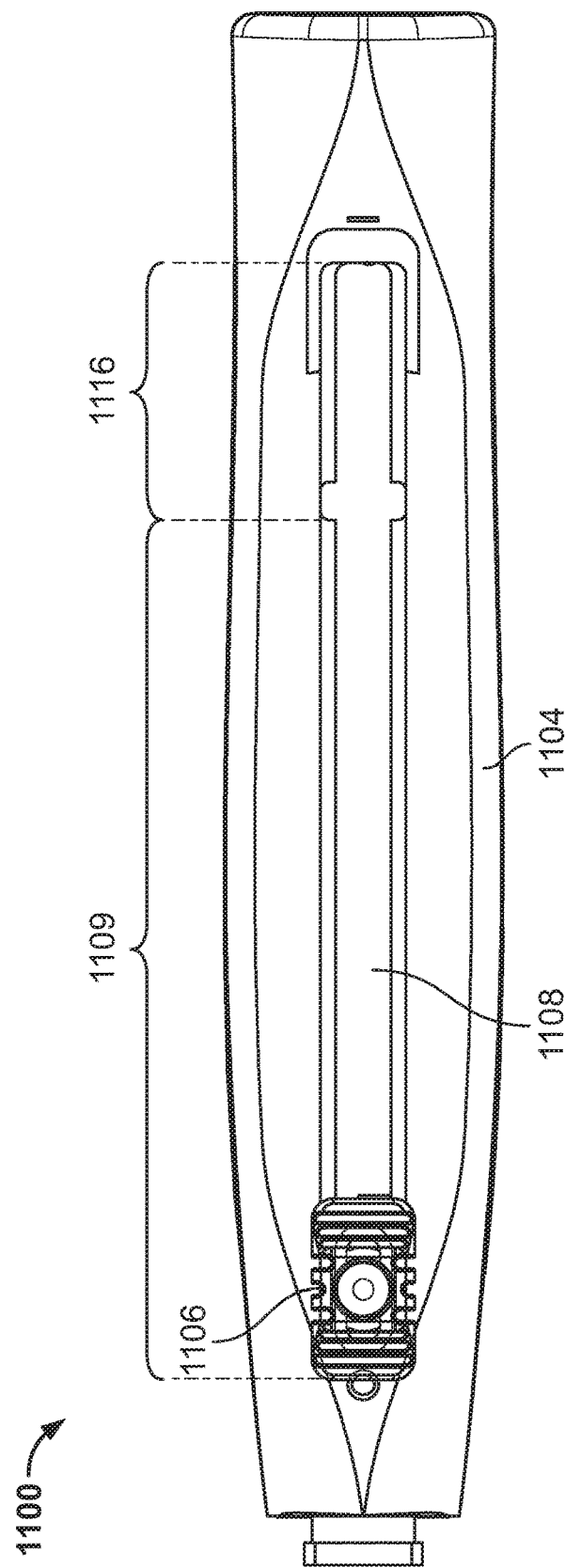

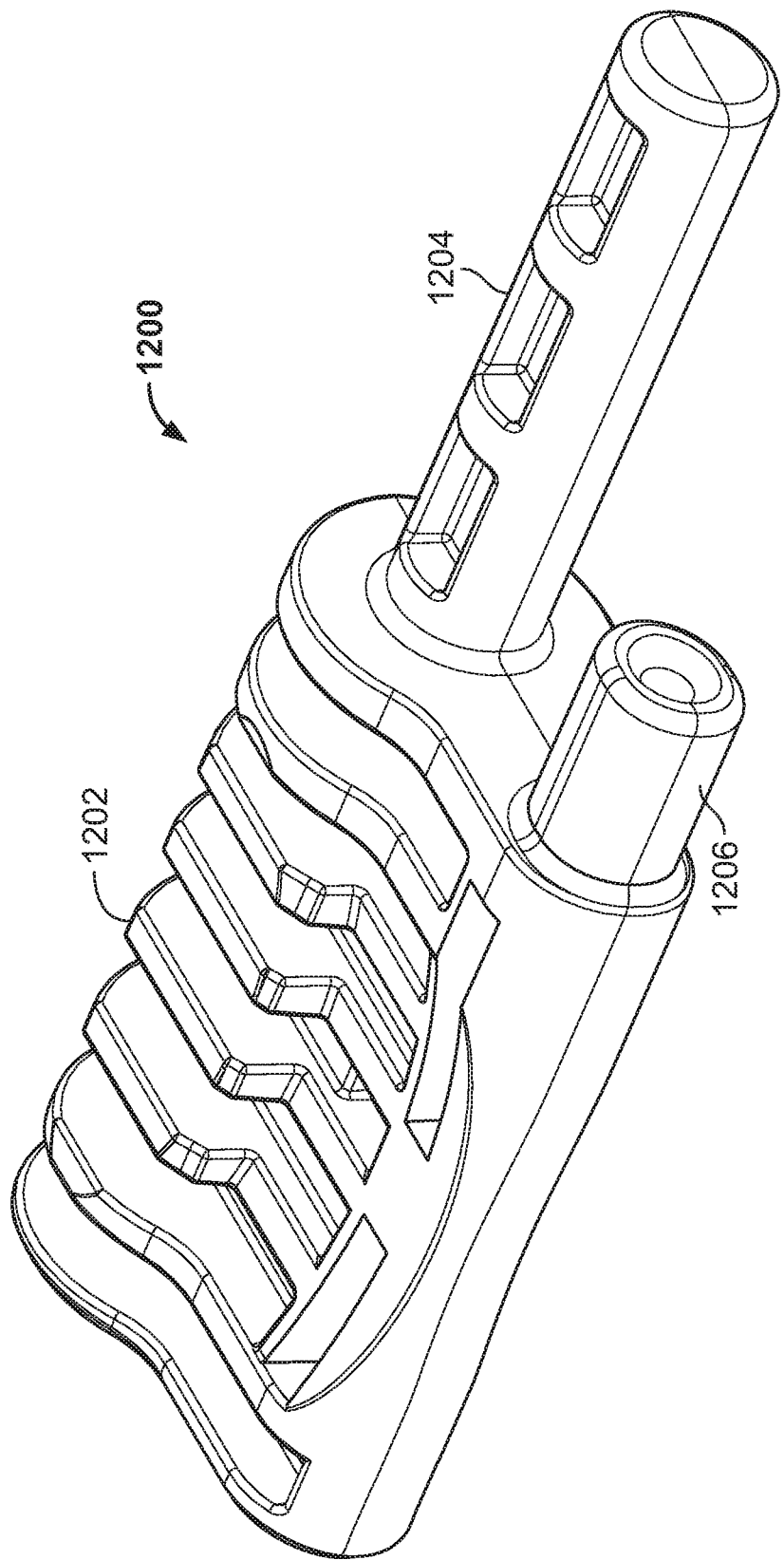

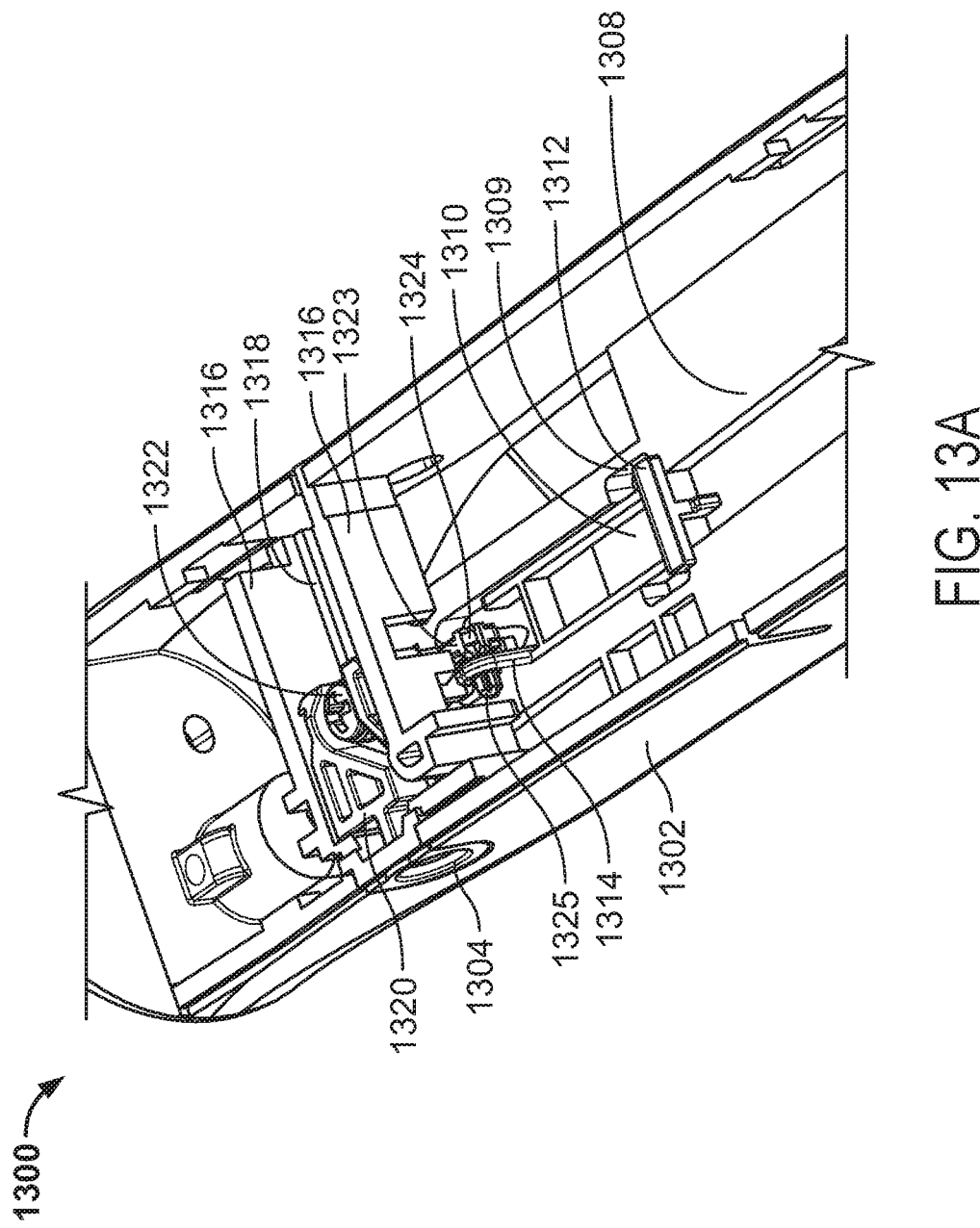

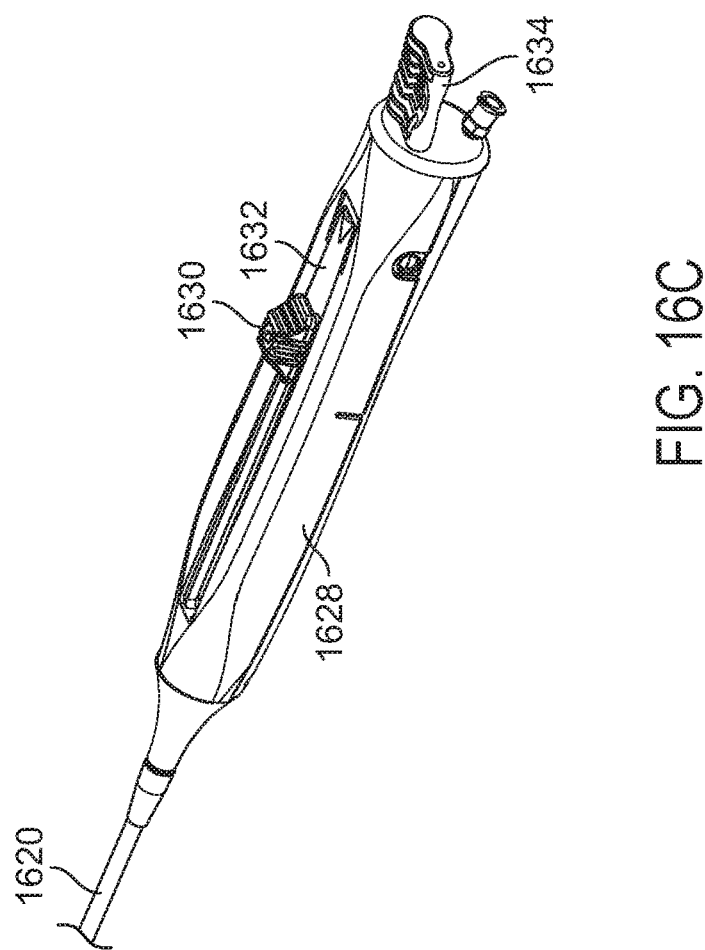
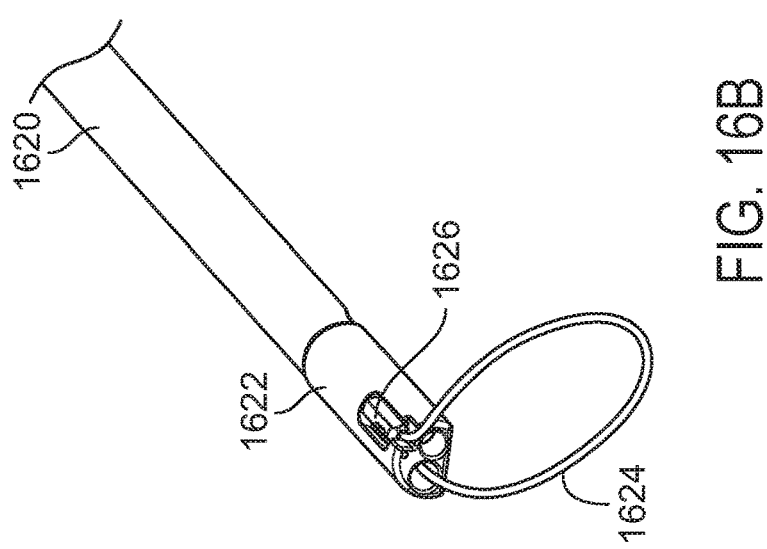
FIG. 16C
FIG. 16B

DEVICES AND METHODS FOR LEFT ATRIAL APPENDAGE CLOSURE

CROSS-REFERENCE TO RELATED APPLICATIONS

This application claims priority to U.S. Provisional Application No. 62/300,608, filed Feb. 26, 2016 and titled "DEVICES AND METHODS FOR LEFT ATRIAL APPENDAGE CLOSURE," which is hereby incorporated by reference in its entirety.

FIELD

The innovations disclosed herein relate generally to devices and methods for ligating tissue, such as the left atrial appendage, using surgically, minimally invasive, or intravascular approaches.

BACKGROUND

Atrial fibrillation is a common problem that afflicts millions of patients. Atrial fibrillation often results in the formation of a thrombus, or clot, in the appendage of the left atrium. This presents a problem, inasmuch as the thrombus can dislodge and embolize to distant organs, which may result in adverse events such as a stroke. For this reason, most patients with atrial fibrillation are treated with one or more blood thinners to help prevent the formation of a thrombus. Blood thinners, however, can present health risks of their own, especially in the elderly. These risks, such as bleeding, often require a user to make significant lifestyle changes.

Several methods have been developed to address the potential problem of thrombus formation in the left atrial appendage. One such method includes suturing the left atrial appendage along the base or ostial neck where it joins the atrial chamber. In this way, blood flow into the atrial appendage is cut off, eliminating the risk of thrombus formation therein. Other methods have also been investigated. These methods include stapling the base of the appendage and filling the appendage with a space-occupying or occluding member. Stapling is not preferred given the fragility of the appendage and its tendency to rupture, whereas occlusion devices may not effectively prevent all blood flow into the appendage.

Most of these procedures are typically performed through open-heart surgery; however, some may also be performed using minimally invasive techniques. Open-heart surgery may limit the availability of these procedures to those who are at a particularly high risk, or who are otherwise undergoing an open-heart procedure. In addition, open-heart surgery requires general anesthesia and has a number of well-known risks, which may make it less desirable for some. Therefore, additional devices and methods for closing the left atrial appendage using minimally invasive, intravascular, or a combination of these techniques would be desirable in order to avoid the need for opening the chest.

However, at times, the closure of the left atrial appendage is a concomitant procedure during other cardiac procedures, and performing the closure during an open-heart procedure may provide benefits in comparison to a minimally invasive procedure. For example, performing the closure during an open-heart procedure may make it easier for instruments to access the heart and may allow for better control or maneuverability of those instruments. Additionally, using an open-heart approach may provide a better view of the heart and the surrounding tissue during the procedure. Thus, additional devices for use in open surgical procedures are desirable, especially when those devices offer additional advantages over standard devices.

BRIEF SUMMARY

Described here are devices, systems, and methods for closing the left atrial appendage. In general, the devices described here for closing a target tissue comprise an elongate body comprising a lumen therethrough. A snare loop assembly may be provided and may comprise a snare and a suture loop releasably coupled to the snare. The snare loop assembly may extend at least partially from the elongate body. A shuttle may be connected to a distal portion of the snare and releasably coupled to the elongate body. The shuttle may comprise a configuration to fit into the lumen.

In some variations, the elongate body may comprise an approximately L-shaped recess in a side wall of the elongate body. The distal portion of the snare may be positioned in the recess when the shuttle is coupled to the elongate body.

In some instances, the device may comprise a lock wire configured to releasably couple the shuttle to the elongate body. The shuttle may comprise a snare lumen and a proximal portion of the snare lumen may comprise an offset obround.

In some variations, a distal portion of the elongate body may comprise a corner chamfer. A tip may be coupled to the distal portion of the elongate body. The tip may comprise a tip lumen and a proximal portion of the tip may comprise a tip chamfer. The tip chamfer may be 30 degrees and offset from the tip lumen.

The device may include additional features. The elongate body may comprise a shuttle recess and the shuttle may be disposed within the shuttle recess when the shuttle is coupled to the elongate body. In some variations, the device may comprise a first configuration in which the shuttle is fixedly coupled to the elongate body and a second configuration in which the shuttle is positioned within the lumen. In some instances, the shuttle may have a maximum dimension that is less than a diameter of the lumen. A diameter of the lumen of the elongate body may be equal to or less than about 1.60 mm.

In some instances, the devices described here may comprise an elongate body, a snare loop assembly, a shuttle, and a handle. The snare loop assembly may comprise a snare and a suture loop releasably coupled to the snare. The snare loop assembly may extend at least partially from the elongate body. The shuttle may be releasably coupled to the elongate body and may be connected to a distal portion of the snare. The handle may be attached to the elongate body. The handle may comprise a track, a snare control coupled to the track, and a release assembly housed within the handle. The snare control may comprise a limiter configured to limit movement of the snare control along a proximal portion of the track, and the release assembly may be configured to release the shuttle from the elongate body and disengage the limiter to allow movement of the snare control along the proximal portion of the track.

In some variations, the device may comprise a suture control for tightening the suture loop. The suture control may comprise a proximal portion configured to engage the release assembly through an opening in the handle and disengage the limiter from the release assembly. The release assembly may comprise a flexible latch configured to limit movement of the release assembly after engagement of the suture control to the release assembly. The limiter may extend along a length of the track and/or a lock wire may be configured to releasably couple the shuttle to the elongate body.

In some variations, the devices described here may comprise an elongate body, a snare loop assembly, a shuttle, and a handle comprising a lock configured to limit movement of the snare control along the track. The snare loop assembly may comprise a snare and a suture loop releasably coupled to the snare and the snare loop assembly may extend at least partially from the elongate body. The shuttle may be releasably coupled to the elongate body and may be connected to a distal portion of the snare. The handle may be attached to the elongate body and may additionally comprise a track, a snare control coupled to the track, and a release assembly configured to release the shuttle from the elongate body and allow movement of the snare control along the track.

In some of these variations, the devices may further comprise a suture control configured to tighten the suture loop. The suture control may comprise a proximal portion configured to engage the release assembly through an opening in the handle and disengage the lock from the release assembly. In some variations, the lock may comprise a stopper extending along a length of the track. The lock may further comprise a lock engagement portion comprising an opening and the opening may be releasably coupled to the release assembly. In some variations, the release engagement portion may extend from a bottom surface of the stopper. The release assembly may comprise a release engagement portion and the lock engagement portion may be releasably coupled to the release engagement portion. In some variations, the release engagement portion may comprise a base and a protrusion, and the protrusion may be configured to fit within the opening of the lock to releasably couple the lock engagement portion and the release engagement portion. In some instances, the lock may further comprise an end plate. Additionally, in some variations, the device may comprise a lock wire configured to releasably couple the shuttle to the elongate body.

Also described here are methods of closing a target tissue. In general, the methods may comprise advancing a device towards the target tissue. The device may comprise an elongate body, a snare loop assembly comprising a snare and a suture loop, and a shuttle connected to the snare and releasably coupled to the elongate body. The snare loop assembly may be closed around the target tissue. The suture loop may be released from the snare loop assembly. The shuttle may be released from the elongate body. The shuttle may be retracted into a lumen of the elongate body. The suture loop may be tightened around the target tissue. Methods may also comprise withdrawing the device from the body.

In one variation, shuttle retraction may be performed prior to tightening the suture loop. In some instances, the method may further comprise opening the closed snare loop assembly. Tightening of the suture loop may be performed prior to releasing the shuttle from the elongate body. Tightening of the suture loop may be performed after opening the closed snare loop assembly. In some variations, opening the closed snare loop assembly may further comprise bending the distal end portion of the snare freely away from the elongate body. In some variations, a maximum shuttle diameter may be less than a diameter of the lumen of the elongate body. In some instances, the device may further comprise a handle attached to the elongate body and the handle may comprise a track, a snare control coupled to the track, and a lock configured to limit movement of the snare control along the track. The handle may further comprise a release assembly configured to release the shuttle from the elongate body and allow movement of the snare control along the track. In some of these instances, the track may comprise a first portion and a second portion, and the lock may limit movement of the snare control along the second portion of the track.

The methods may include additional variations. In some variations, the suture loop may be tightened via a suture control. In some of these variations, the device may further comprise a handle coupled to the elongate body and retracting the shuttle may further comprise inserting a portion of the suture control through an opening in the handle, engaging a release assembly with the inserted portion of the suture control, and disengaging a lock from the release assembly. In some of these variations, the handle may comprise a snare control and a track with a first portion and a second portion, and retracting the shuttle may further comprise removing the lock from a second portion of the track and moving the snare control along the second portion of the track.

In further variations of the methods, the snare control may comprise a limiter configured to limit movement of the snare control along the track. A release assembly may be configured to release the shuttle from the elongate body and allow movement of the snare control along the track. The track may comprise a first portion and a second portion, and the limiter may be a lock configured to limit movement of the snare control along the second portion of the track.

BRIEF DESCRIPTION OF THE DRAWINGS

FIG. 4 is an exploded perspective view of a variation of a closure device.

FIGS. 5A and 5B are perspective views of a variation of a closure device having a retractable snare. FIG. 5C is a top view of the closure device shown in FIG. 5A.

FIG. 8 is a perspective view of a proximal end of a tip of a closure device.

FIGS. 9A and 9B are perspective views of a variation of a shuttle for a retractable snare.

FIG. 11C is a top view of the handle assembly shown in FIG. 11B.

FIG. 12 shows a perspective view of a suture control for use with a handle assembly.

FIGS. 13A-13B are cross-sectional perspective views of a variation of a handle assembly of a closure device.

FIGS. 16B-16G are perspective views of a snare loop assembly and handle assembly corresponding to FIG. 16A.

DETAILED DESCRIPTION

Figure 1:
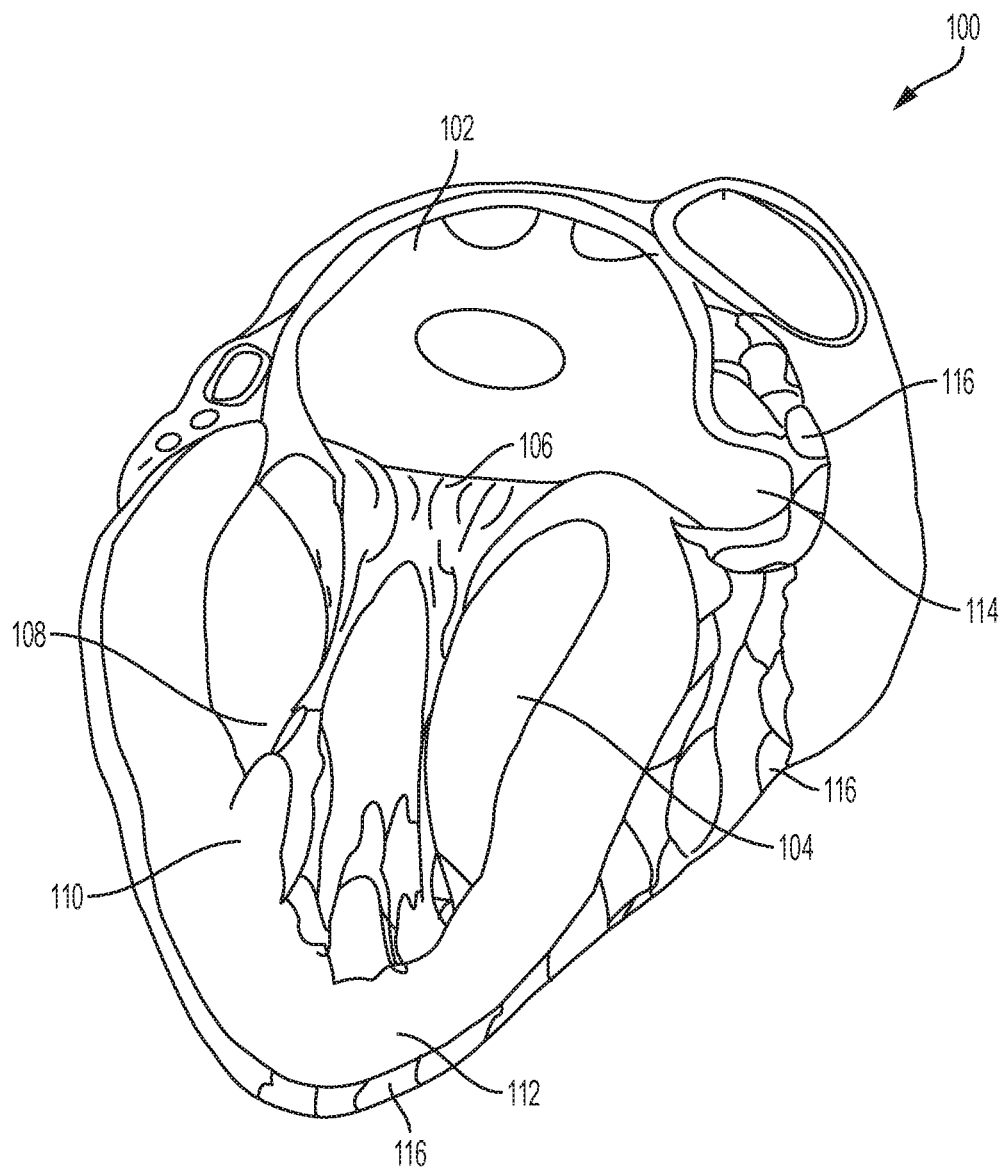
FIG. 1 provides a cross-sectional representation of a heart showing various anatomical structures.

Described here are devices, systems, and methods for closing tissue, for example, the left atrial appendage. In instances where the heart is the relevant anatomy, it may be helpful to briefly identify and describe the relevant heart anatomy. FIG. 1 is a cross-sectional view of the heart (100). Shown there are the left atrium (102) and the left ventricle (104). In between the left atrium (102) and the left ventricle (104) is the mitral valve (also known as the bicuspid valve), which is defined by a pair of mitral valve leaflets (106). The leaflets are connected to chordae tendinae (108) that are connected to papillary muscles (110). The papillary muscles join the ventricular wall (112). The left atrial appendage (114) is shown adjacent to, and is formed from, the wall of the left atrium (102).

As can be seen, the left atrial appendage (114) lies within the boundaries of the pericardium (116) and is in close proximity to the ventricular wall (112). The left atrial appendage typically has a tubular shape that approximates a cone, with a slight narrowing or neck in the plane of the orifice where it joins the left atrium (102). In patients with atrial fibrillation, the left atrial appendage (114) is the most common location for thrombosis formation, which, in time, may dislodge and cause a devastating stroke. Because stroke is the primary complication of atrial fibrillation, the left atrial appendage is frequently excluded from the left atrium in those patients undergoing procedures to treat atrial fibrillation, and is often removed or excluded at the time of other surgical procedures, such as mitral valve surgery, to reduce the risk of a future stroke. The devices and systems described here help ensure proper closure of the left atrial appendage at the neck or base of the left atrial appendage, along the anatomic ostial plane. In this way, exclusion of the entire left atrial appendage from systemic circulation may be facilitated.

I. Devices

Described here are closure devices and methods for closing tissues using these closure devices. Generally, the closure devices comprise an elongate body and a snare loop assembly that may extend at least partially from the elongate body to capture and hold tissue. The snare loop assembly typically comprises a closure element, for example, a snare, and a suture loop releasably coupled to the snare. The snare loop assembly may be closed around tissue to temporarily or permanently close, ligate, or otherwise tighten tissue, and the suture loop may be tightened and released from the snare to hold or otherwise maintain the tissue in the closed configuration. Either before or after the suture loop is tightened, the snare loop assembly may be retracted into the elongate body to facilitate the removal of the closure device from confined body spaces. The closure device may include one or more mechanisms that prevent premature retraction of the snare loop assembly.

Figure 2:
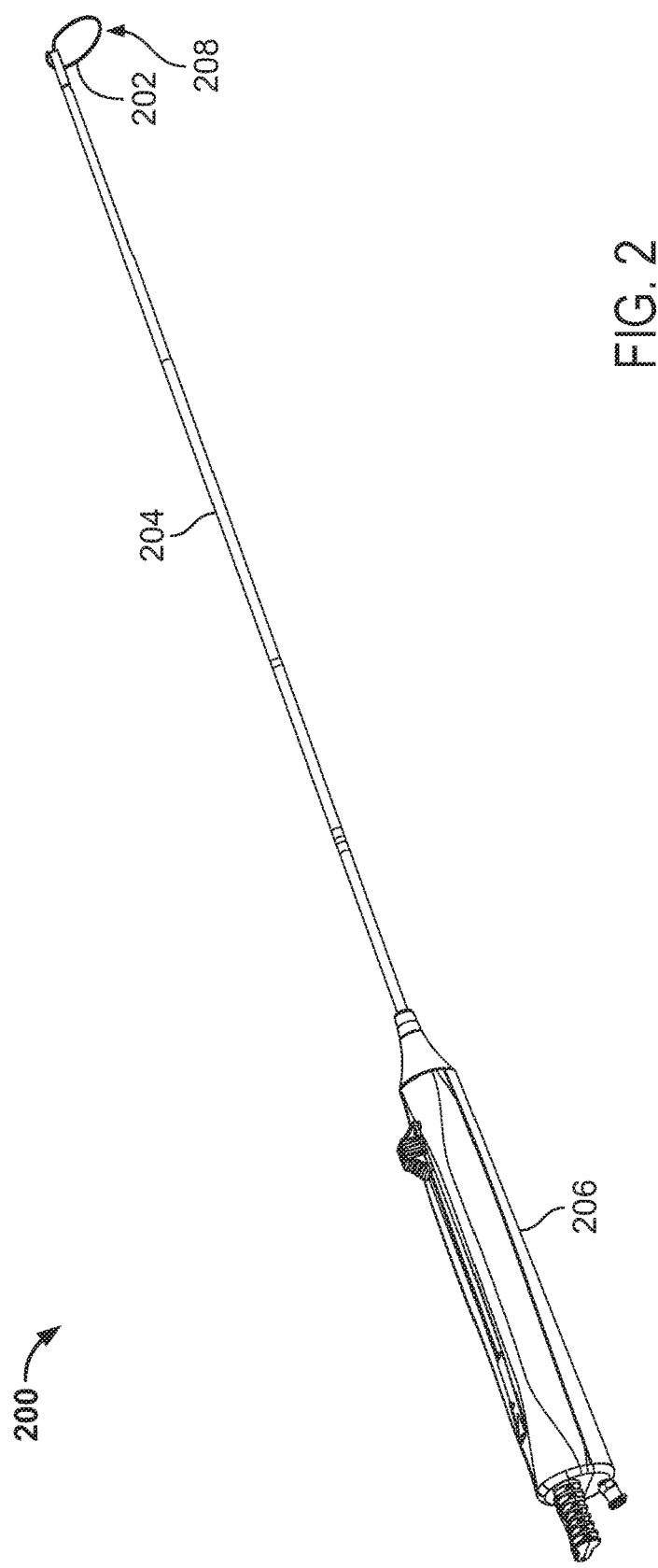
FIG. 2 is a perspective view of an illustrative closure device that may be used to close the left atrial appendage.

FIG. 2 depicts one illustrative variation of closure device (200) that may be used to close the left atrial appendage. Shown there are a snare loop assembly (202), an elongate body (204), and a handle (206). As noted above, the handle (206) may be used to control and actuate the snare loop assembly (202) through the elongate body (204) in order to move snare loop assembly (202) between a closed configuration, an open deployed configuration, and a retracted configuration. When in an open configuration, the snare loop assembly (202) and elongate body (204) may form a continuous loop (208) (e.g., such that the snare loop assembly (202) and the elongate body (204) may fully encircle tissue placed in the loop (208)). When moved from the open configuration to the closed configuration, the size of the loop (208) may be reduced as some or all of the snare loop assembly (202) is withdrawn into the elongate body (204). Finally, in the retracted position, the loop (208) (e.g., a snare and a retention member) may be provided entirely within the elongate body (204). Alternatively, in the retracted position, a substantial portion of the loop (208) may be provided within the elongate body with a small portion of the loop (208) remaining outside of the elongate body (204).

The closure devices described here may be suitable for advancement to the left atrial appendage using minimally invasive (e.g., through a small incision above, beneath, or through the rib cage, through an incision in the costal cartilage or the xiphoid, through a port, through the vasculature, and the like) and surgical (e.g., median sternotomy, mini sternotomy, thoracotomy, thoracoscopy, and the like) approaches.

Figure 3A:
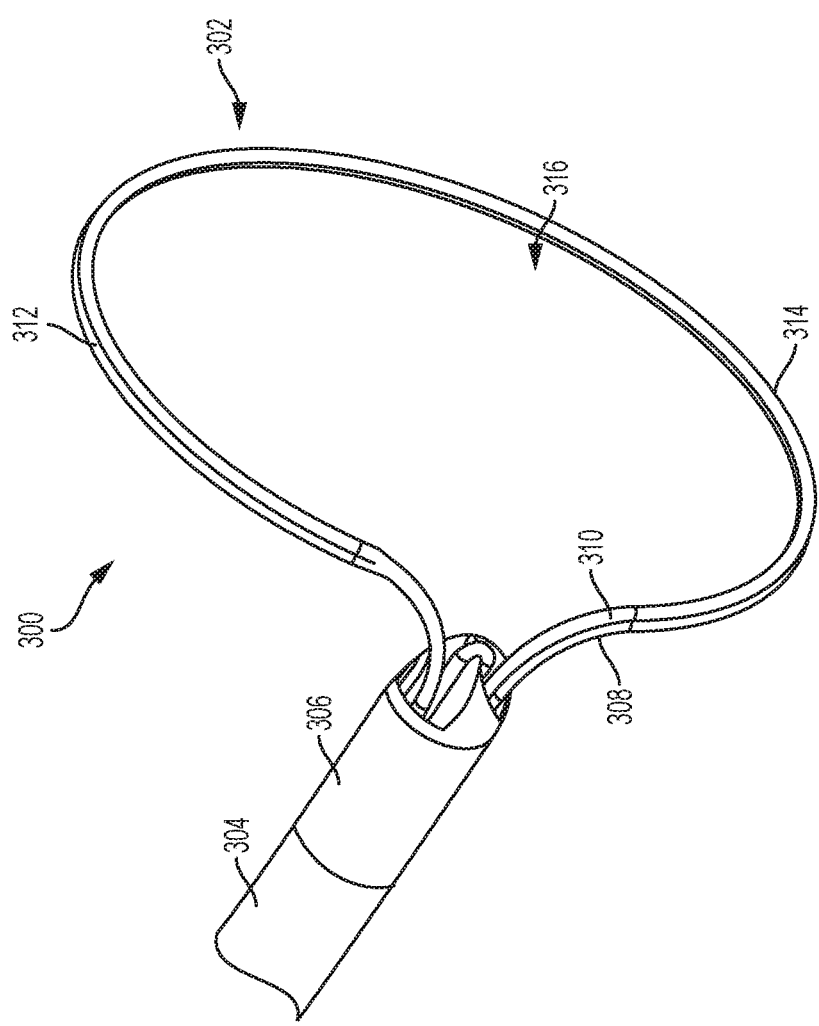
FIG. 3A is a view of a distal end of an illustrative variation of a closure device having a snare loop assembly.

FIG. 3A shows a distal section of an illustrative variation of a closure device (300) comprising a snare loop assembly (302) and an elongate body (304) having tip (306). As shown there, the snare loop assembly (302) may comprise a snare (308), a suture loop (310), and a retention member (312), and may be disposed relative to the elongate body (304) such that at least a portion of the snare loop assembly (302) extends from the elongate body (304) (e.g., via tip (306)). The snare loop assembly (302) is shown in FIG. 3A in an open configuration, and the portion of the snare loop assembly (302) extending out of elongate body (304) may form a loop (314) having an aperture (316) therethrough. The loop (314) and the corresponding aperture (316) may be defined by one or more components of the snare loop assembly (302) (e.g., the snare) and may be suitable for encircling tissue such as the left atrial appendage. Generally, the snare (308) may be used to open and close the snare loop assembly (302). In some instances, the retention member (312) may be configured to releasably couple the suture loop (310) and the snare (308) and may be configured to release the suture loop (310) from the snare loop assembly (302) upon application of a sufficient force to suture loop (310).

Figure 5A:
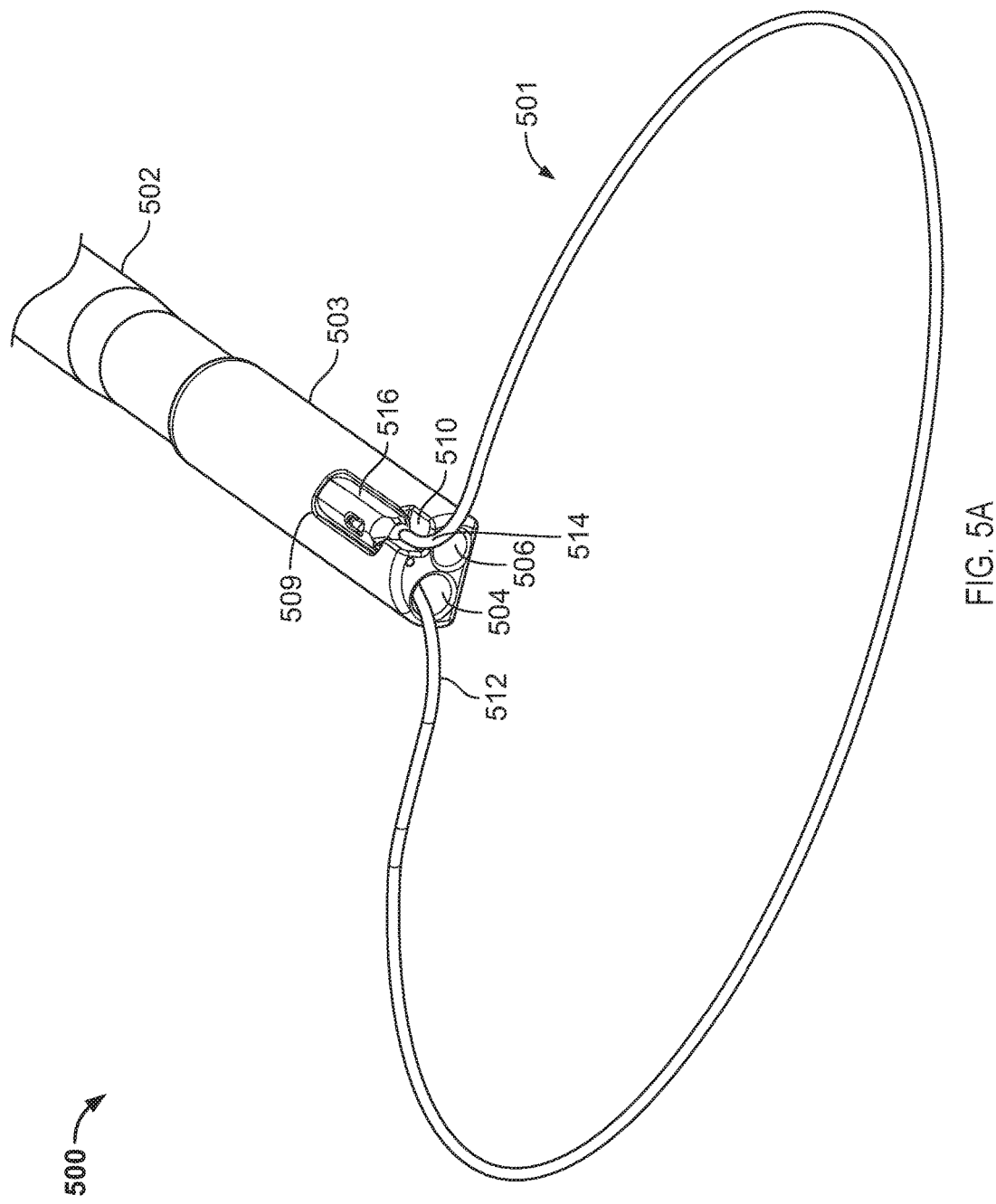

A snare loop assembly may further comprise a shuttle to allow a distal portion of a snare loop to be released from a tip of the elongate body to allow the snare loop to be retracted into a lumen of the tip. Retraction of the snare loop into the tip reduces a profile of the device to improve removal of the device from a body. For example, retraction of the snare into the elongate body may prevent the snare from catching on and/or damaging tissue when the device is removed from the body after the shuttle is released from the tip. The shuttle may function to releasably connect the snare loop to the tip. A user may control the release of the shuttle through the handle. FIG. 5A is a perspective view of a closure device (500) having an elongate body (502) comprising a tip (503), a shuttle (516), and a retractable snare comprising a proximal portion (512) and a distal portion (514). The shuttle (516) may be connected to the distal portion (514) of the snare and releasably coupled to the tip (503) of the elongate body (502). While depicted comprising a tip (503), the elongate body (502) need not. In variations in which a tip is not used, the shuttle may be coupled to a side wall of the elongate body (e.g., at a distal portion or end of the elongate body).

When the closure devices are advanced through confined body spaces, such as the pericardial space, advancement or manipulation of the snare loop assembly within or through these tight spaces may result in portions of the snare, such as an end of the snare protruding from the elongate body, to curve and bend to a greater degree than other portions of the snare. To form a snare loop, the snare may curve as it leaves a tip of the elongate body. A curve of the snare may induce a shift or tilt in components connected to the snare relative to the elongate body due to friction of the snare against the tip.

For instance, a conventional shuttle connected to the snare may shift or tilt upward out of a recess of a tip due to the forces generated by a curve of the snare. An uneven interference is thus generated where the curved portion of the snare contacts a sidewall of the tip. Consequently, frictional forces may create misalignment of the shuttle with the tip, which may make assembly and operation of the device difficult. Additionally, in some instances, bending or manipulation of the snare loop assembly within a confined space may create undesirable interference from tissue that may become pinched between the snare and the tip. Accordingly, devices described herein may be configured to allow the snare to bend freely without rubbing or abutting against the elongate body, which may reduce interference, misalignment and tissue pinching.

Additionally, a conventional snare loop may be releasable in that a distal portion of the snare loop may be detached from the tip to allow for easier removal of the snare loop from around the tissue disposed within the loop. However, after releasing a distal portion of the snare loop, the portion of the snare that was encircling the tissue and a shuttle remain exposed and external to the elongate body. This exposed portion of the snare and the shuttle may interact with and catch onto anatomical features or the suture as the closure device is moved away from the target tissue. Accordingly, devices described herein below may be configured to allow the snare and the shuttle to fully retract into the elongate body such that no portion of the snare or shuttle remains exposed. In other variations, the devices described herein may be configured to allow almost the entire snare loop (e.g., a majority of the snare loop exposed during a procedure, ⅔ of the exposed snare loop, ⅚ of the exposed snare loop, and the like) and thus the snare to retract into the elongate body such that the shuttle and a small portion of the snare remains outside the elongate body.

In addition to having an elongate body and a snare loop assembly, closure devices described here typically comprise one or more mechanisms for controlling manipulation and advancement of the elongate body and/or the snare loop assembly. For example, a handle or other control mechanism (e.g., a surgical master-slave robotic system) may be used to control and actuate the snare loop assembly through the elongate body. The handle or other control mechanism may change the snare loop assembly between a delivery, or "closed," configuration and a deployed, or "open," configuration, and vice versa. Additionally, the handle or other control mechanism may move the snare loop assembly into a retracted configuration.

Placing the snare loop assembly in a closed configuration may allow for a low-profile advancement of the snare loop assembly to a target location and/or may allow the snare loop assembly to close around a target tissue. Conversely, placing a snare loop assembly in an open configuration may allow the snare loop assembly to be placed around one or more target tissues and/or may allow the snare loop assembly to release one or more target tissues previously closed by the snare loop assembly. Accordingly, the devices described herein may further include a handle and/or one or more other control mechanisms to control release of the suture loop from the snare loop assembly, as well as snare release and retraction. The closure devices may further include mechanisms that prevent an operator from retracting the snare and shuttle prior to releasing the shuttle from the tip.

The closure devices may contain one or more additional features, as will be described in more detail below. In some variations, a chamfer may be added to a distal portion of the elongate body that is covered or partially covered by a tip, which may prevent the tip from cracking due to tight tolerances. In other variations, a height of the tip may be increased relative to the elongate body to reduce stress on the tip, increase clearance, and provide leeway for the elongate body to distort within the tip. The manufacturability and reliability of the closure devices are thus improved. These and other features will be described in more detail below. It should be appreciated that the closure devices described here may comprise any combination of these features and the other features described and/or incorporated by reference.

The closure devices described here may include any suitable elements or combinations of elements such as those described in U.S. patent application Ser. No. 14/195,797, entitled "Tissue Ligation Devices and Methods Therefor" and filed on Mar. 3, 2014, the contents of which are incorporated by reference herein in its entirety. Individual components of the closure devices described here will be described in more detail below.

Elongate Body

As mentioned briefly above, the closure devices described here may generally comprise an elongate body. The elongate body may connect the distal end of the snare loop assembly and the handle or actuating mechanism while still allowing for control of the snare loop assembly through the elongate body. Specifically, at least a portion of some of the snare loop assembly components may be housed within the elongate body, and may be connected to the handle through the elongate body. In some variations, at least a portion of the elongate body may be flexible, which may help facilitate navigation of the elongate body through the body.

The elongate body may generally comprise a tip at the distal end thereof. In some variations, the tip of the elongate body may be formed separately from the elongate body, and may be attached to the elongate body during assembly of the device. For example, in some variations, the tip and the elongate body may be attached by a sliding fit and/or adhesive. In other variations the tip portion may be formed integrally with the elongate body as a unitary device. The tip portion may serve a number of useful functions for the closure device. In some instances, the tip may be configured to be atraumatic, which may act to reduce the risk of damaging tissue as the proximal end of the elongate body is moved within the body. In other instances, the tip may allow certain portions of the snare to pass through a lumen of the elongate body while holding other portions in place relative to elongate body, as will be described in more detail below.

The tip may have the same number of lumens as the elongate body, but need not. Indeed, in some variations, the tip may divide one or more lumens of the elongate body into two or more sub-lumens. In other variations, the tip may alter the size or shape of one or more lumens of the elongate body.

The elongate body may comprise various sections or portions with different characteristics, for example, different diameters, cross-sectional shapes, stiffnesses, materials, and the like, which may increase the steerability and maneuverability of the closure device.

The elongate body may comprise any suitable length, and the length of the elongate body may vary depending on the type of procedure being performed. The elongate body may be made of any suitable material, for example, one or more polymers (e.g., polyether block amide, polyethylene, silicone, polyvinyl chloride, latex, polyurethane, PTFE, nylon, and the like). During a minimally invasive procedure, the elongate body may have to travel a further distance through the body to reach a target tissue than when the device is used in a surgical procedure. Thus, it may be desirable to use a longer elongate body when using the device in a minimally invasive procedure and a shorter elongate body when using the device in a surgical procedure.

Moreover, the elongate body may comprise any suitable cross-sectional shape, for example, circular, oval, D-shaped, triangular, and the like. In some embodiments, the cross-sectional shape of the elongate body may vary along its length. In some variations, the elongate body may be described as having multiple portions, each portion corresponding to a specific cross-sectional shape. For example, the elongate body may comprise a proximal portion with a first cross-sectional shape (e.g., circular) and a distal portion with a second cross-sectional shape (e.g., D-shaped). Of course, the elongate body may comprise any suitable number of portions, e.g., two, three, or four portions, and the length of each portion may be the same as or different from the other portions.

The elongate body may also comprise any suitable outer diameter, and, in some instances, the outer diameter of the elongate body may also vary along its length. For example, in instances in which the closure device is used during a minimally invasive procedure, it may be desirable to limit the outer diameter of the elongate body such that it may fit through 13-French percutaneous tubing.

The elongate body may further comprise one or more transitions connecting the portions of the elongate body comprising different diameters or different cross-sectional shapes. These transitions may have any suitable length.

Lumens

The elongate bodies described here may have any suitable number of lumens. As used herein, "lumen" may refer to any bore or passageway extending through or partially through a length of the elongate body or other portion of the closure device (e.g., through a handle). It should be appreciated that a lumen need not be entirely enclosed (i.e., the lumen may comprise one or more slots, slits, gaps, or other openings along some or all of the length of the lumen). The elongate body may comprise one, two, three, four, or five or more lumens. Some or all of the lumens may extend entirely through the elongate body (i.e., from the proximal end of the elongate body to the distal end of the elongate body). Other lumens may pass through only a portion of the elongate body (e.g., from one end to an intermediate point along the elongate body, or between two intermediate points along the elongate body).

The various components of the snare loop assembly may be housed within any lumen or lumens of the elongate body. For example, in some variations, all of the components of the snare loop assembly may be housed in a single lumen. In other variations, different portions of the snare loop assembly may be at least partially housed in different lumens. For example, the free end of the suture loop may pass to the handle through a first lumen, while the free end of the snare may pass to the handle through a second lumen. In some variations, there may be excess suture housed within the elongate body, and this excess suture may be housed in any suitable lumen. For example, the excess suture may be held in the same lumen as the free end of the suture loop, in the same lumen as the free end of the snare, or in an altogether different lumen.

While the lumens shown herein are depicted in specified locations within the elongate body, the lumens may be positioned in any location within the elongate body (i.e., their centers may be moved and their locations shifted); however, it may be desirable to maintain a minimum wall thickness between the lumens to prevent breakthrough. For example, in some variations, it may be necessary to heat the elongate body after it is extruded or otherwise manufactured to attach, insert, or bond with other elements to the closure device. Heating the elongate body may cause the lumens to shift locations or change in size. In some instances, a portion of the material separating the two lumens may sever such that the lumens converge or otherwise come together forming one lumen instead of two.

In order to decrease the likelihood of this breakthrough, it may be desirable to maintain a minimum distance between the lumens during extrusion and/or heating. Additionally, as described above, in some variations, a portion of the elongate body may comprise a D-shaped cross-section, which may be created by cutting, shaving, skiving, or otherwise removing a portion of the elongate body. In these variations, maintaining a minimum wall thickness between the lumens may prevent the lumens from shifting during heating and becoming severed when the elongate body is cut to create the D-shape. Accordingly, in some variations, it may be desirable to maintain at least about a 0.005" (0.127 mm) wall thickness between the lumens.

Additionally, in some variations, the lumens may comprise a lining or a coating designed to reduce the frictional forces between the internal surface of the lumens and the components housed within them. The small size of the lumens, their relative locations, the materials used, and the precision required to fabricate the elongate body may result in manufacturing variations (e.g., different frictional characteristics inside the lumens) between different lots and/or different manufacturers. These variations may lead to an inconsistent user experience and may result in frustration with the closure device and/or improper usage. For example, if the frictional forces between the internal surface of the suture lumen and the suture vary, the user may be required to apply different amounts of force to tighten the suture each time the device is used. This may result in over or under tightening of the suture around the tissue. Accordingly, in some embodiments, the suture lumen may comprise a friction-reducing lining or coating (e.g., a polytetrafluoroethylene (PTFE)). It may be desirable to include a friction-reducing lining in any and/or all of the lumens of the elongate body, as doing so may result in a more consistent and predictable user experience.

Tip

Figure 6A:
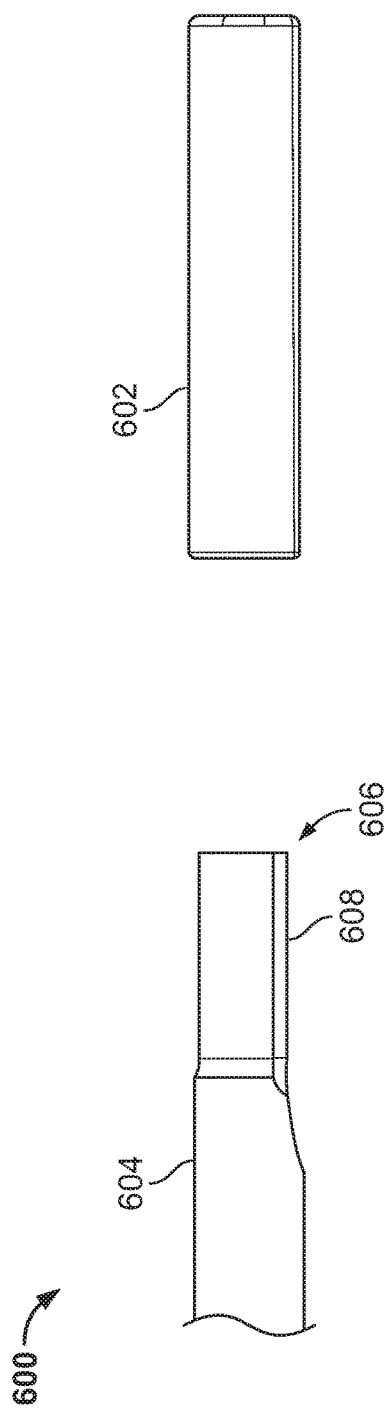
FIG. 6A is a side view of a variation of an elongate body and tip of a closure device.
Figure 6B:
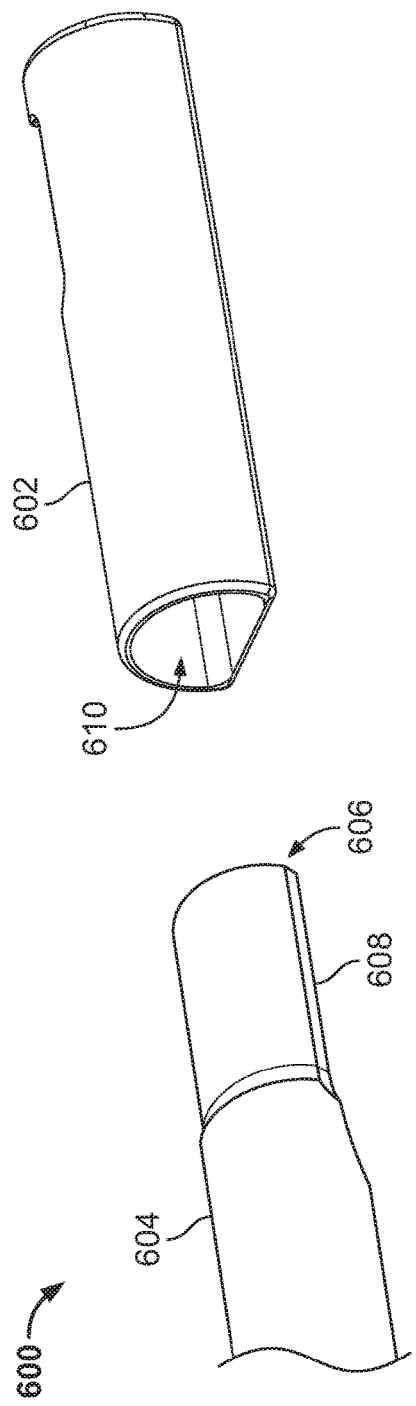
FIG. 6B is a perspective view of the elongate body and tip shown in FIG. 6A.

In some variations, the tip of the elongate body may be formed separately from the elongate body and the tip may be coupled to the elongate body by sliding the tip over the distal end of the elongate body. FIGS. 6A and 6B are side and perspective views of a variation of an elongate body (604) and a tip (602) of a closure device (600). In this variation, the tip (602) and the elongate body (604) are configured to provide a sliding fit where the elongate body (604) is secured within a cavity (610) of the tip (602). The distal end portion (606) of the elongate body (604) may comprise a corner chamfer (608), which may help prevent the tip (602) from cracking or becoming damaged by removing a contact point between the distal end portion (606) of the elongate body (604) and the tip (602) where stress may concentrate.

In one particular variation, the outermost diameter of the elongate body (604) may be 0.148 inches±0.002 inches (3.7592 mm±0.0508 mm), the height of the distal end (606) may be 0.096 inches±0.002 inches (0.24384 mm±0.0508 mm), an inside diameter of the tip (602) defining the tip cavity may be 0.148 inches+0.002/−0.001 inches (3.7592 mm+0.0508/−0.0254 mm), and an inside height of the tip may be 0.099 inches±0.002 inches (2.5146 mm±0.0508 mm).

In some variations, a gap or clearance may be formed between an external surface of the elongate body and an internal surface of the tip (i.e., a surface of the cavity) once the distal end portion of the elongate body is placed within the cavity of the tip. The gap or clearance formed between the elongate body and the tip may assist in providing a consistent and reliable fit between the elongate body and the tip, and may lower stress on the tip by providing more space for the elongate body to distort within the tip. In some variations, the gap or clearance may be formed by increasing an inner (and in some variations, an outer diameter) of the tip, while in other variations, for example those in which a D-shaped tip is used, the diameter of the tip may remain constant while the height of the tip may be increased.

Figure 7A:
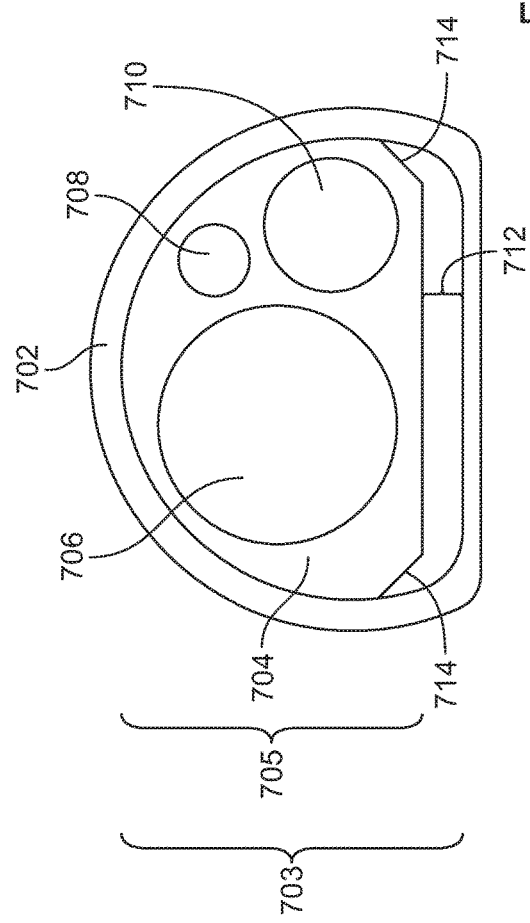
FIGS. 7A and 7B are cross-sectional views of a variation of an elongate body and tip of a closure device.
Figure 7B:
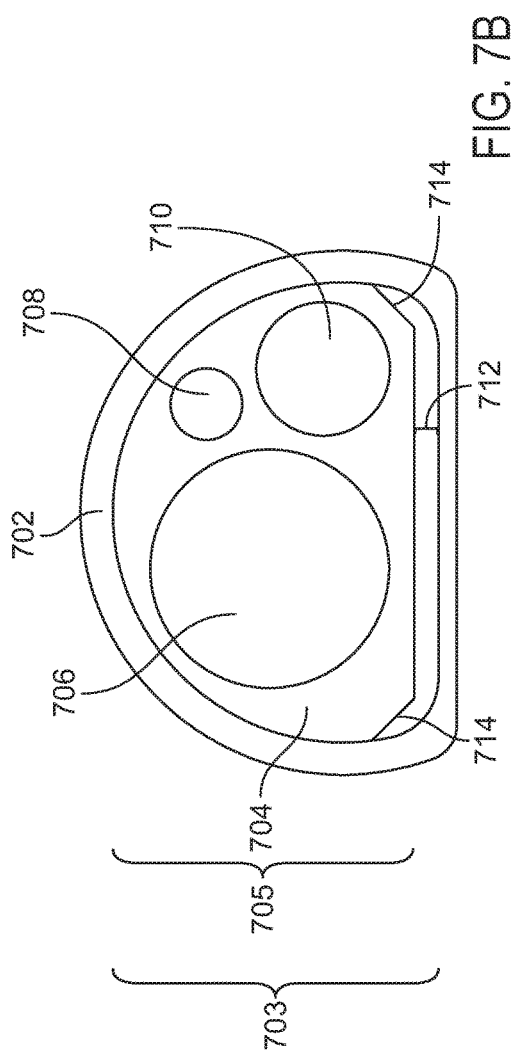

FIGS. 7A and 7B are cross-sectional views of a variation of an elongate body (704) positioned within a cavity of a tip (702). As shown in FIGS. 7A and 7B, the tip (702) and the elongate body (704) may have a clearance (712) between them. The elongate body (704) may comprise a first lumen (706), a second lumen (708), a third lumen (710), and corner chamfers (714). The tip (702) and at least a portion of the elongate body (704) (e.g., a distal portion) may have a D-shaped cross-sectional shape, each with a height (703, 705). In some variations, the height (703) of the tip (702) may be larger than a height (705) of the distal portion of the elongate body (704) such that the clearance (712) is formed between the tip and the elongate body (e.g., between the flat or linear bottom surfaces of the tip (702) and the elongate body (704)). The tip may have any suitable height, however, it may be useful to size and configure the tip so that it does not interfere with other components that may be used with the closure device during a closure procedure, for example, a guidewire and/or a guide/delivery cannula. For example, in some variations, the height of the tip may be selected such that the tip and a guidewire may fit (e.g., stacked) within a lumen of a delivery cannula. Thus, in some variations, the height and thickness of the tip combined with the diameter of the guidewire may be less than a diameter of a lumen of a delivery cannula, for example, a 13 French delivery cannula having a lumen diameter of about 0.174 inches.

For example, in some variations, it may be useful to utilize a tip (702) with an external height in a range of about 0.115 inches (2.921 mm) to about 0.125 inches (3.175 mm). Additionally, as mentioned above, the diameters/heights of the tip and the distal end of the elongate body may be selected such that a suitable gap or clearance is created between them, for example, a clearance between about 0.001 inches (0.0254 mm) and about 0.012 inches (0.305 mm). For example, in some variations, the external height of the tip may be about 0.120" (3.048 mm), the internal height (703) of the tip (702) may be about between about 0.099 inches±0.002 inches (2.515 mm±0.0508 mm) and 0.104 inches±0.002 inches (2.642 mm±0.0508 mm), and the height of the distal end of the elongate body may be between about 0.094 inches (2.388 mm) and about 0.098 inches (2.489 mm). For example, as shown in FIG. 7A, in some variations, the height (703) of the tip (702) may be about 0.106 inches (2.692 mm), which may provide a clearance (712) height of about 0.012 inches (0.330 mm) when the distal end of the elongate body (704) is positioned within the tip (702). In other variations, for example, the variation shown in FIG. 7B, the height (703) of the tip (702) may be about 0.104 inches (2.642 mm), which may provide a clearance (712) height of about 0.008 inches (0.2032 mm) relative to the elongate body (704). The foregoing are simply examples and any combination of heights of the tip and distal end of the elongate body (e.g., any combination of heights for each selected from values within the ranges contained above) that result in a clearance between about 0.001 inches (0.0254 mm) and about 0.012 inches (0.305 mm) may be used.

The front surface of the tip may also comprise one or more (e.g., two, three, four, or more) lumens, which may, but need not, correspond to the lumens of the elongate body. The tip lumens may have different diameters and/or cross-sectional shapes than one another. For example, referring to the embodiment depicted in FIGS. 7A and 7B, the tip (702) may comprise first, second, and third lumens corresponding to the first, second, and third lumens (706, 708, 710) of the elongate body. While all the lumens are depicted as having a circular cross-sectional shape, this need not be the case, and the lumens may have any suitable cross-sectional shape (e.g., oval, square, rectangular, a combination thereof, and the like). Each lumen may have a different diameter or the same diameter.

FIG. 8 depicts a perspective view of a proximal end portion of a tip (800) comprising a front surface (808) with a first tip lumen (802) having a corresponding tip chamfer (804) and a second tip lumen (806). In some instances, the tip may scuff or rub against a retention member when a snare assembly is opened and closed. However, there may be difficulty in simply increasing the diameter of the first lumen of the tip to reduce scuffing due to the space occupied by the retractable snare and the recess occupied by the shuttle. In these instances, it may be desirable to add a tip chamfer (804) to the first tip lumen (802) to reduce scuffing when the snare loop assembly is open and closed. The tip chamfer (804) may have any suitable angle, for example, it may be a 30 degree chamfer offset from center of the first tip lumen (802) or between about 20 degrees and about 60 degrees. In one variation, the diameter of first tip lumen (802) may be approximately 0.063 inches (1.60 mm).

Snare Loop Assembly

As mentioned above, the snare loop assemblies of the closure devices described here may be used to temporarily close or restrict one or more target tissues. Generally, the snare loop assembly comprises a closure element, e.g., a snare, and a suture loop releasably attached to the closure element. In some variations, the snare loop assembly may comprise a retention member at least temporarily connecting the closure element and the suture loop.

In variations of snare loop assemblies comprising a snare, the snare may be at least partially moveable to change a snare loop assembly between open, closed, and retracted configurations. Generally, a portion of the snare may be housed in the elongate body, and another portion of the snare may extend outside of the distal end of the elongate body to at least partially define the loop and aperture of the snare loop assembly.

In some variations, one end of the snare is releasably fixed relative to one or more portions of the closure device, while the other end may be advanced or retracted through the elongate body. Movement of the free end of the snare may change the amount of the snare loop assembly that is disposed outside of elongate body, and thus may change the size (e.g., diameter, circumference, area, etc.) of the loop and the aperture defined thereby. Specifically, advancement of the free end of the snare through the elongate body may increase the size of the loop and aperture of the snare loop assembly, while retraction of the free end of the snare may decrease the size of the loop and aperture of the snare loop assembly. The free end of the snare may be manipulated in any suitable manner. In some variations, the snare may be attached directly to one or more portions of the handle. In other variations, a hypotube, rod, or other rigid structure may be attached to the free end of the snare. This structure may in turn be moved by the handle, which may help facilitate advancement or withdrawal of the snare through the elongate body.

Figure 16A:
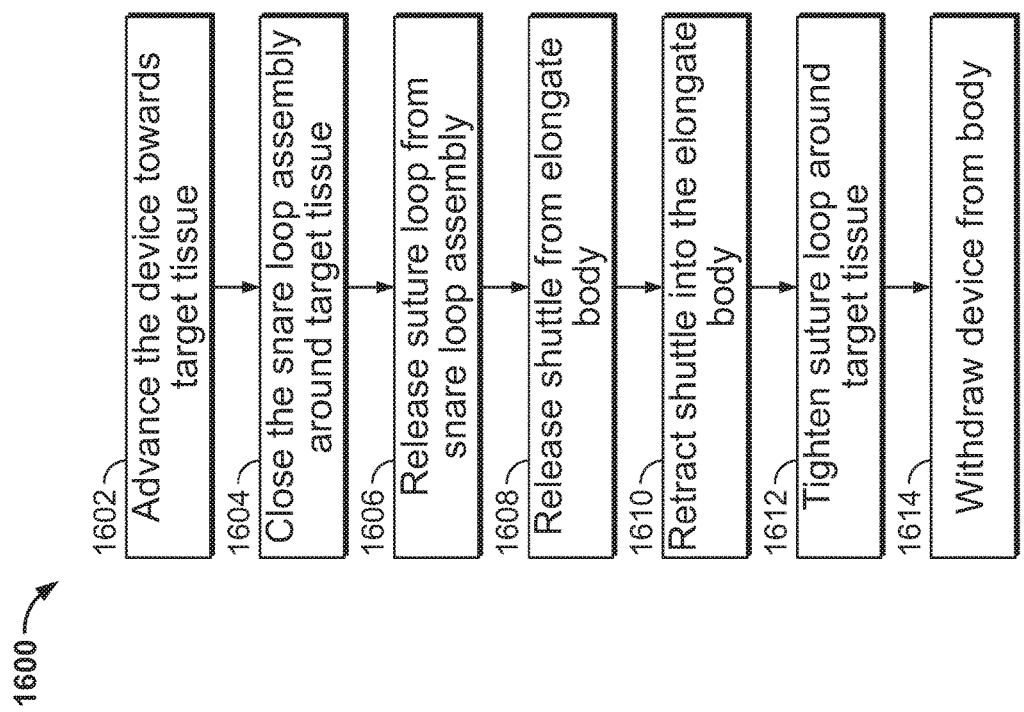
FIG. 16A is a flowchart for one variation of a tissue closing process.
Figure 16E:
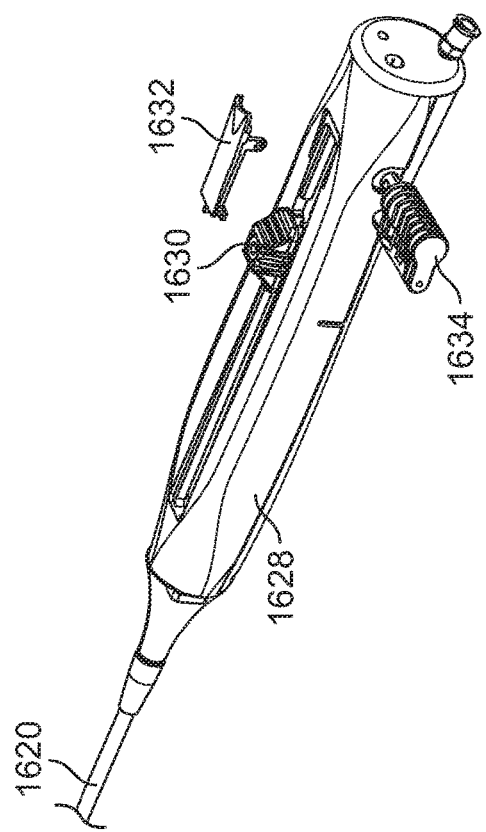
Figure 16D:
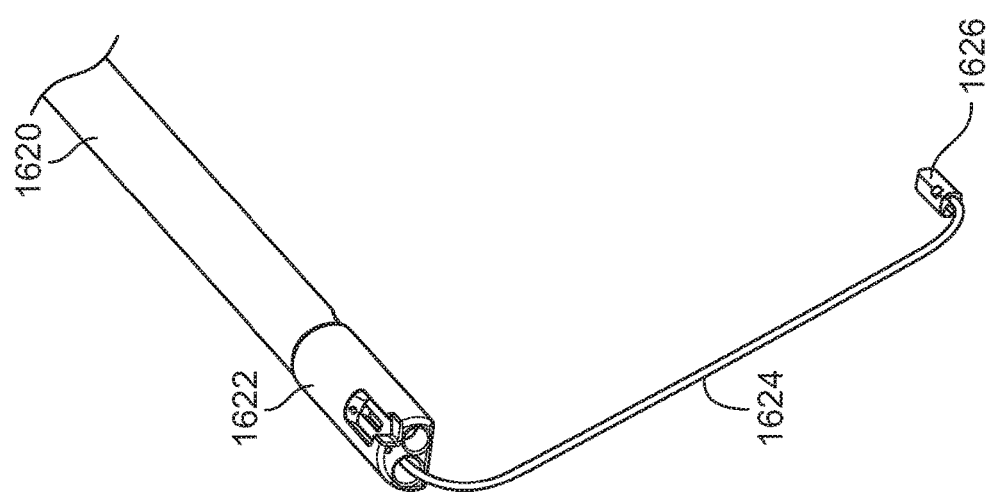
Figure 16G:
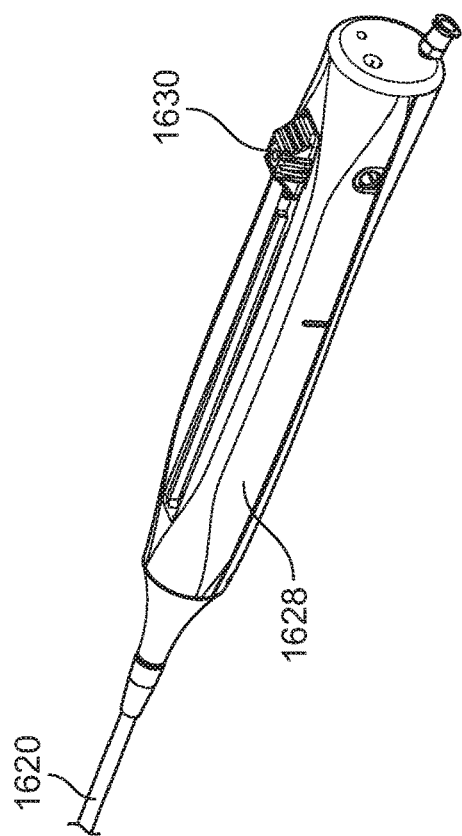
Figure 16F:
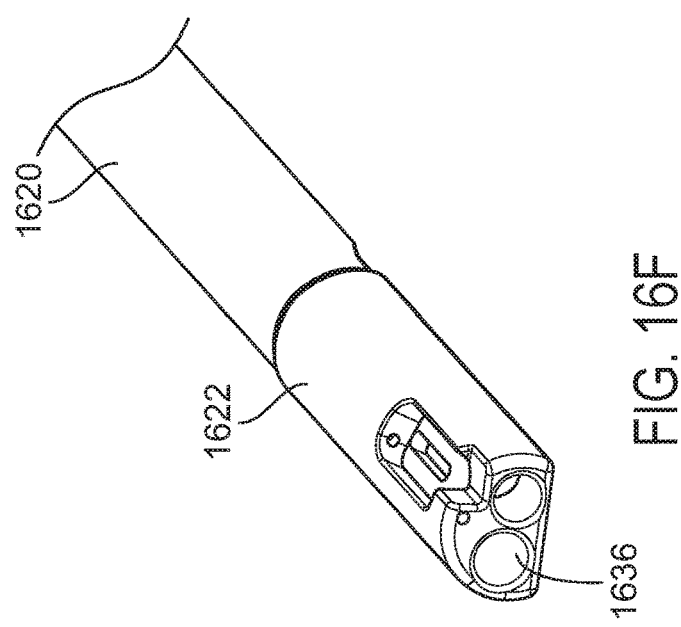
Figure 17A:
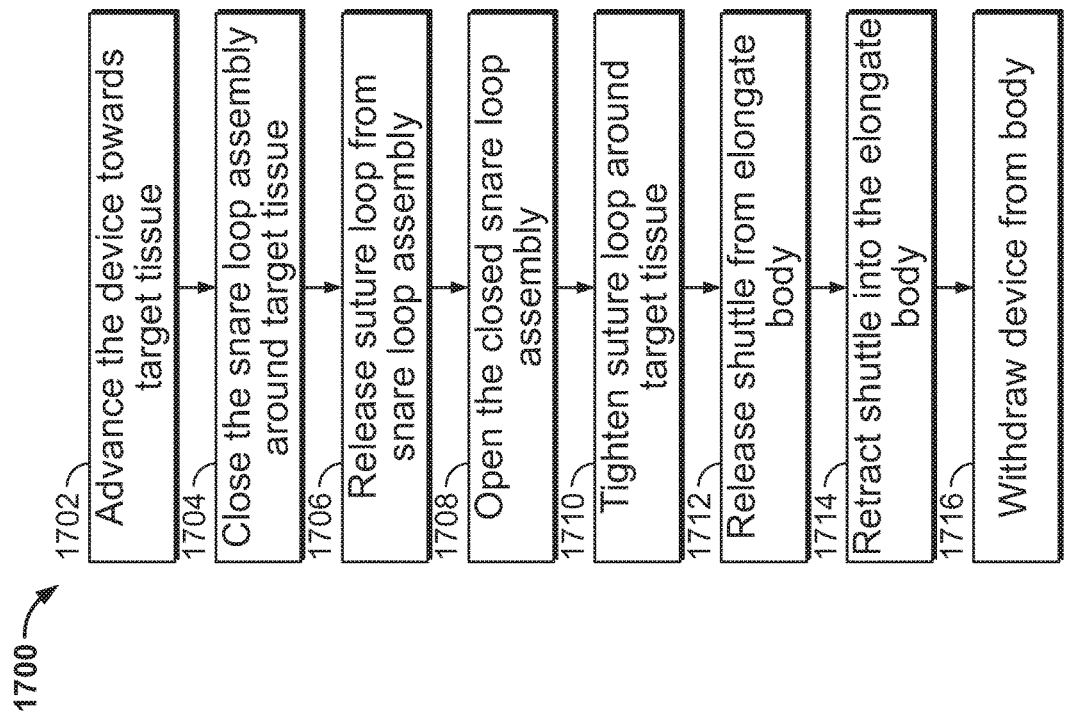
FIG. 17A is a flowchart for another variation of a tissue closing process.
Figure 17C:
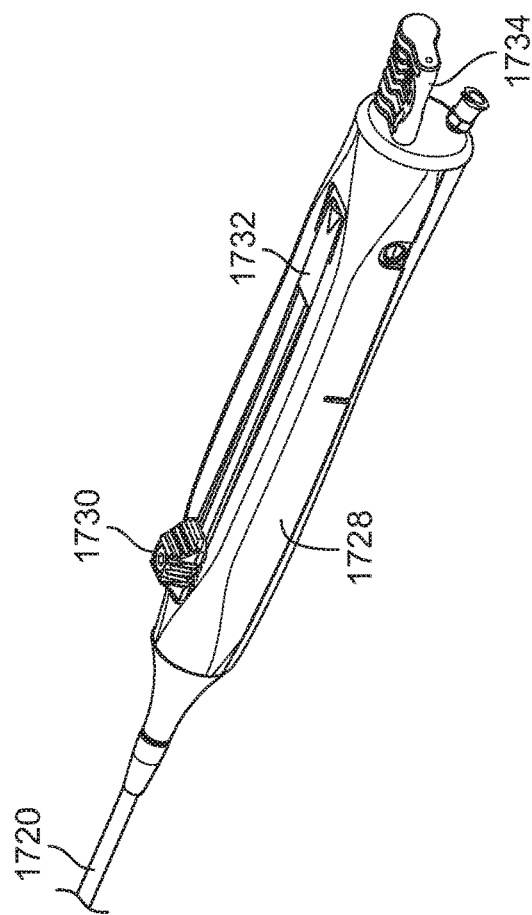
FIGS. 17B-17G are perspective views of a snare loop assembly and handle assembly corresponding to FIG. 17A.
Figure 17B:
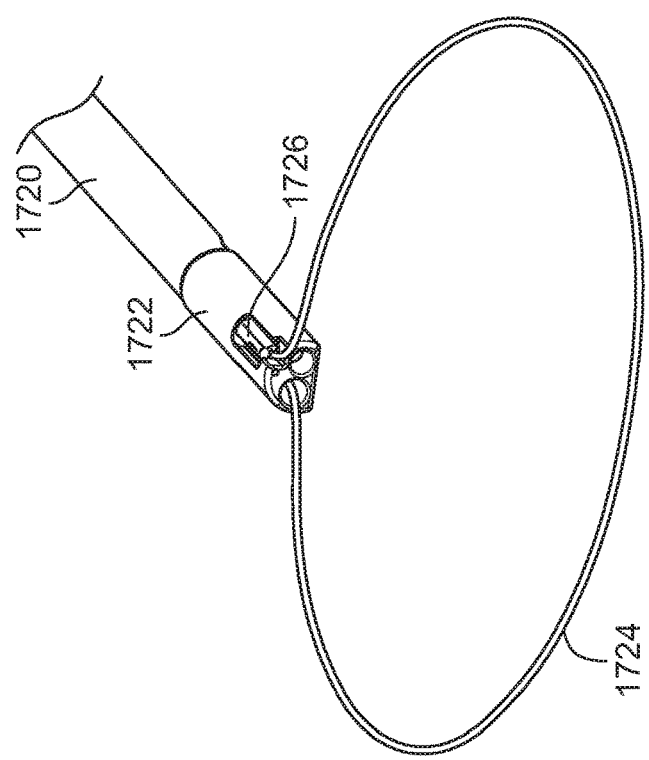
Figure 17E:
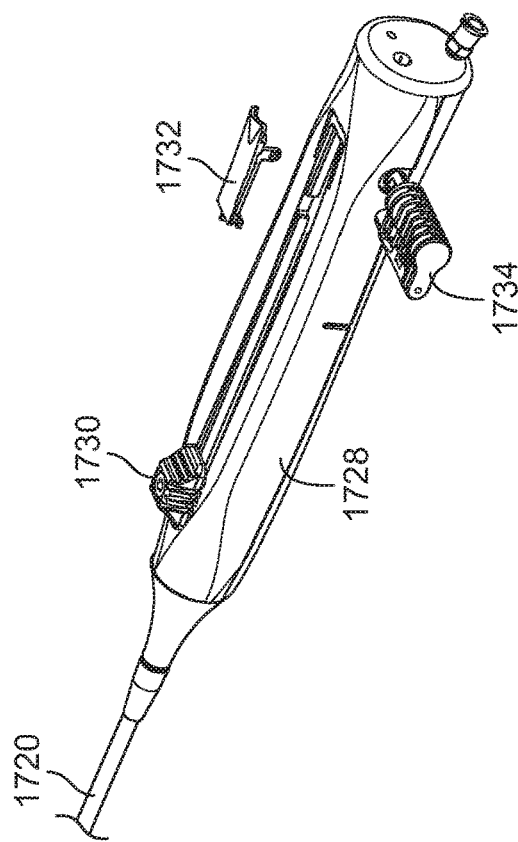
Figure 17D:
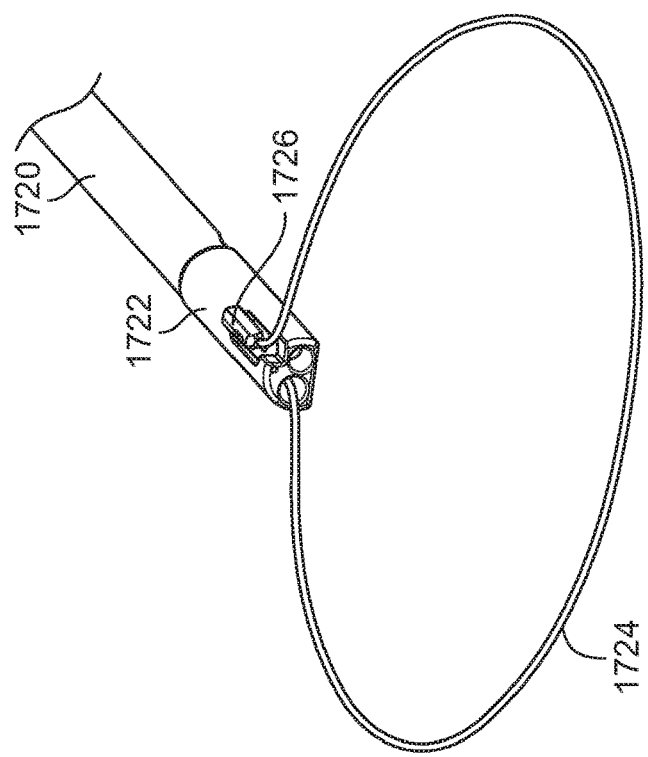
Figure 17G:
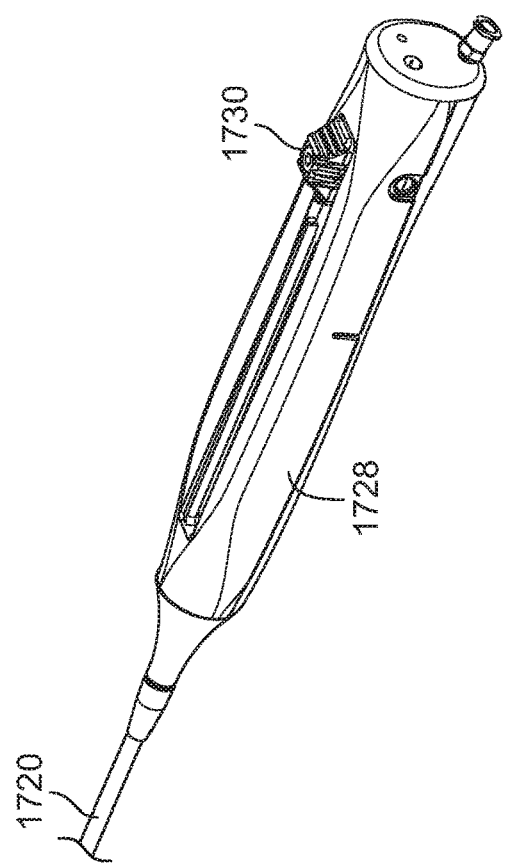
Figure 17F:
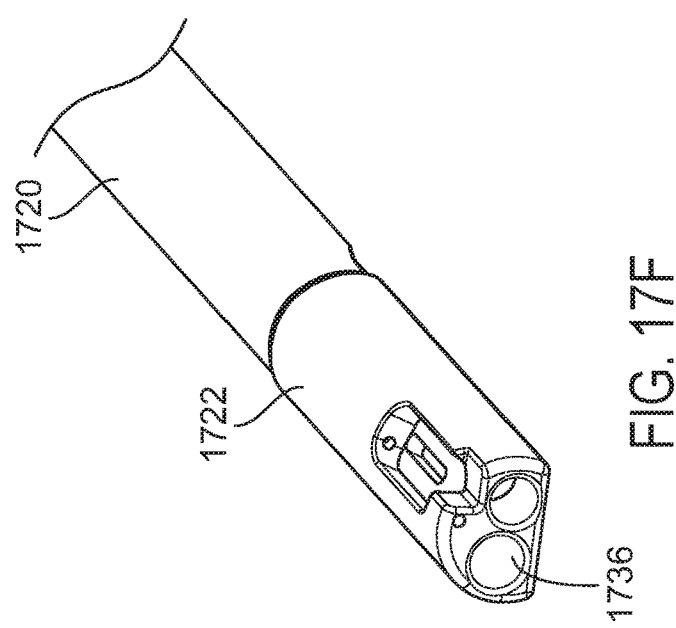

In a retracted configuration, the fixed end of the snare is released and an entirety of the snare and shuttle are retracted into a lumen of the elongate body, as illustrated in, for example, FIGS. 16F and 17F. The shuttle, which may be coupled to the distal (fixed) end of the snare, may be configured to fit through a lumen in the tip and a lumen of the elongate body (e.g., a first lumen (706) of the elongate body (704) as depicted in FIGS. 7A-7B, a first tip lumen (802) as depicted in FIG. 8).

The closure elements or snares described here may be made of any suitable material or combination of materials. For example, in some variations, the snare may be made from a shape-memory material, such as a shape-memory alloy (e.g., a nickel titanium alloy, etc.), or may be made from stainless steel, polyester, nylon, polyethylene, polypropylene, combinations thereof, and the like. In variations where the snare is made from a shape-memory material, the snare may be configured to take on a particular shape or configuration when the snare loop assembly is placed in an open configuration, but may still be at least partially withdrawn into the elongate body to place the snare loop assembly in a closed configuration. For example, the snare may form a generally circular, teardrop-shaped, oval or ellipsoid, or triangular loop when the snare loop assembly is placed in an open configuration.

Figure 3B:
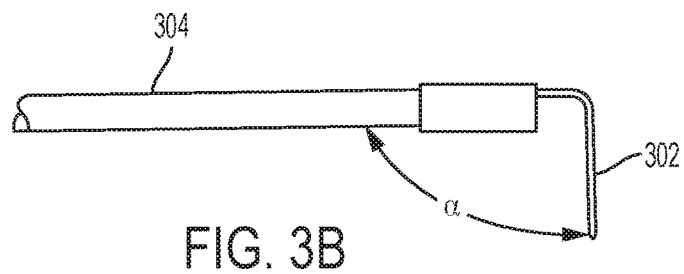
FIGS. 3B-3F are side views of the closure device shown in FIG. 3A.
Figure 3C:
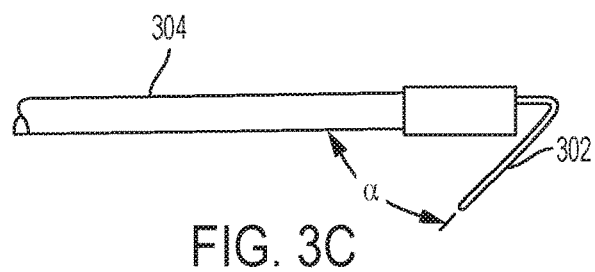
Figure 3D:
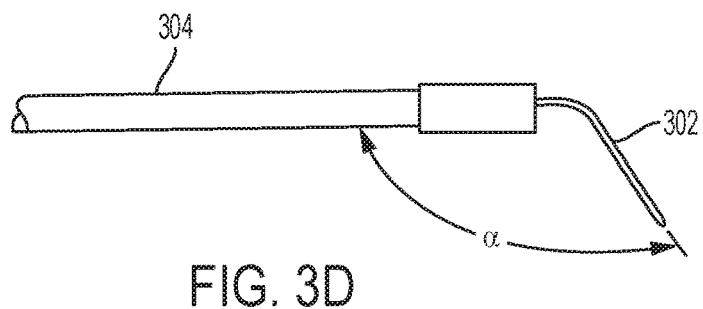
Figure 3E:
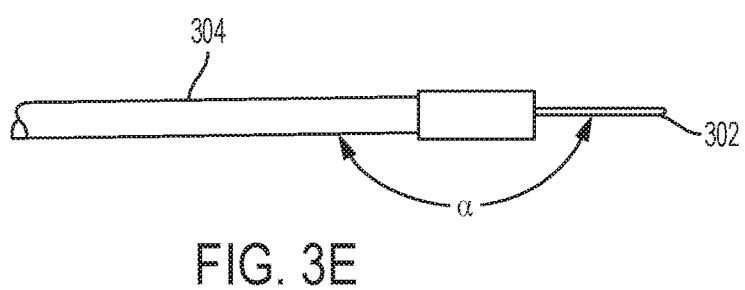
Figure 3F:
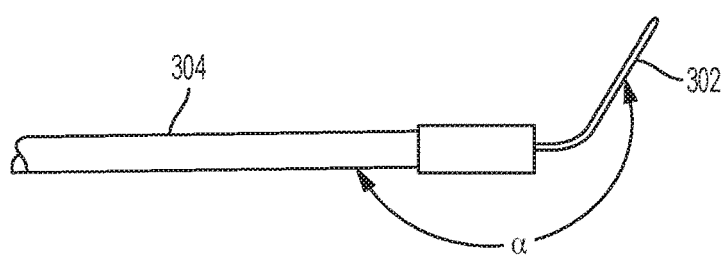

Furthermore, in some variations, the snare loop assembly may be angled relative to the elongate body. As shown in FIGS. 3A and 3B, the plane of snare loop assembly (302) is approximately perpendicular to the distal end of the elongate body (304), however, the plane of the snare loop assembly (302) may be varied over a wide range of angles ($\alpha$), as depicted in FIGS. 3B-3F. For example, the angle ($\alpha$) formed between the plane of the snare loop assembly (302) and the distal end of the elongate body (304), may be between about 5 degrees and about 85 degrees (FIG. 3C), may be about 90 degrees (FIGS. 3A and 3B), may be between about 95 degrees and about 175 degrees (FIG. 3D), may be about 180 degrees (FIG. 3E), or may be between about 185 degrees and about 270 degrees (FIG. 3F). In some variations, the angle ($\alpha$) formed between the plane of the snare loop assembly (302) and the distal end of the elongate body (302) may be between about 5 degrees and about 45 degrees. Angling the snare relative to the elongate body may aid the snare in capturing tissue, as angling may better position the snare relative to tissue as the closure device is moved in the body. In some variations, the angle ($\alpha$) may be preset, while in other variations, the angle ($\alpha$) is adjustable within a predetermined range.

Suture Loop

The snare loop assemblies described here may also comprise a suture loop for maintaining tissue in a closed manner. Generally, the suture loop may be releasably attached to the snare, for example, via a retention member, as will be described in more detail below. Furthermore, the suture loop may comprise a suture knot, but need not. This suture knot may be any suitable knot, including, but not limited to, a slip knot (e.g., a one-way slip knot) or a Meltzer knot. In some variations, at least a portion of the knot may be held within the tip of the elongate body. In other variations, the suture knot at least partially extends from the tip of the elongate body or may be positioned outside of the tip and may be temporarily held in fixed relation to the elongate body. When the suture loop comprises a suture knot, the suture loop may comprise a loop portion, a suture knot, and a tail extending from the suture knot. The suture tail may be pulled through the suture knot to reduce the diameter of the loop portion.

In variations where the suture loop comprises a slip knot, the suture may be advanced or withdrawn through the slip knot to change the size of the suture loop. In instances where the suture knot is held within or against a tip of the elongate body, the suture knot may not move while the size of the suture loop is changed. This may help prevent the closure device from damaging tissue. In some variations, the suture loop may comprise a unidirectional locking structure. In these variations, the unidirectional locking structure may be any structure capable of being advanced along the suture in one direction but resisting movement in a second direction. In these variations, the locking structure may be advanced over a portion of the suture loop to help lock a suture knot in place. For example, in some variations, the unidirectional locking structure may comprise a bead or a mechanical structure that is placed at least partially around the suture. In these variations, the bead may comprise one or more teeth or projections that allow the bead to be advanced along the suture in one direction, but prevent or resist movement in the opposite direction. The locking structure may be advanced via one of the closure devices described here, or it may be advanced by a separate device after the suture loop has been released from the closure device.

The suture loop may be made from any suitable material useful in tissue exclusion or closure. For example, it may be made of a biodegradable material (e.g., polylactic acid, polyglycolic acid, polylactic-co-glycolic acid, etc.), or it may be made of a non-biodegradable material (e.g., metal, steel, polyester, nylon, propylene, silk, combinations thereof, etc.).

When the suture loop is tightened to close tissue, it may be possible for tissue to be pulled into the suture knot of the suture loop. If too much tissue is pulled into the suture knot, the suture knot may clog or jam in a way that prevents the suture loop from being further tightened. In some variations the suture loop may comprise one or more pledgets or tube sections to help shield a portion of the suture knot.

Retention Member

When the snare loop assemblies described here comprise a retention member releasably coupling a snare and a suture loop, the retention member may be any suitable member, such as dual-lumen tubing. In some variations, one lumen may have a slit, perforation, or other opening along its length, which may allow the suture to pass therethrough when it is ready to be deployed. The slit need not extend or be continuous along the entire length of the retention member. In some variations, the slit may have prongs or arms along its length to help capture and retain the suture in the retention member. In other variations, the slit may be covered at spaced-apart locations with a biodegradable polymer, which may temporarily tack or hold down the suture. Of course, in still other variations, the retention member does not comprise a slit, and instead comprises some other type of retention mechanism, such as the prongs or tacks described just above. In yet other variations, there are no slits or openings in the retention member, and the suture loop is released upon removing or withdrawing the retention member.

Excess-Suture Management

In operation of the closure devices, it may be desirable to be able to open and close a snare loop assembly without prematurely releasing the suture loop from the snare assembly. Because the size of the loop of the snare loop assembly and the aperture defined thereby changes as the snare loop assembly is opened and closed, it may be necessary for the size of the suture loop to change in order to accommodate this change in aperture size and to prevent the suture from being prematurely released from the snare loop assembly. In some variations, opening the snare loop assembly may pull a suture through a slip knot to increase the size of the suture loop. This may, however, provide sufficient force to the suture loop to cause the suture to break or sever.

To help prevent this undesirable outcome, in other variations, the suture loop may be sized such that the suture loop is as large as or larger than the size of the aperture defined by the loop of the snare loop assembly when the snare loop assembly is in an open configuration. In this manner, the suture does not translate through the knot while the suture is loaded on the device and the size of the suture loop does not change. Thus, when the snare loop assembly is moved to either an open or closed configuration, the suture loop can assume a similar size without needing to advance additional suture through the suture knot.

Pre-sizing the suture loop to such a size, however, may result in extra slack in the suture loop when the snare is in both the open and closed configurations. To help prevent the excess suture from getting entangled with or caught on anatomical structures, instruments, or other obstructions, some or all of the slack in the suture loop may be held inside of the elongate body when the snare loop assembly is opened and/or closed. As such, the closure devices described here may comprise one or more excess-suture management features, which may be used in any suitable manner. The closure devices described here may comprise any suitable suture management features, for example, any of those described in U.S. patent application Ser. No. 12/752,873, entitled "Tissue Ligation Devices and Controls Therefor" and filed on Apr. 1, 2010, the entire content of which is incorporated by reference herein.

Retractable Snare

As mentioned above, in some variations, the closure devices described here may comprise a retractable snare. In some variations, the snare may be configured to be releasable along its length to separate the snare into two separate snare portions, as well as configured to be retractable through a lumen of the elongate body. In other variations, the closure device may comprise a snare having an end that is fixed relative to the elongate body, and the closure device may be further configured to release the fixed end of the snare and retract the previously fixed end of the snare into the elongate body. In some variations, the closure device may comprise a snare that has a fixed distal portion that is releasable from a side wall of the elongate body (or a tip thereof). For example, the closure device may comprise a first configuration in which a shuttle coupled to a distal end of the snare is fixedly coupled to the elongate body, and a second configuration in which the shuttle and the distal end of the snare are positioned within a lumen of the elongate body. In these variations, the fixed end of the snare, which may or may not be coupled to a shuttle, may be released from the closure device in any suitable manner.

FIG. 4 is an exploded perspective view of a variation of a closure device. FIG. 4 shows a perspective view of a distal portion of the closure device (400) comprising a tip (402), a shuttle (420) comprising a window or lock wire recess (422), and a lock wire (424). As shown there, the tip (402) may comprise a shuttle recess (408) having a rear surface (412) and a front surface (414), first and second lumens (404, 406), an L-shaped recess (410) extending between the front surface (414) of the shuttle recess (408) and a front surface of the tip (428), and a lock wire lumen (418). Also shown there is a track (416) further disposed in the shuttle recess (408). When the shuttle (420) is coupled to the tip (402), the shuttle may be positioned within the shuttle recess (408) and optionally the track (416). The shuttle (420) may be connected to a distal portion of the snare (not shown), which may be positioned in the approximately L-shaped recess (410), as will be described in detail below.

The lock wire (424) may be configured to extend through the tip (402) and the shuttle (420) and into the lock wire lumen (418). When sufficient force is applied to the lock wire (424) (e.g., at a proximal end thereof), the lock wire (424) may be retracted and the shuttle (420) may be released from the tip (402). In some variations, the lock wire (424) may comprise one or more bends (426) or coils, which may resist movement relative to the shuttle and/or elongate body. The bend (426) in the lock wire (424) may be configured to be disposed within the window or lock wire recess (422) of the shuttle (420) while the shuttle (420) is coupled to the tip (402). The bend (426) in the lock wire (424) may prevent low levels of force from retracting the lock wire (424) (i.e., may reduce the risk of premature or inadvertent release) as the bend (426) may contact a side wall of the lock wire recess (422), which may keep the lock wire from further retracting without sufficient force. To release the lock wire (424), the user may apply a proximal force (e.g., via a control) sufficient to straighten the bend (426).

As mentioned above, the snare may have a fixed distal portion that may be releasable from a tip attached to the elongate body, or from a side wall of the elongate body, and retractable through a lumen of the elongate body. FIGS. 5A and 5B are perspective views of a distal portion of a closure device (500) having a retractable snare. FIG. 5C is a top view of the closure device (500) shown in FIG. 5A. As shown in FIG. 5A, the closure device (500) may comprise an elongate body with a tip (503) and a snare loop assembly (501) at least partially extending from the tip (503). The snare loop assembly (501) may comprise a snare comprising a proximal portion (512) and a distal portion (514), and a suture loop (not shown) releasably coupled to the snare (512, 514), via, for example, a retention member (not shown). A shuttle (516) may be connected to the distal portion (514) of the snare and may be releasably coupled to the tip (503) of the elongate body. For example, the tip (503) may comprise a shuttle recess (509) and an approximately L-shaped recess (510) in a side wall of thereof. When the shuttle (516) is coupled to the tip (503), the shuttle (516) may be positioned within the shuttle recess (509) and the distal portion (514) of the snare may be positioned in the L-shaped recess (510).

As shown in FIG. 5B, the closure device (500) may comprise an elongate body (502) comprising a tip (503) coupled to a distal portion of the elongate body (502). A snare loop assembly may comprise a snare and a suture loop, although only a proximal portion (512) of the snare and a distal portion (514) of the snare are shown in FIG. 5B. The proximal portion (512) of the snare may extend from a first lumen (504) of the tip (503) to form a loop defining an aperture that may be placed around tissue. When a suture loop comprises a suture knot (not shown), the suture knot and a tail of the suture loop may be positioned in and/or extend through the second lumen (506).

The proximal portion (512) of the snare may extend through the first lumen (504), where it may be operatively connected to a handle assembly (not shown). The handle assembly may advance and retract a proximal end of the snare (e.g., proximal to the proximal portion shown) to control the size (e.g., diameter, circumference) of the aperture formed by snare loop assembly. Since the suture loop (not shown) is coupled to the snare, movement of the proximal end of the snare may move part of the suture loop into or out of the first lumen (504). Additionally, in variations in which the suture loop is sized to have an amount of excess suture, some or all of the excess suture may be held or otherwise maintained in the first lumen (504) of the tip (503) or within a lumen of the elongate body.

The tip (503) may additionally comprise a lock wire lumen (508) both distal and proximal to the shuttle recess (509), and thus the shuttle (516) when the shuttle (516) is positioned within the shuttle recess (509). The lock wire lumen (508) may be configured to secure the shuttle (516) relative to the tip (503) when a lock wire (520) is extended through the tip (503) from the elongate body, positioned through a window or lock wire recess (518) of the shuttle (516), and through the lock wire lumen (508). The window (518) may also be open into the side of the tip (503), which may allow a bend of the lock wire (520) to extend at least partially into the window (518) to resist proximal movement of the lock wire (520) relative to the shuttle (516).

The proximal portion (512) of the snare may be operatively connected to a handle assembly and a distal portion (514) of the snare may be connected to the shuttle (516). Generally, the shuttle (516) may be a structure configured to couple the distal portion (514) of the snare to the tip (503) of the closure device. The shuttle (516) may be coupled to the distal portion (514) of the snare and may be releasably coupled to the tip (503) of the closure device, and may thus be configured to fix the distal portion (514) of the snare relative to the tip (503). When the shuttle (516) is coupled to the tip (503), the distal portion (514) of the snare is fixed relative to the tip (503), and a proximal end (and the proximal portion (512)) of the snare may be advanced or withdrawn (e.g., via a control such as a handle assembly) to open or close the snare and snare loop assembly.

As shown in FIGS. 5A-5C, the distal portion (514) of the snare may be positioned in the approximately L-shaped recess (510) when the shuttle (516) is coupled to the tip (503) (e.g., positioned in a shuttle recess (509) of the tip (503)). The approximately L-shaped recess (510) may comprise a first surface (511) and a second surface (513) that is transverse to the first surface (511). In some variations, the second surface (513) may be perpendicular (i.e., at an approximately 90 degree angle) to the first surface (511), while in other variations, the second surface (513) may be angled away from the first surface (511). For example, the angle may be any suitable angle that prevents interference of the second surface (513) with the distal portion (514) of the snare and does not otherwise interfere with or breakthrough the second lumen (506). For example, the angle between the first and second surfaces (511, 513) may be an obtuse angle, for example, about 100 degrees, about 105 degrees, about 110 degrees, between about 90 degrees and about 105 degrees, between about 95 degrees and about 110 degrees, or the like. In some variations, the second surface (513) may form a shelf on which at least a portion of the distal portion (514) of the snare may rest without being confined. The L-shaped recess (510) may be configured such that the distal portion (514) of the snare positioned in the recess (510) may bend freely away from the tip (503) (e.g., a longitudinal axis of the tip). In this way, the snare loop assembly may be transitioned from an open configuration to a closed configuration and vice versa without being constrained by the surfaces of the recess (510).

Utilizing a recess (510) with first and second surfaces (511, 513) that are perpendicular or form an obtuse angle relative to one another may provide a number of advantages compared with conventional U-shaped recesses. For example, conventional U-shaped recesses do not allow a distal portion of a snare to bend freely and are thus prone to interference, misalignment, and tissue pinching. In contrast, as the distal portion (514) of the snare is able to bend and move away from a central longitudinal axis of the tip (503) without being constrained by the surfaces of the recess (510), the distal portion (514) does not encounter interference from the tip (503) or shuttle (516). Thus, frictional forces and/or an obstruction that may otherwise force the shuttle (516) to tilt up and out of the tip (503) and create misalignment between the lock wire lumens of the tip (503) and the shuttle (516) are minimized or prevented. Accordingly, utilizing the described recess (510) may prevent or minimize interference between the surfaces of the recess (510) and the distal portion (514) of the snare, which may make the closure device easier to manufacture by providing better and more consistent alignment of the lock wire lumen openings. Additionally, utilizing the described recess (510) may prevent or minimize tissue from becoming caught or pinched between the tip (503) of the elongate body and the distal portion (514) of the snare positioned in the recess (510). In particular, because the distal portion (514) of the snare may bend freely without interference from the tip (503), pinching of tissue between the distal portion (514) and the tip (503) may be substantially reduced. Accordingly, both the ease of use of the closure device during a procedure and the assembly of the closure device may be improved as alignment and fit of the retractable snare is improved.

In another variation, the recess may be in the form of a channel comprising an increasing width from the front surface of the shuttle recess to the front surface of the tip. For example, in these variations, a proximal portion of the channel adjacent to or at the shuttle recess (e.g., aligned with the front surface of the shuttle recess) may be narrower than a distal portion of the channel adjacent to or at the distal end of the tip (e.g., aligned with the front surface of the tip). Thus, the recess may be in form of a tapered channel. Utilizing a recess with increasing width distally along a longitudinal axis of the tip (502) may assist in holding the shuttle (516) within the shuttle recess (509) but may still allow the distal portion (514) of the snare to bend freely (e.g., without being constrained by the walls of the recess).

FIG. 5C shows a top view of the tip (503) with a shuttle recess (509) in which the shuttle (516) may be positioned.

As shown, the lock wire (520) may be positioned within the lock wire lumen and the window or lock wire recess (518) of the shuttle (516). The distal portion (514) of the snare may be in contact with the first and second surfaces (511, 513) of the recess (510) of the tip (503) and otherwise unencumbered to allow the distal portion (514) to be manipulated without interference or contact from the tip (503). When the shuttle (516) is coupled to the tip (503) of the elongate body within the shuttle recess (509), a clearance between the shuttle (516) and the tip (503) may be about 0.004 inches (0.102 mm) total. For example, in some variations, the shuttle may have a width of about 0.060 inches+0.001/−0.002 inches (1.524 mm+0.0254/−0.0508 mm) and a length of about 0.183 inches±0.003 inches (4.648 mm±0.0762 mm) and the shuttle recess (509) may have a width of about 0.070 inches±0.003 inches (1.778 mm±0.0762 mm) and a length of about 0.190 inches±0.003 inches (4.826 mm±0.0762 mm), which may result in a shuttle clearance of between about 0.003 inches (0.0762 mm) and about 0.0075 inches (0.1905 mm) on each side of the shuttle, and a shuttle clearance of between about 0.0005 inches (0.0127 mm) and about 0.0065 inches (0.1651 mm) at the proximal and distal ends of the shuttle. In some variations, the shuttle clearance on each side of the shuttle may be about 0.005 inches (0.127 mm) and the shuttle clearance on each of the proximal and distal ends may be about 0.0035 inches (0.0889 mm).

Shuttle

As described above, in some variations, a shuttle may be provided in a snare loop assembly (e.g., coupled to a distal portion or end of the snare) to allow a distal portion of a snare loop to be released from a tip of the elongate body and retracted into a lumen of the tip and/or elongate body. While a diameter of the snare may generally be smaller than a diameter of a tip or elongate body lumen, and thus may pass easily into the lumen, one disadvantage of other shuttle configurations is their inability to retract into a lumen, thus preventing retraction of the snare into a tip and/or elongate body. Consequently, when using devices with other shuttle configurations, the shuttle and the snare loop attached thereto are at risk of being caught on anatomical features and the deployed suture as the closure device is retracted from the target tissue.

In contrast to other devices, the closure devices described herein may comprise a shuttle that is configured to fit through a lumen in the tip and/or elongate body. For example, a device for closing a target tissue may comprise an elongate body comprising a lumen therethrough, a snare loop assembly comprising a snare and a suture loop releasably coupled to the snare, and a shuttle connected to a distal portion of the snare and releasably coupled to the elongate body that may comprise a configuration to fit into the lumen of the elongate body. Put another way, the shuttle may be configured to retract into a lumen of the tip and/or the elongate body.

For instance, after a shuttle is released from the tip of the elongate body (e.g., from a shuttle recess in the tip), the snare loop and the shuttle may be partially or completely retracted into the closure device such that the no portion of the snare or shuttle extends out of the lumen or only a small portion of the snare and/or shuttle extends out of the lumen. In some variations, the closure device may be configured such that the entirety of the snare and the shuttle may be retracted into a lumen of the tip and/or elongate body, while in other variations, the closure device may be configured such that the snare partially retracts into the lumen such that all or a portion of the shuttle remains outside of the tip/elongate body (i.e., is not retracted into the lumen). This partial or full retraction reduces the likelihood of tissue pinching and/or catching on the deployed suture. Additionally, partial or full retraction of the snare also reduces the risk of the snare being caught on anatomical features. In this manner, the closure devices described herein may be retracted from the target tissue and removed from the body more safely.

Figure 18:
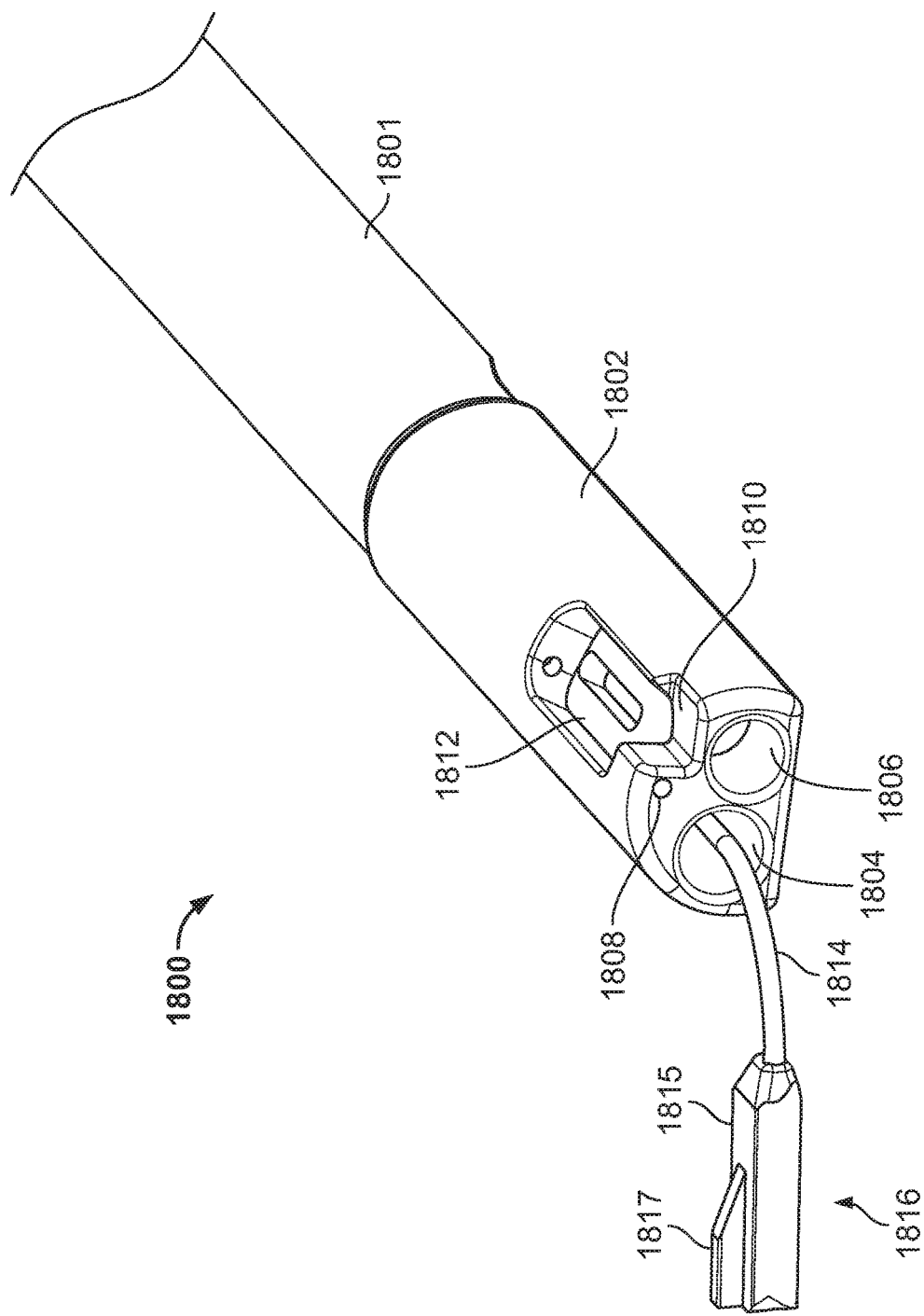
FIG. 18 is a perspective view of a variation of a closure device having a partially retractable shuttle.

As mentioned above, in some variations, the closure devices described here may comprise a shuttle that is configured to partially retract into a lumen of the tip and/or elongate body of the closure device. For example, FIG. 18 is a perspective view of a variation of a closure device (1800) having a partially retracted snare. The closure device (1800) may comprise an elongate body (1801) comprising a tip (1802), a first lumen (1804), and a second lumen (1806), a shuttle (1816), and a snare (1814) (only a distal portion of the snare is depicted). The shuttle (1816) may be connected to the distal portion of the snare (1814). Although not depicted in FIG. 18, the snare (1814) may be releasably coupled to a suture loop, for example, via a retention member, before deployment of the suture loop. When the suture loop comprises a suture knot (not shown), the suture knot and a tail of the suture loop may be positioned in and/or extend through the second lumen (1806). The tip (1802) may additionally comprise a lock wire lumen (1808) that may be configured to receive a lock wire that may secure the shuttle (1816) relative to the tip (1802) and the elongate body (1801). The tip (1802) may comprise a shuttle recess (1812), in which the shuttle (1816) may be positioned and housed when the shuttle (1816) is coupled to the tip (1802). The tip (1802) may further comprise an approximately L-shaped recess (1810) in a side wall of the tip (1802).

In the variation shown in FIG. 18, the snare (1814) may be fully or partially retractable into the first lumen (1804), while the shuttle (1816) may be partially retractable into the first lumen (1804). For example, the diameter of the snare may be smaller than a diameter of the first lumen (1804), and a maximum transverse dimension (transverse to the longitudinal axis of the snare) of at least a portion of the shuttle (1816) (e.g., a height, width, or a diameter) may be larger than the diameter of the first lumen (1804). For example, the shuttle (1816) may comprise a first proximal portion (1815) coupled to the distal portion of the snare (1814) and a second distal portion (1817). In some variations, the first proximal portion (1815) may have a maximum transverse dimension that is smaller than a diameter (and/or height/width) of the first lumen (1804) and the second portion (1817) may have a maximum transverse dimension that is larger than the diameter (and/or height/width) of the first lumen (1804). In other variations, the first portion of the shuttle (1816) may have a smaller cross-sectional area than a cross-sectional area of the first lumen (1804), while the second portion of the shuttle (1816) may have a larger cross-sectional area than the cross-sectional area of the first lumen (1804), such that the second portion of the shuttle (1816) may not fit within the first lumen (1804). In yet other variations, the second portion of the shuttle (1816) may comprise a width that is larger than the diameter (or width) of the first lumen (1804), which may prevent the second portion of the shuttle from being retracted into the first lumen (1804). Thus, in some variations, the distal portion of the snare (1814) may be partially (as shown) or fully retracted into the first lumen (1804), while the shuttle (1816) may only be partially retracted into the first lumen (1804) (or in some variations, remain fully exposed but positioned closer to/just distal of a distal end of the elongate body/tip).

In other variations, as will be described in detail herein, the closure devices described here may comprise a shuttle that is sized and shaped to fully retract into a lumen of the tip and/or the elongate body of the closure device. In these variations, a maximum transverse dimension of the shuttle may be less than a diameter (and/or height/width) of the lumen of the tip and/or elongate body. For example, FIGS. 9A and 9B are perspective views of a variation of a shuttle that is configured to fully retract into a lumen of the tip and/or the elongate body. As described above, the shuttle may be connected to a distal portion of the snare and may be releasably coupled to the tip of the elongate body. The shuttle (900) may comprise a first lumen (902, 910), a second lumen (904), a window or lock wire recess (906), and a projection (908). The first lumen (902, 910) may comprise a lock wire lumen with a distal portion (902) and a proximal portion (910) separated by the lock wire recess (906). A lock wire (not shown) may be advanced through or otherwise disposed in the lock wire lumens (902, 910) and the lock wire recess (906) to releasably couple the shuttle (900) to the elongate body. The projection (908) may be configured to engage with a corresponding track in a shuttle recess of a tip (e.g., track (416) of a shuttle recess (408)). This engagement may minimize rotation of the shuttle (900) relative to the tip when external forces are applied to the snare loop.

A user may use the closure device to pull the shuttle (900) into a lumen of the elongate body when the snare is fully retracted. The shuttle may comprise a configuration to fit into the lumen. The shuttle may comprise various sections or portions with different characteristics, for example, different diameters, cross-sectional areas, cross-sectional shapes, materials, and the like, which may improve the fit and slidability of the shuttle in the lumen. For example, at least some portions of a cross-section of the shuttle may correspond to the shape of the lumen. In some variations, a radius of curvature of at least a portion of the shuttle may be the same as a radius of curvature of the lumen. The shuttle may comprise any suitable length allowing the shuttle to be releasably coupled to the elongate body and to fit into the lumen. The shuttle may also comprise any suitable configuration to couple with a lock wire, such as a lock wire lumen and optionally a window or lock wire recess. For instance, the shuttle (900) may comprise a lock wire recess (906) comprising a width between about 0.015 inches (0.381 mm) and about 0.025 inches (0.635 mm).

Figure 10:
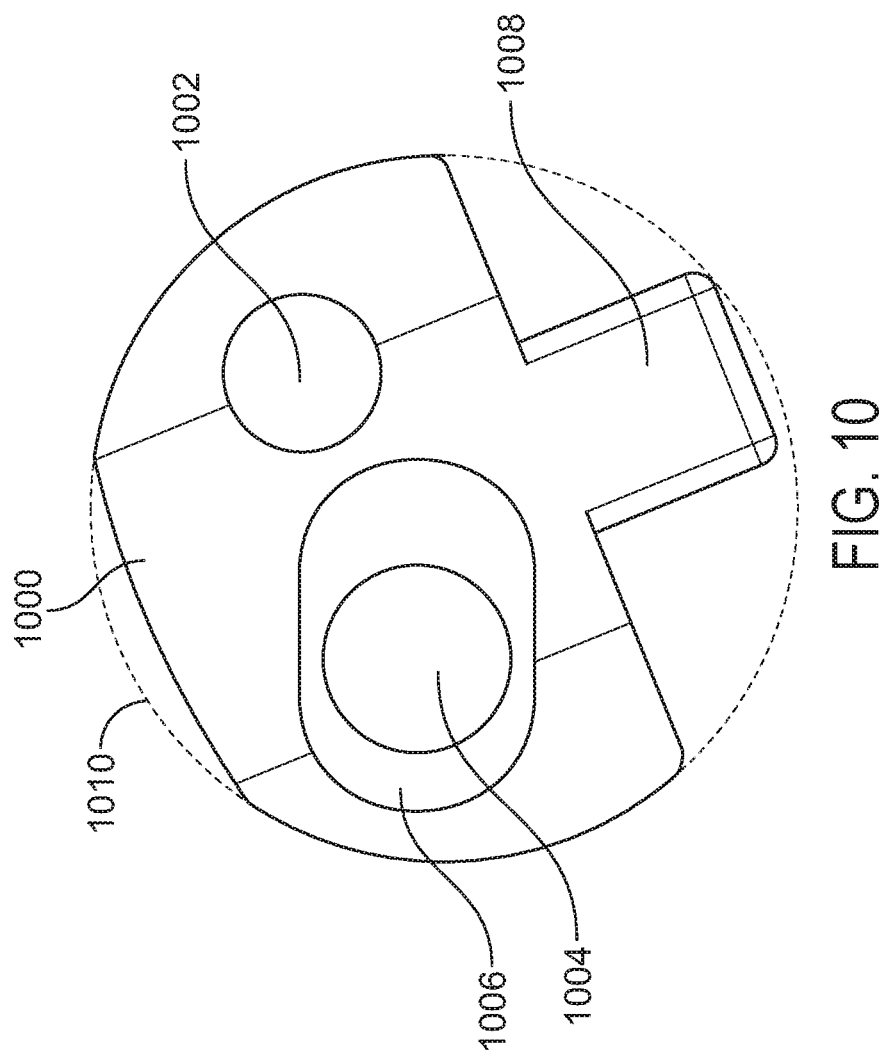
FIG. 10 is a sectional view of a variation of a shuttle in a lumen of a tip of a closure device.

FIG. 10 is a sectional view of a variation of a shuttle in a lumen of a tip of a closure device. As mentioned above, in some variations, the shuttle (1000) may comprise a shuttle diameter that is less than a diameter of a lumen (1010) of the tip (e.g., the first lumen (1804) in FIG. 18). This configuration allows the shuttle (1000) to fully retract into the lumen when the snare is fully retracted. For example, in one variation, the shuttle (1000) may comprise a radius between about 0.015 inches (0.381 mm) and about 0.030 inches (0.762 mm). In some variations, the shuttle (1000) may comprise a radius of about 0.030 inches (0.762 mm). In these variations, the lumen may comprise a radius of about 0.031 inches (0.80 mm), and thus, the radius of the shuttle (1000) may be less than the radius of the lumen (1010). In these variations, the shuttle (1000) retracted into the lumen (1010) has a clearance fit. A clearance fit may be a positive difference between a size of the lumen (e.g., diameter, height, width) and a size of the shuttle (e.g., a dimension (height, width, diameter) of the largest portion of the shuttle). In other variations, the shuttle diameter may be equal to the diameter of the lumen (1010) and or may be slightly larger than the diameter of the lumen (1010), but the shuttle may be configured to compress or otherwise decrease in size in order to fit within the lumen (1010).

The shuttle (1000) may comprise a first lumen (1002), a second lumen (1004), and a projection (1008). The second lumen (1004) may comprise a snare lumen where FIG. 10 illustrates a distal portion of the snare lumen. The snare lumen may house a portion of the snare such that the shuttle (1000) is coupled to a distal portion of the snare. A proximal portion of the second lumen (1004) may comprise an offset obround shape (1006) and a distal portion of the second lumen may comprise a circular shape. In one variation, a proximal portion of the snare lumen comprises an offset obround shape. An end of the snare may comprise a flattened portion (not shown) configured to fit within the obround shape (1006). In these variations, the use of a lumen with obround and circular portions may assist in preventing the flattened portion of the snare from pulling out of or breaking through the second lumen (1004) (e.g., from the obround portion to the circular portion) and coming out of the shuttle (1000). The flattened portion may further be bonded to the obround shape (1006) to prevent the snare from pulling through the second lumen (1004) as well as preventing the snare from rotating relative to the shuttle. The obround shape (1006) may be filled with adhesive, such as epoxy, to bond the flattened portion of the snare to the shuttle (1000). The first lumen (1002) may comprise a lock wire lumen and may be sized and shaped for passage of a lock wire therethrough. In some variations, the diameter of the lumen (1010) of the elongate body may be equal to or less than about 0.063 inches (1.60 mm). The shuttle diameter may be equal to or less than about 0.061 inches (1.56 mm).

The shuttle may be formed from any suitable material or materials, such as, for example, one or more metals (e.g., stainless steel), one or more rigid plastics, one or more polymers, or the like. In some variations, the shuttle may be formed from the same material or materials as a portion of the tip or elongate body, but need not be. In some variations, the shuttle may be formed from one or more of polyetherimide (e.g., Ultem®), polycarbonate, and stainless steel.

Handle

As described above, the closure devices described here may comprise a handle or other control mechanism. The handle may have any suitable shape or configuration, for example, any of those described in U.S. patent application Ser. No. 12/752,873, entitled "Tissue Ligation Devices and Controls Therefor" and filed on Apr. 1, 2010, which was previously incorporated by reference, or U.S. patent application Ser. No. 14/195,797, entitled "Tissue Ligation Devices and Methods Therefor" and filed Mar. 3, 2014, the entire content of which is hereby incorporated by reference herein.

The handle may serve many purposes. Of course, the handle may provide an interface between the device and the user as the user may hold onto and control the device and its components using the handle. The handle may be used to control and actuate the snare loop assembly through the elongate body, guide the elongate body, and/or modify the shape of the elongate body using a pull wire controlled through the handle. The handle may enable a user to control the release of the suture loop from the closure element, and in variations in which a visualization tool is used, it may be used to house electronic or other components for the visualization tool. The handle may comprise any suitable elements to facilitate use of the device for the closure of tissue, including sliders, knobs, switches, latches, push buttons, and the like, which may be coupled to any component of the snare loop assembly to pull, push, open, close, deploy, or otherwise use the component.

In some embodiments, the handles of the closure devices described here may comprise a tensioning mechanism for managing the tension applied to a portion of the suture loop (e.g., a tail of the suture loop) of the closure device. When the closure devices are used to place and tighten a suture loop around a tissue, it may be desirable to manage the tension applied to the suture as the suture loop is tightened.

When the closure devices described comprise a snare that is temporarily fixed to the elongate body via a shuttle and a lock wire, the handle may comprise a mechanism that allows for withdrawal of the lock wire, and the lock wire may be withdrawn in any suitable manner. Current solutions do not provide a mechanism for full retraction of the snare and optionally the shuttle with safeguards that prevent premature retraction of the snare loop initiated by user error. The handle assembly and variations described in detail below allow a shuttle and snare loop to be fully retracted through or into the tip and/or the elongate body in a desired order that may assist in preventing user error. For example, a device for closing a target tissue may comprise an elongate body, a snare loop assembly comprising a snare and a suture loop releasably coupled to the snare, a shuttle configured to releasably couple to the elongate body, and a handle comprising a lock or a snare control with a limiter, which of which may be configured to limit movement of the snare control along a track.

FIGS. 11A-11B and 11D-11E are perspective views of an illustrative variation of a handle assembly for use with the closure devices described here. A handle (1104) of the handle assembly (1100) may be attached to the elongate body (1102). The handle (1104) may comprise a snare control (1106) configured to control movement of the snare (not shown), a track (1108), which may be formed on a side, top, or bottom thereof, and a lock (1110). The handle assembly (1100) may further comprise a suture control (1112) configured to tighten the suture loop. The suture control (1112) may be releasably coupled to the handle (1104) via a first opening (1118) and a second opening (1120). The snare control (1106) may comprise a slider and may be coupled to and slideably disposed within or on the track (1108). The track (1108) may comprise a first portion (1109) and a second portion (1116), and the lock (1110) may be configured to limit movement of the snare control (1106) along the second portion (1116) of the track. The device may be configured such that the snare control (1106) may freely move/slide along the first portion (1109) of the track to open or close a snare loop assembly regardless of whether the lock (1110) is engaged (i.e., when the lock is engaged and when the lock is disengaged), but may be prevented from moving/sliding along the second portion (1116) of the track when the lock (1110) is engaged. The handle (1104) may further comprise a side opening (1114) aligned with at least a portion of the second portion (1116) of the track.

The lock (1110) may physically limit retraction of the snare prior to release of the shuttle from the elongate body (1102). For example, the lock (1110) may comprise a stopper (1115) that extends along a length of the track. For example, the stopper (1115) may fit over and/or within the second portion (1116) of the track and may prevent the snare control (1106) from moving along or within the second portion (1116) of the track. In some variations, the stopper (1115) may comprise a rectangular plate that covers the second portion (1116) of the track, while in other variations, the stopper may comprise a cylindrical or other shaped element that fits within, covers, or otherwise blocks the track and/or prevents the snare control (1106) from moving proximally along the second portion (1116) of the track.

Additionally, in some variations, the lock (1110) may further comprise a release engagement portion (1111) configured to limit movement of the snare control (1106) along a second portion (1116) of the track (1108) until after release of the suture. In these variations, the release engagement portion (1111) may releasably couple to a release assembly within the handle. The release assembly may be configured to release a shuttle (not shown) from the elongate body (1102) and may hold the lock (1110) in position in or on the track (1108) until after release of the suture, as will be described in more detail below. In some variations, the release engagement portion (1111) may comprise a protrusion that may extend from the underside (e.g., bottom surface) of the stopper (e.g., at an approximately 90 degree angle) and may comprise an opening (1113) that may releasably couple to a portion of the release assembly.

Figure 11A:
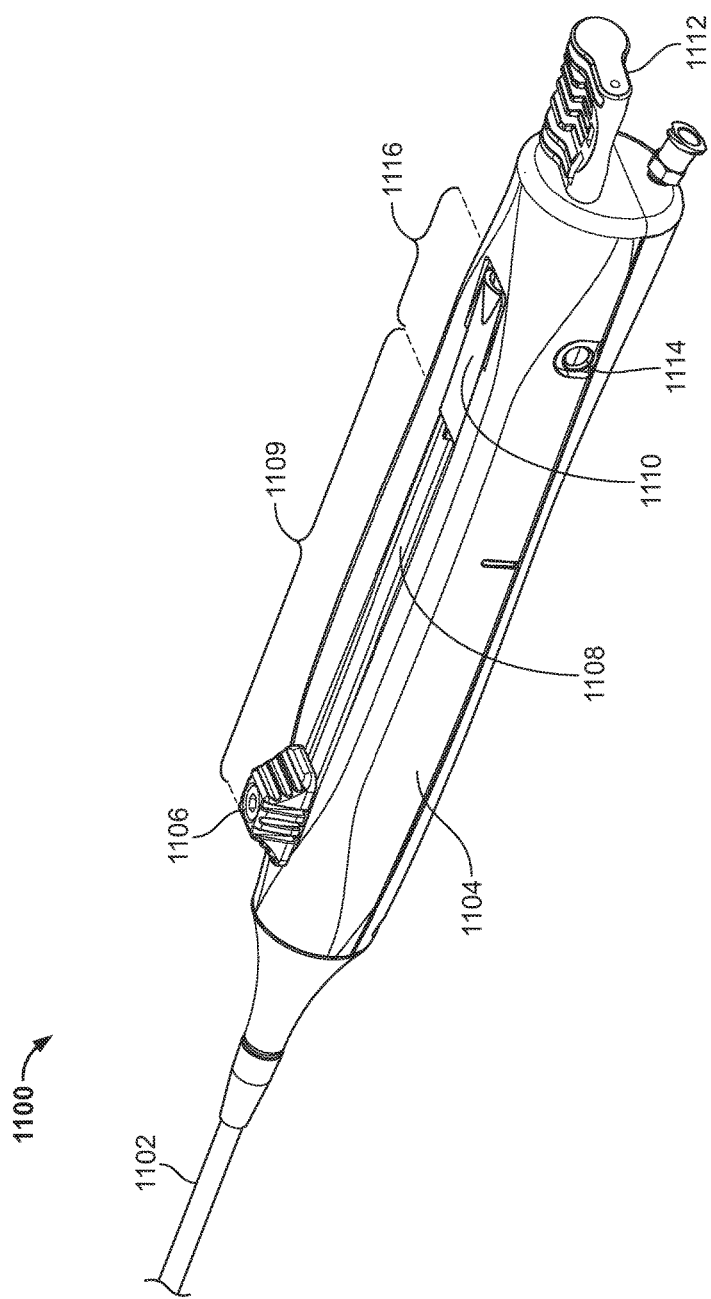
FIGS. 11A-11B and 11D-11E are perspective views of an illustrative variation of a handle assembly for use with the closure devices described here.
Figure 11B:
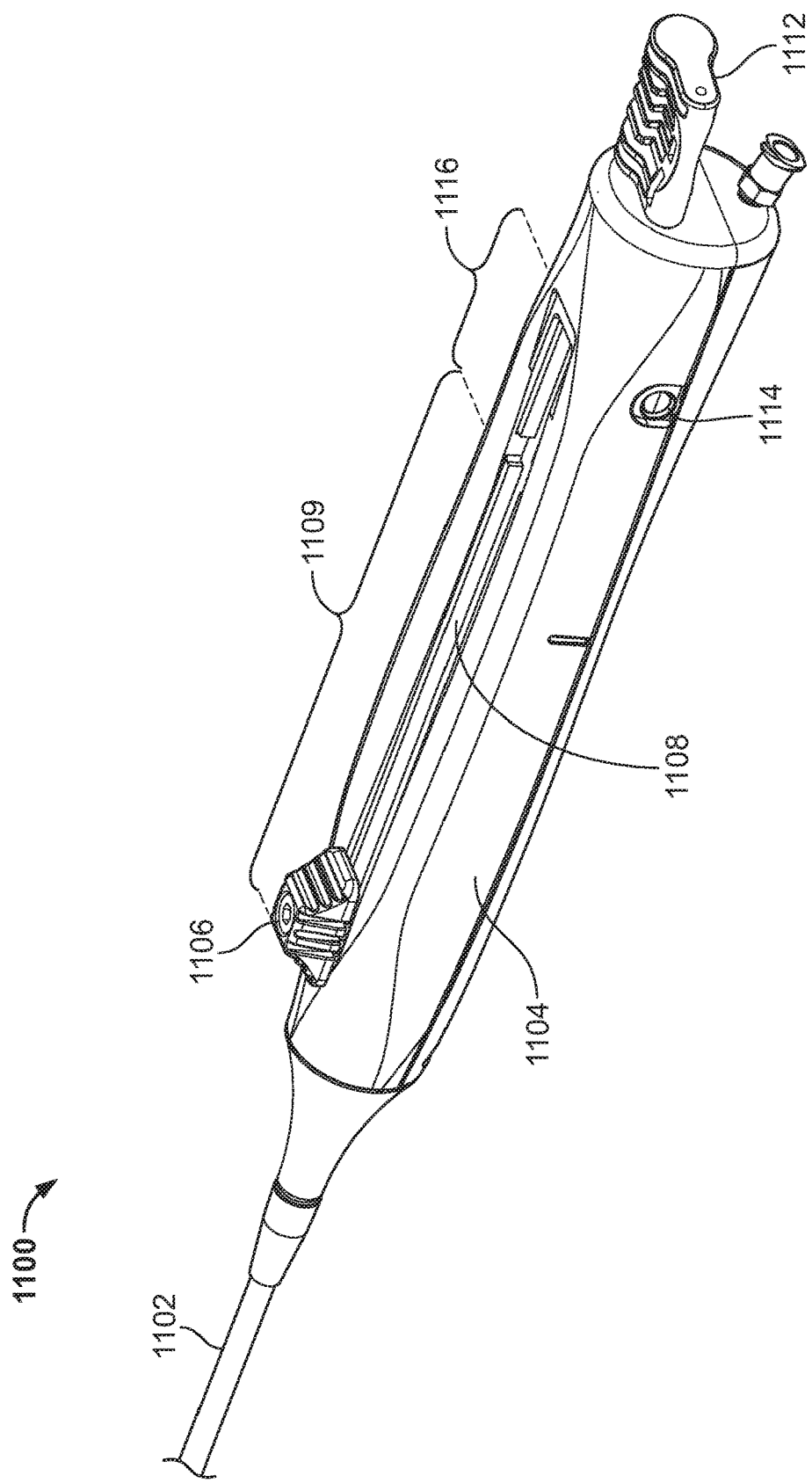
Figure 11D:
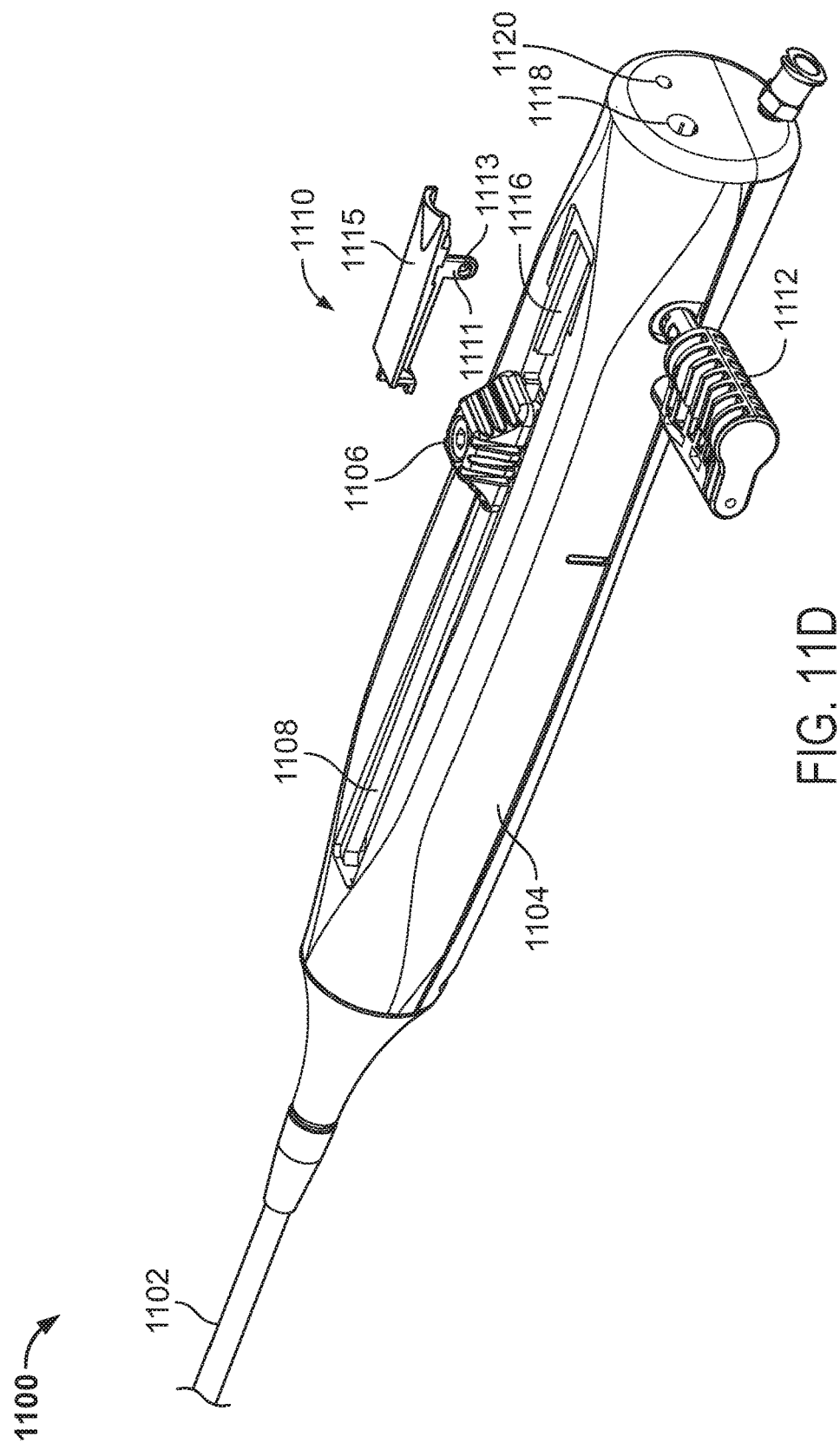
Figure 11E:
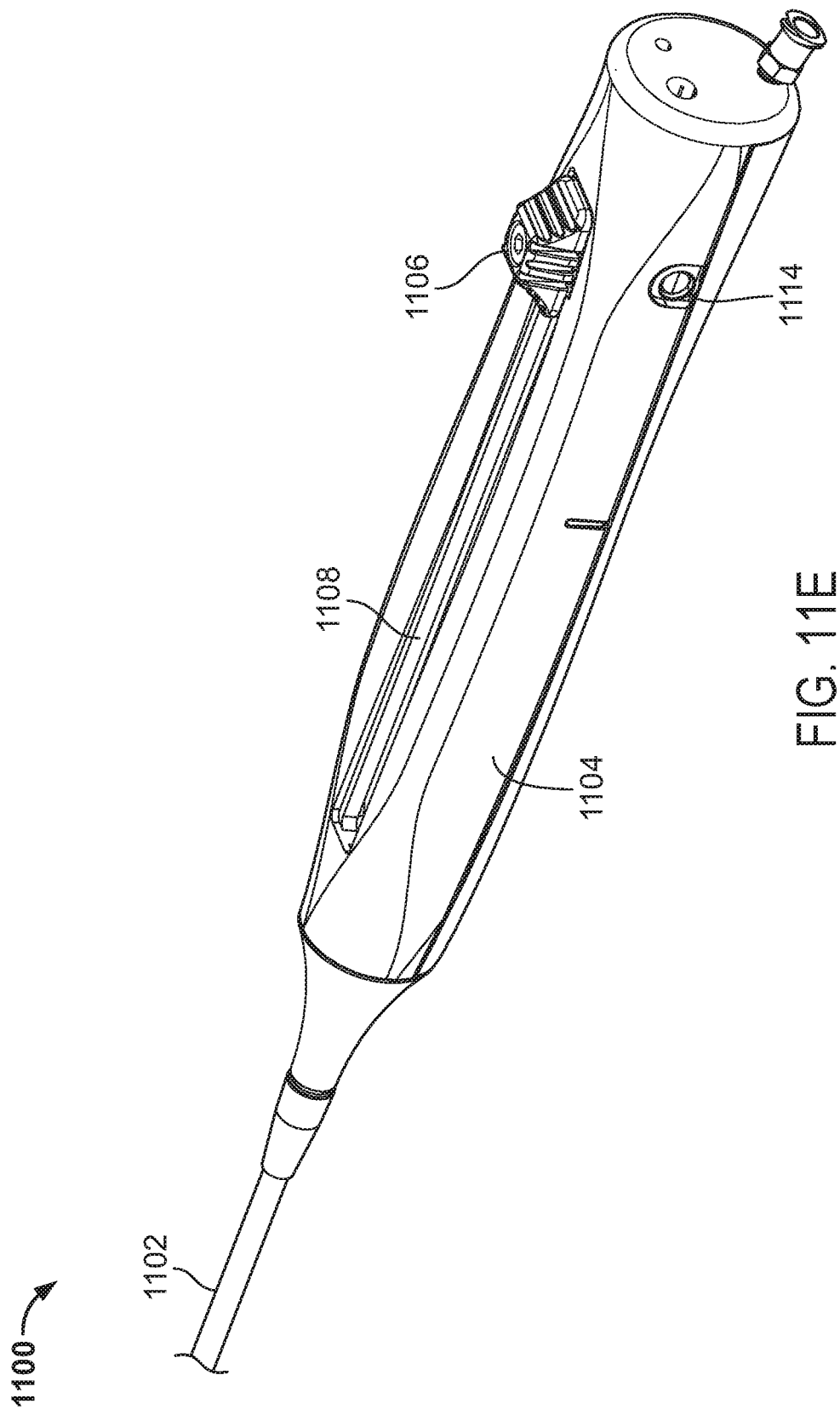

FIG. 11A depicts a lock (1110) covering the second portion (1116) of the track (1108), which limits movement of the snare control (1106) along the second portion (1116) of the track (1108). FIG. 11B depicts the lock (1110) removed from the second portion (1116) to allow movement of the snare control (1106) along the second portion (1116) of the track (1108). FIG. 11C is a top view of the handle assembly shown in FIG. 11B. FIG. 11D illustrates the snare control (1106) moved along the track (1108) to a position adjacent the second portion (1116). FIG. 11E illustrates the snare control (1106) moved to a proximal end of the track (1108). The snare control (1106) is configured to retract the snare and the shuttle into the elongate body (1102) when the snare control (1106) moves along the second portion (1116) of the track (1108), such as to the proximal end of the track (1108).

A proximal portion of the suture control (1112) may be configured to engage the release assembly through the opening (1114) in the handle to release the lock (1110) from the track (1108) and allow movement of the snare control (1106) along the second portion (1116) of the track (1108). Additionally, or alternatively, the suture control (1112) may be configured to engage the release assembly to retract a lock wire that releasably couples the shuttle to the elongate body (1102). Additionally, or alternatively, the suture control (1112) may be configured to engage the release assembly to release the shuttle from the elongate body (1102). In some variations, the closure device may be configured such that when the suture control (1112) engages the release assembly, the lock (1110) is released and the lock wire is simultaneously retracted, thereby releasing the shuttle from the elongate body (1102). Thus, in some variations, the lock (1110) may be released from the track (1108) and thus the handle (1104) and the shuttle may be released from the elongate body simultaneously.

FIG. 12 shows a perspective view of a suture control (1200) for use with a handle assembly such as the handle assembly (1100) described with respect to FIGS. 11A-11D. The suture control may comprise a body (1202) configured to be gripped or held by a hand of a user and one or more projections. For example, the suture control may comprise a first, longer, elongate portion (1204) that may be inserted into a handle, and a second, shorter, elongate portion (1206) that may be coupled to the suture. The first portion (1204) may be longer than the second portion (1206) such that when the first portion is inserted into a side opening in the handle (for example, the side opening (1114) depicted in FIG. 11A), the second portion (1206) does not interfere or otherwise prevent the first portion (1204) from engaging the release assembly. Additionally, the first portion (1204) may comprise a diameter that is smaller than the diameter of the side opening, such that the first portion (1204) may be advanced through the side opening to engage the release assembly. In other variations, the suture control (1200) may comprise a single projection or elongate portion that may both couple to the suture to release the suture from the snare loop assembly and/or tighten the suture, and be inserted into a side opening in the handle to engage with a release assembly (e.g., to release the shuttle and unlock the lock). The suture control (1200) may also couple to a distal end surface of the handle (e.g., through insertion of the one or more projections through openings in the distal end surface), as depicted in FIG. 11A. Additionally, while the suture control (1200) is depicted with cylindrical projections, the one or more projections may have any suitable cross-sectional shape, for example, oval, square, rectangular, hexagonal, and the like.

Figure 13B:
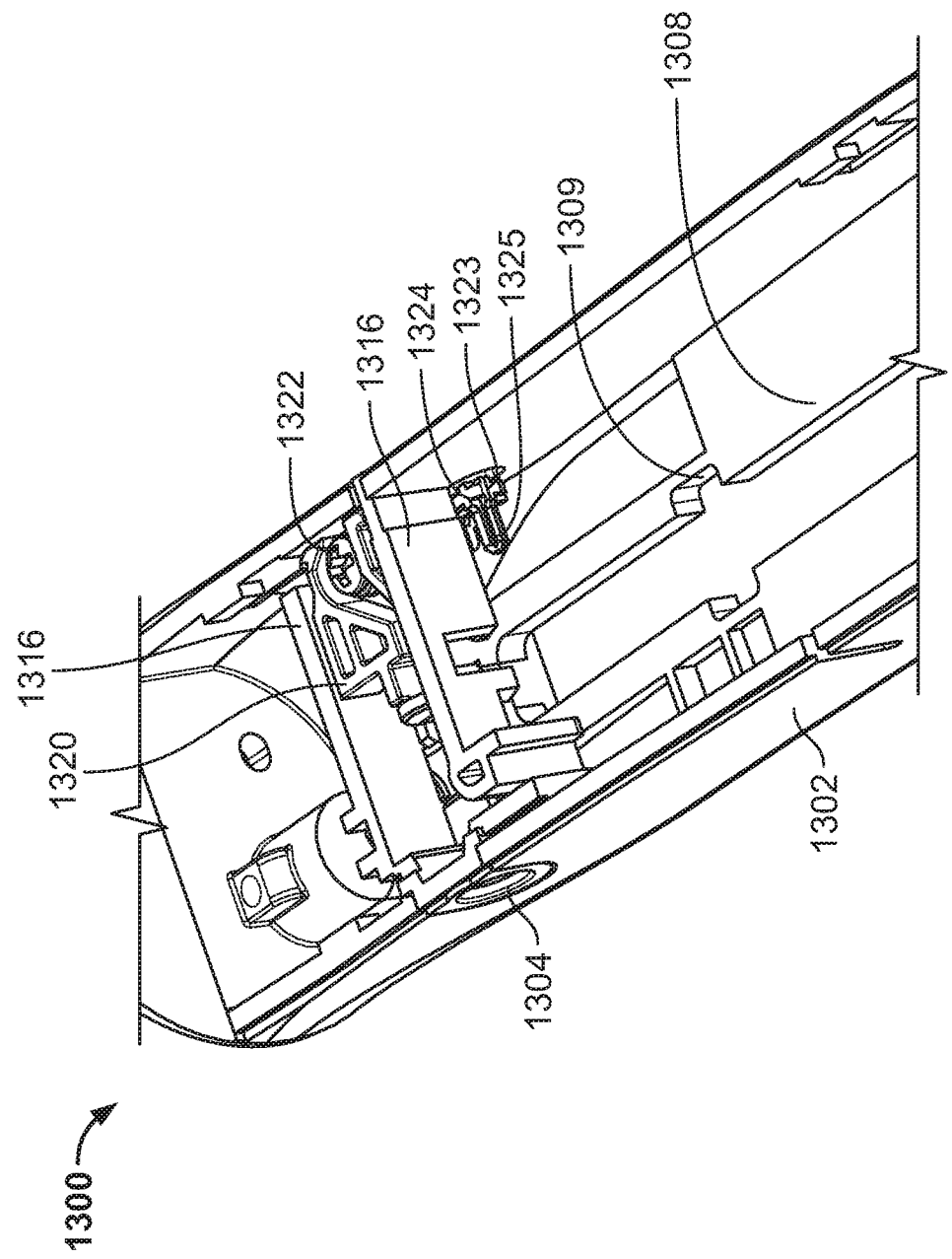

FIGS. 13A-13B are cross-sectional perspective views of a variation of a handle assembly (1300) of a closure device. A bottom cover of the handle (1302) is not shown in FIGS. 13A-13B in order to illustrate an underside of the inner portion of the handle assembly (1300), such as the underside of the track (1308) and the lock (1310). The handle (1302) may comprise an opening (1304) to guide at least a portion of a suture control (not shown) into the handle (1302) to engage with a release assembly (1320). As described above with respect to FIGS. 11A-11D, movement of the snare control along the track (1308), for example, a second portion of the track, may be limited by the lock (1310) when the lock is coupled to the handle and positioned on or within the track (1308). The handle (1302) may further comprise a release assembly housing (1316) and a release assembly housing track (1318) which define the path of movement for the release assembly (1320) and guide the release assembly (1320) along a linear path laterally toward an opposite side of the handle when a portion of the suture control engages with the release assembly (1320).

As shown in FIG. 13A, the lock (1310) may comprise an end plate (1312) at a proximal end thereof and a lock engagement portion (1314). The lock engagement portion (1314) may comprise an opening configured to receive at least a portion of a release engagement portion. Insertion of at least a portion of the suture control into the opening (1304) may unlock the lock (1310) from the track (1308) by disengaging the lock engagement portion (1314) from a portion of the release assembly (1320) (e.g., the release engagement portion). Insertion of at least a portion of the suture control into the opening (1304) may also pull the lock wire proximally, which may retract the lock wire from the lock wire lumen in the shuttle and release the shuttle from the elongate body. The unlocked lock (1310) may be manually removed from the track (1308), which may clear the second portion of the track so that the snare control may move along a second portion of the track (1308). The end plate (1312) may comprise an L-shaped structure that may be configured to couple to a notch or channel (1309) in the track (1308).

The release assembly (1320) may comprise a release engagement portion (1324) configured to releasably couple to the lock engagement portion (1314) of the lock (1310). When the release engagement portion (1324) is coupled with the lock engagement portion (1314), movement of the snare control may be limited, as the lock may block or otherwise prevent the snare control from moving along or through the second portion of the track. Thus, when the release engagement portion (1324) is coupled with the lock engagement portion (1314), the snare and shuttle may not be fully retracted into a lumen of the tip and/or the elongate body.

In some variations, the release engagement portion (1324) may comprise a base (1323) and a protrusion (1325) that extends therefrom, and the protrusion (1325) may be configured (e.g., sized and shaped) to fit within an opening in the lock engagement portion (1314). In some variations, the protrusion (1325) may comprise a circular cross-sectional shape, and a diameter of the protrusion (1325) may be less than the length/width/diameter of the base (1323), however, the length or height of the protrusion (1325) may be greater than a height of the base (1323). The base (1323) may have any suitable cross-sectional shape, for example, square, rectangular, circle, oval, and the like. In other variations, the release engagement portion (1324) may comprise an elongate member comprising a circular cross-sectional shape without a discrete or discernable base. The diameter of the elongate member may be constant along the longitudinal axis of the elongate member (e.g., from a proximal to a distal end of the elongate member). In these variations, the elongate member and/or the entire engagement portion (1324) may be configured to fit within an opening of the lock engagement portion (1314). In some variations, the protrusion (1325) and/or the entire release engagement portion (1324) may have a non-circular cross-sectional shape, for example, square, rectangular, oval, hexagonal, octagonal, or the like. In some embodiments, the release engagement portion (1324) may comprise one or more notches, grooves, and/or indentations on an external surface thereof (e.g., along a length and/or around a circumference thereof), which may in some instances assist with establishing or maintaining contact between the release engagement portion (1324) and the lock engagement portion (1314) of the lock (1310). In variations comprising a base and a protrusion, the notches, grooves, and/or indentations may be on the on the protrusion (1325) and optionally on the base (1323).

The release assembly (1320) may also comprise a lock wire engagement portion (1322) (e.g., a post around which the lock wire may be wound, a screw, or the like), which may couple a proximal end of the lock wire to the release assembly (1320). As described above, the distal end of the lock wire may be disposed within lock wire lumens in the shuttle and the tip or elongate body, which may releasably couple the shuttle to the elongate body.

FIG. 13A illustrates the release assembly (1320) prior to advancement of at least a portion of a suture control through the opening (1304) in the handle (1302). Thus, the lock (1310) in FIG. 13A is engaged and a user is prevented from retracting the snare control through the second portion of the tract to retract the snare and shuttle into a lumen of the device. When the lock is engaged, the stopper of the lock (1310) may be coupled to the track (1308) through the coupling of the lock engagement portion (1314) of the lock (1310) and the release engagement portion (1324) of the handle (1302). In this configuration, the end plate (1312) may also be coupled to the notch (1309) in the track (1308).

FIG. 13B illustrates the handle assembly (1300) after the suture control has been advanced through the opening (1304) and has engaged the release assembly (1320) to release the lock wire and the lock (the lock has been removed for clarity). In particular, the release assembly (1320) has been guided to a second end (opposite a first end adjacent to the opening (1304)) of the releasable assembly housing track (1318) within the releasable assembly housing (1316) to uncouple the release engagement portion (1324) from the lock engagement portion (1314) of the lock (1310). Accordingly, the lock (1310) may be removed from the track (1308) to thereby allow movement of the snare control along a second portion of the track (1308). The movement of the release assembly (1320) along the release assembly housing (1316) also draws in the lock wire to release the shuttle from the elongate body at a distal end of the closure device. Thus, in some variations, movement of the snare control may be limited by the lock until the suture is released, the suture control is decoupled (e.g., cut) from the suture, and at least a portion of the suture control is advanced through the opening to engage (e.g., push, move in a direction transverse to the longitudinal axis of the handle) the release assembly. Accordingly, in this way, premature retraction of a snare loop and the shuttle (e.g., prior to release of the suture loop from the snare loop assembly and/or prior to release of the shuttle from the elongate body) may be prevented. While it may be useful in some variations to prevent release and retraction of the shuttle prior to release of the suture loop from the snare loop assembly, the suture loop need not be deployed from the snare loop assembly prior to release and retraction of the shuttle in all instances.

Figure 14A:
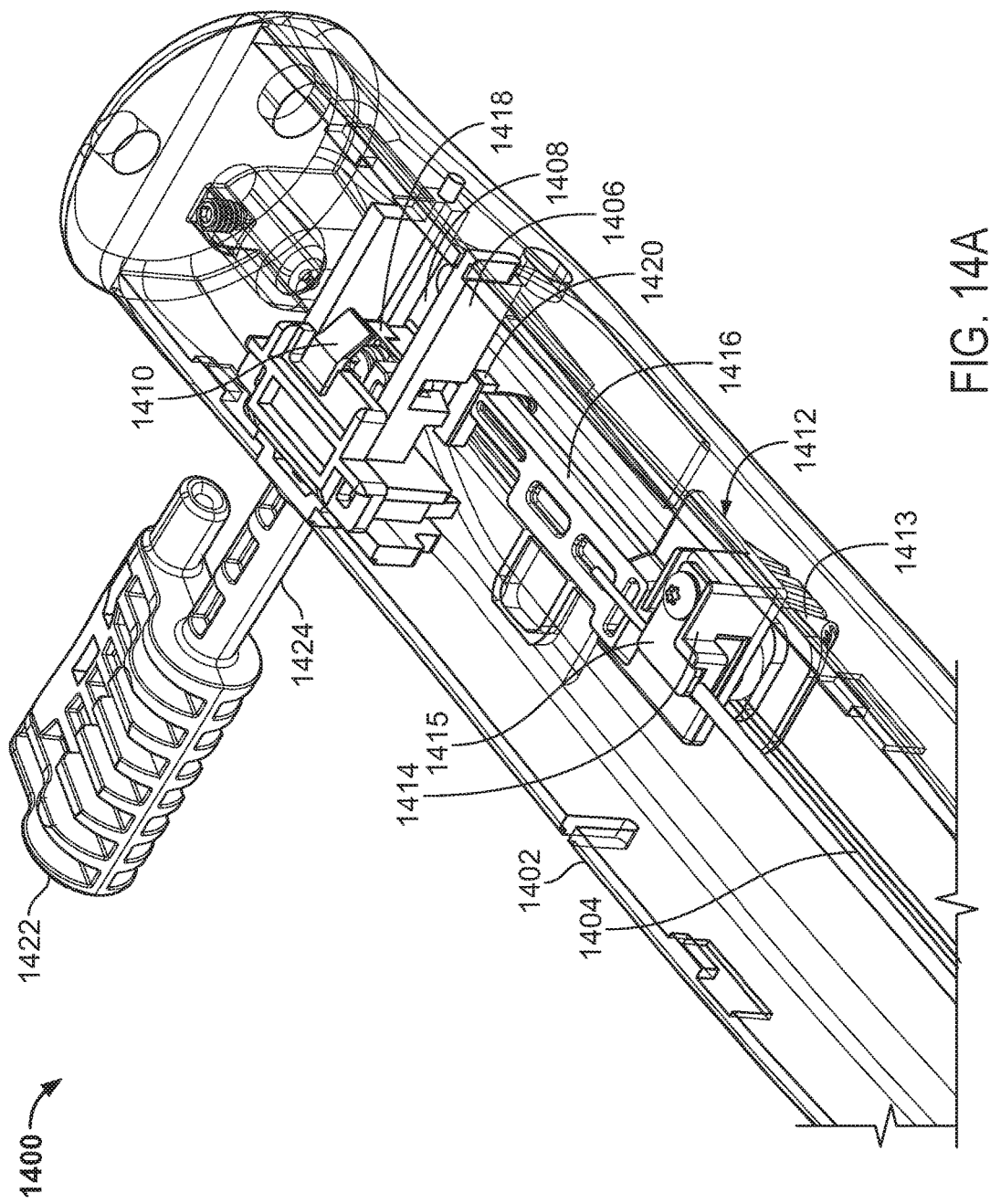
FIGS. 14A and 14C are cross-sectional perspective views of another variation of a handle assembly of a closure device.
Figure 14B:
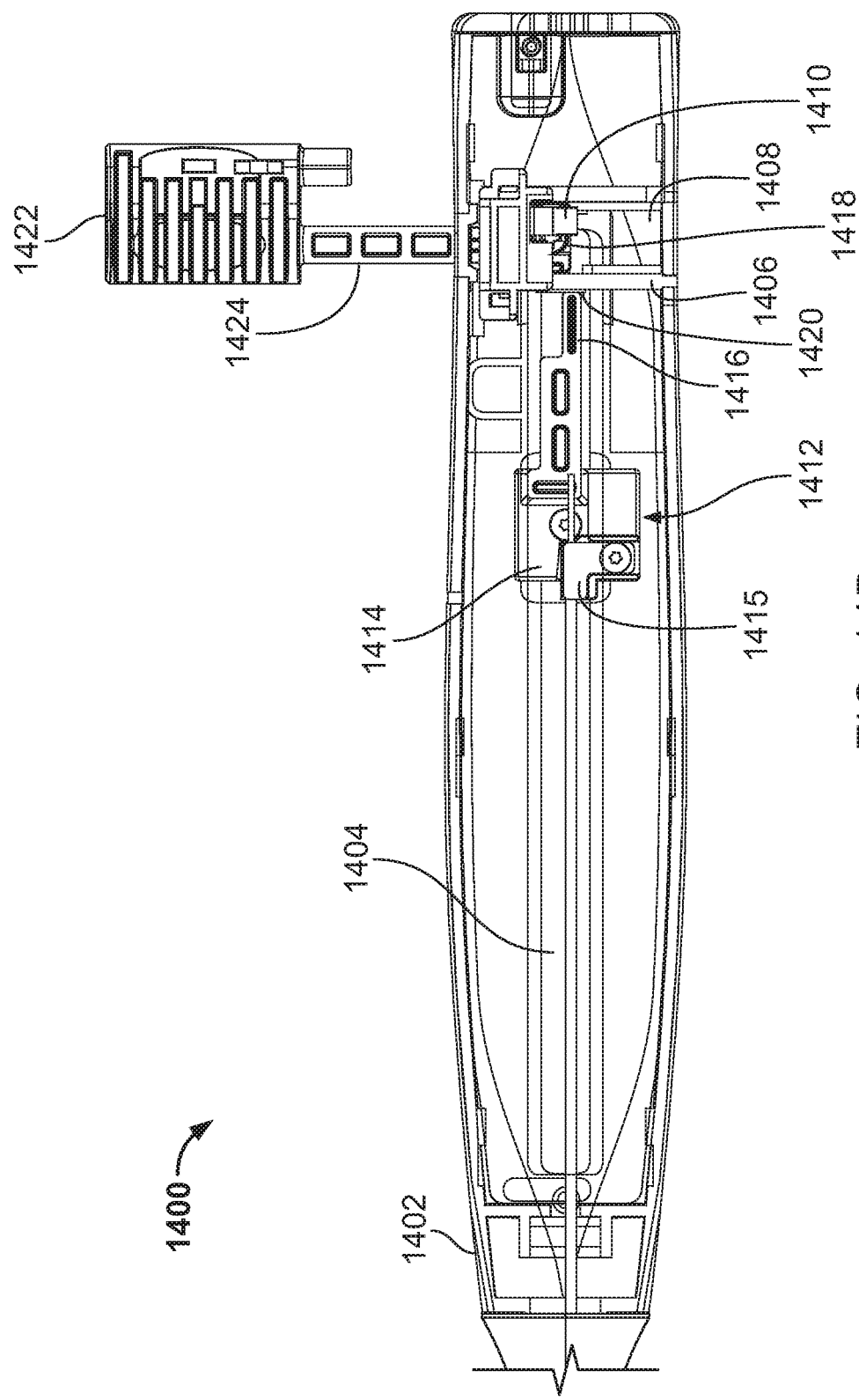
FIG. 14B is a cross-sectional side view of the handle assembly shown in FIG. 14A.
Figure 14C:
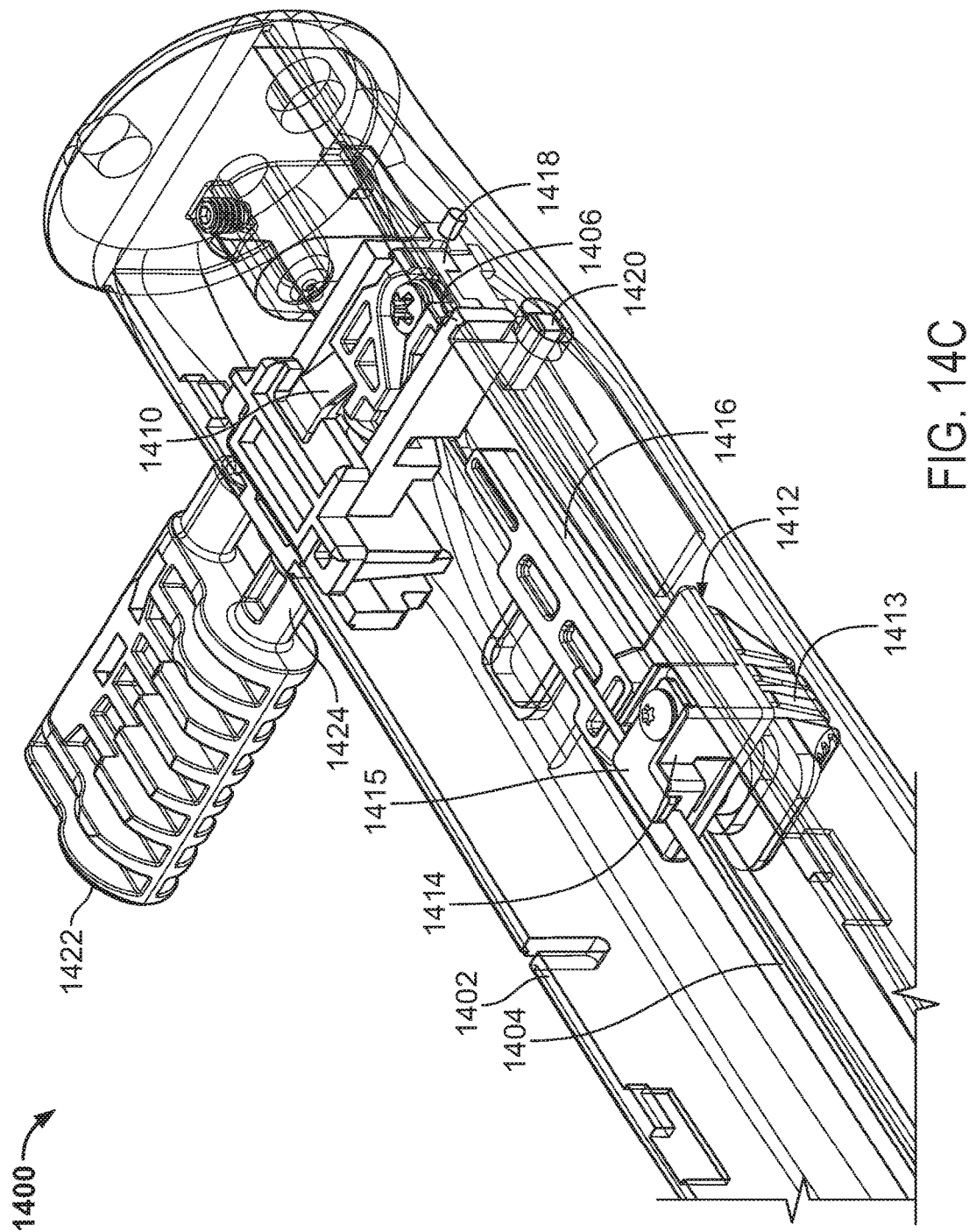

FIGS. 14A and 14C are cross-sectional perspective views of another variation of a handle assembly (1400) of a closure device. In this variations, in place of the lock (1310) shown in FIG. 13A, the snare control (1412) may comprise a limiter (1416) configured to limit movement of the snare control along the track (1404) until a suture control (1422) is inserted into the handle (e.g., via a side opening). FIG. 14B is a cross-sectional side view of the handle assembly shown in FIG. 14A. A bottom cover of the handle (1402) is not shown in FIGS. 14A, 14B, and 14C in order to illustrate an underside of the inner portion of the handle assembly (1400), such as the underside of the track (1404) and snare control (1412).

The handle (1402) may comprise an opening (not shown) to enable and guide a suture control (1422) to engage with a release assembly (1418) within the handle (1402). The handle (1402) may further comprise a release assembly housing (1406) to guide movement of the release assembly (1418) along a release assembly housing track (1408) while the suture control (1422) engages the release assembly (1418). The snare control (1412) may comprise a slider (1413), a track engagement portion (1414) coupled to the slider (1413) via a spring and slideably coupling the slider (1413) to the track (1404), a snare coupler (1415) (e.g., a bracket or the like) coupling a proximal end of the snare to the snare track engagement portion (1414) of the snare control (1412), and a limiter (1416) coupled to or formed integrally with a proximal portion of the snare track engagement portion (1414) and configured to limit movement of the snare control along the track (1404). The slider (1413) may be configured to be advanced and retracted by a hand of the user (e.g., a thumb) when the device is in use.

Figure 15A:
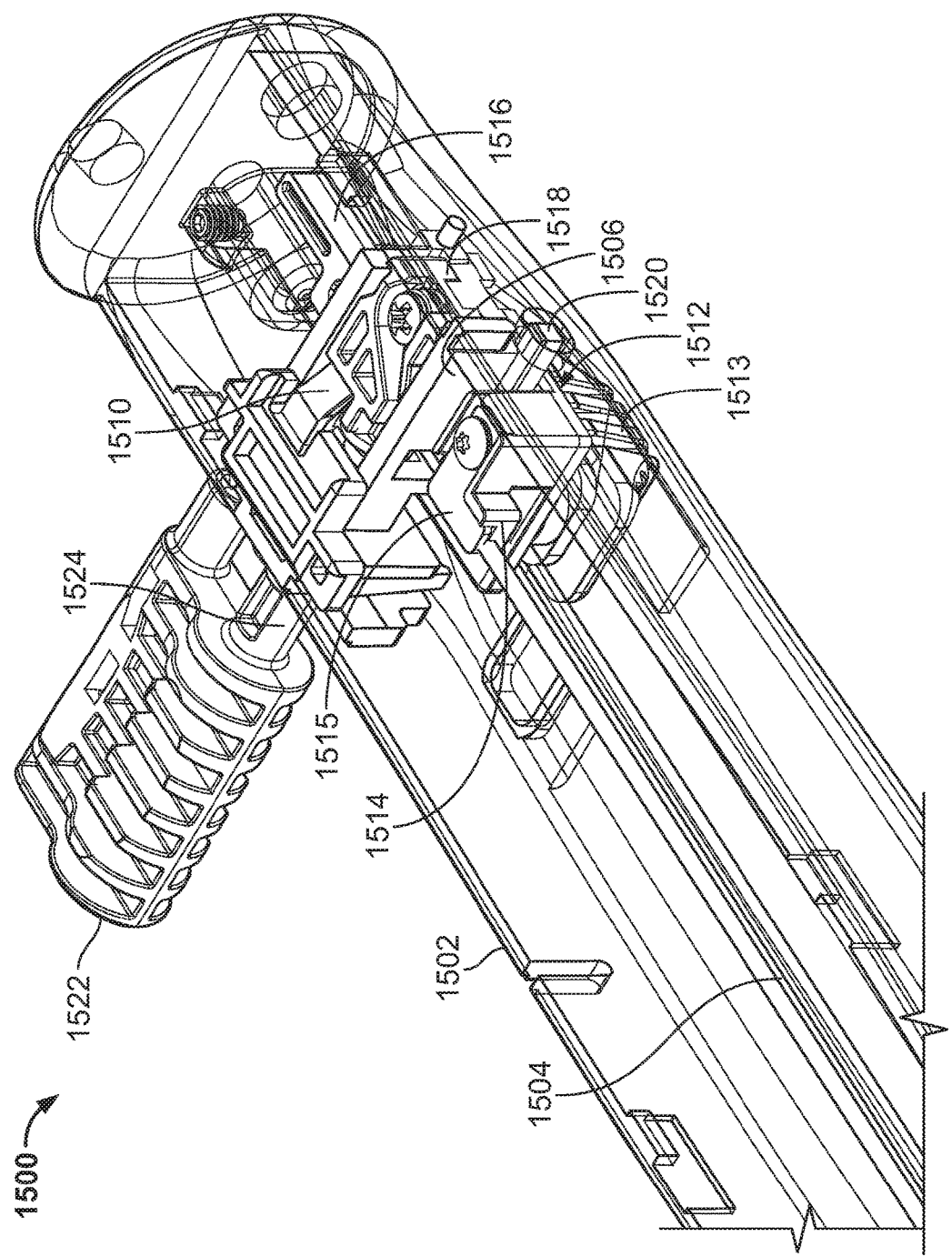
FIG. 15A is a cross-sectional perspective view of yet another variation of a handle assembly of a closure device.

The limiter (1416) may extend along a length of the handle (e.g., along a longitudinal axis thereof) sufficient to provide retraction of the snare and shuttle into the elongate body through movement of the snare control (1412) along the track (1404). The limiter (1416) may be provided on a non-overlapping parallel plane with respect to the release assembly (1418) so as to allow the limiter (1416) to travel over the release assembly (1418) (and the release assembly housing (1406) when the slider (1512) is facing upward toward a user (under the release assembly in the configuration shown) when disengaged from the release assembly (1418), as shown in FIG. 15A. The release assembly (1418) may be configured to release the shuttle from the elongate body and allow movement of the snare control (1412) along the track.

The suture control (1422) may be configured to tighten the suture loop and may comprise a proximal portion. The proximal portion may be configured to engage the release assembly (1418) through an opening in the handle and may comprise a projection (1424). When the projection (1424) engages the release assembly (1418), the limiter (1416) may be disengaged from the release assembly (1418). For instance, the release assembly (1418) may comprise an engagement portion (1420) and the suture control (1422) may be configured to engage the release assembly (1418) to disengage the limiter (1416) from the release assembly (1418), as shown in FIG. 14C. In particular, the engagement portion (1420) may disengage from the limiter (1416) to allow movement of the snare control (1412) along the track (1404). In some variations, disengaging the limiter (1416) may comprise moving the engagement portion (1420) for example, in a direction transverse to a longitudinal axis of the handle (1402), from a first location in which it blocks or otherwise prevents proximal movement of the limiter (1416) to a second location in which it no longer blocks or otherwise prevents proximal movement of the limiter (1416). In this variation, the engagement portion (1420) may serve as a physical stop or barrier. Thus, engaging the release assembly (1418) with at least a portion of the suture control (1422) may move the engagement portion (1420) out of a pathway of the limiter (1416) such that the limiter (1416) may move to a location proximal of the engagement portion (1420). In the variation shown in FIG. 14C, the engagement portion (1420) is disengaged from the limiter (1416) and may be positioned in another opening in the handle (1402).

The suture control (1422) configured to engage the release assembly (1418) may release the shuttle from the elongate body. In some variations, the suture control (1422) may simultaneously disengage the engagement portion (1420) of the release assembly (1418) from the limiter (1416) and release the shuttle from the elongate body.

The handle (1402) may further comprise a flexible latch (1410) configured to allow movement of the release assembly (1418) during insertion of the suture control (1422) into the handle (1402), and configured to limit movement of the release assembly after engagement of the suture control (1422) to the release assembly (1418). As shown in FIG. 14A, as the suture control (1422) is inserted into the handle (1402), the flexible latch (1410) may engage the release assembly (1418) and bend enough to allow the release assembly (1418) to be pushed to an end of the release assembly housing track (1408). However, as shown in FIG. 14C, upon completed insertion of the projection (1424) into the opening, the flexible latch (1410) may return to its original position and engage with a first side surface (i.e., a surface closest to the opening in the handle through which the suture control (1422) is inserted) of the release assembly (1418) in such a manner as to prevent the release assembly (1418) from reverse movement along the release assembly housing track (1408) towards the opening.

Figure 15B:
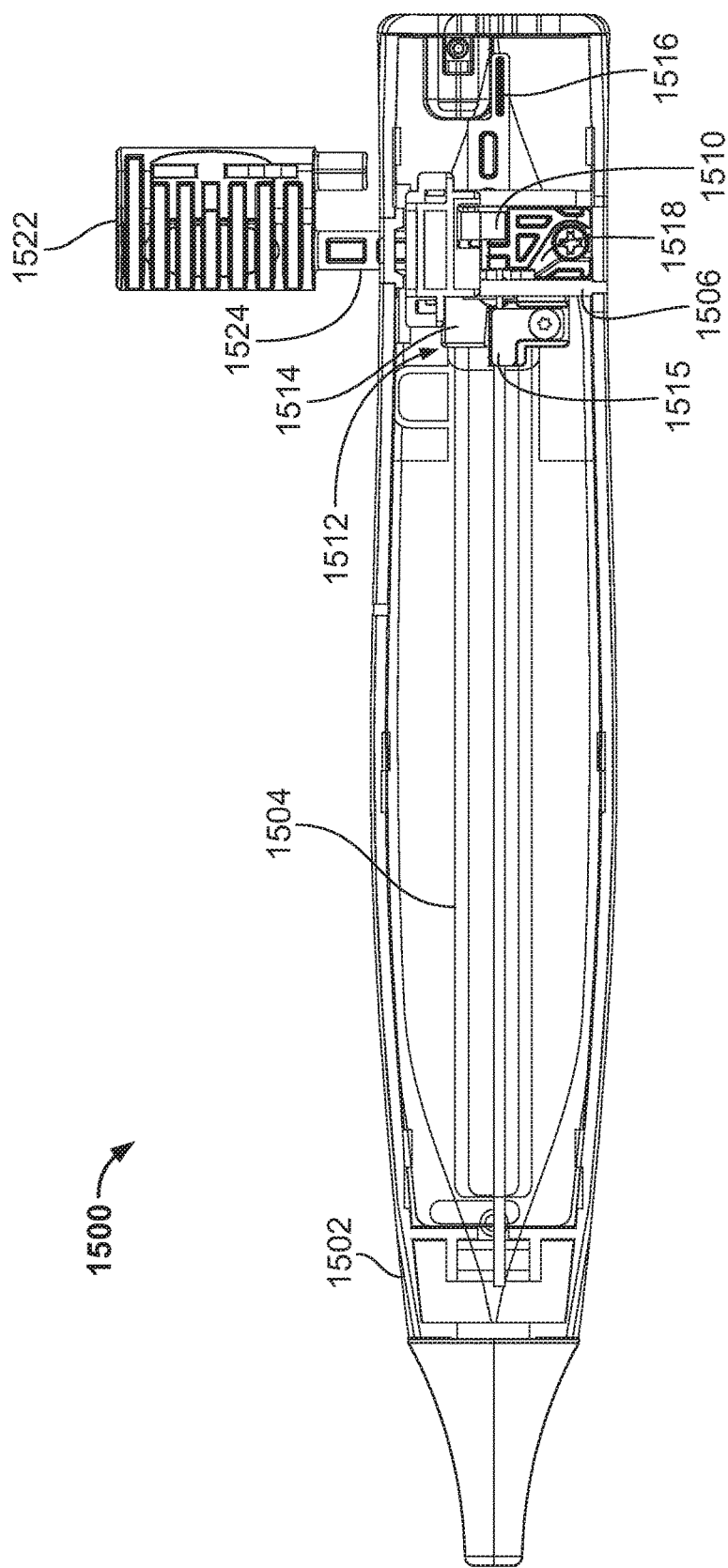
FIG. 15B is a cross-sectional side view of the handle assembly shown in FIG. 15A.

FIG. 15A is a cross-sectional perspective view of a variation of a handle assembly (1500) of a closure device. FIG. 15B is a cross-sectional side view of the handle assembly shown in FIG. 15A. FIGS. 15A-15B illustrate the movement of the snare control (1512) to an end of the track (1504) after engagement of the suture control (1522) disengages the release assembly (1518) from the limiter (1516) of the snare control (1512). The suture control (1522) need not remain in the handle (1502) once inserted, and is provided in FIGS. 15A-15B merely for illustrative purposes.

The snare control (1512) may comprise a slider (1513) or other element configured to interface with a user, a track engagement portion (1514) slideably coupling the snare control (1512) to the track (1504), a snare coupler (1515), and a limiter (1516). The suture control (1522) may comprise a projection (1524) insertable into an opening (not shown) of the handle (1502), which may engage with the release assembly (1518). The handle (1502) may comprise a release assembly housing (1506) that may guide the release assembly (1518) along a housing track (not shown) as the suture control (1522) is inserted into the housing (1502) via the opening. An engagement portion (1520) is shown disengaged from the limiter (1516) to allow movement of the snare control (1512) along the full length of the track (1504). Additionally, the handle (1502) may also comprise a latch (1510) similar to the latch (1410) described above with respect to FIGS. 14A-14C.

II. Methods

The closure devices described here may be useful for closing tissue, for example, the left atrial appendage. The closure devices may access the left atrial appendage using percutaneous or surgical techniques (e.g., median sternotomy, mini sternotomy, thoracotomy, thoracoscopy). One or more guides having alignment members may be advanced to the left atrial appendage. These guides may be any suitable guide, such as those described in U.S. Pat. No. 8,771,297, entitled "Devices, Systems, and Methods for Closing the Left Atrial Appendage" and filed on Mar. 25, 2008, which is incorporated by reference herein in its entirety. For example, first and second guides having alignment members may be used to guide the procedure. The alignment members may be any suitable alignment members (e.g., interconnecting elements, one or more vacuum members, radiopaque or echogenic markers, members that are configured to produce an audible response, magnets, and the like). In some variations, the alignment members may be magnets located at the distal ends of the guides. These guides may be used for guiding additional tools and/or devices (e.g., the closure device) to the left atrial appendage.

For example, in some variations, a first guide may be advanced into the left atrial appendage, while the second guide may be advanced into the pericardial space adjacent to the left atrial appendage. Either of these guides may be advanced under any of a variety of visualization techniques, such as fluoroscopic visualization, ultrasound visualization, or some combination thereof. Once the first and second guide members have been advanced to the left atrial appendage, one or more positioning and/or stabilizing elements (e.g., balloons or other expandable structures) may be advanced over or in conjunction with the first guide (e.g., it may be coupled to or be part of the first guide) and into the left atrial appendage. Similarly, a closure device may be advanced over the second guide to the exterior of the left atrial appendage. It should be appreciated that the closure device may be any of the closure devices described above.

When placed in the left atrial appendage, the positioning element may be used to help position the snare loop of the closure device. In some variations, an expandable structure may be inflated or otherwise expanded in or near the opening of the left atrial appendage and the snare loop may be closed around the left atrial appendage distal to the expandable structure. In other variations, the expandable member may be expanded inside of the left atrial appendage. In these variations, the expandable member may help position the closure device near the base of the left atrial appendage.

While the expandable member is in an expanded state, the snare loop may be opened and may be placed around a portion of the left atrial appendage. Once placed around the left atrial appendage, the snare loop may be closed around the left atrial appendage.

A distal end of an elongate body may be advanced into the body toward a target tissue (e.g., the left atrial appendage). During advancement, the snare loop assembly may be in a closed configuration to help prevent the snare loop assembly from snagging or catching on tissue or other obstructions. Once the distal end of the elongate body has reached a location at or near the target tissue, the snare loop assembly may be opened to a deployed configuration. The snare loop assembly may then be advanced, moved, or otherwise manipulated to encircle at least a portion of the target tissue. The snare loop assembly may then be closed around the encircled tissue to close, ligate, or otherwise restrict the target tissue. The snare loop assembly may be re-opened, repositioned, and re-closed as necessary.

In some instances, a suture loop or other restricting device may be tightened and released from the closure device to maintain the target tissue in a closed fashion. To remove the closure device from the body, the snare loop assembly (e.g., the snare and optionally a retention member) may again be opened to release the target tissue (the suture loop or other restricting device may remain in place) such that the snare loop assembly and the elongate body may be withdrawn. The snare loop assembly may be released for retraction into the elongate body. In variations where the closure device comprises a retraction device or mechanism, the retraction device or mechanism may be used to release the snare and shuttle from the elongate body and retract the snare and shuttle into the elongate body.

In some variations using the devices described here, the methods may comprise fully retracting the snare and shuttle into the elongate body such that no portion, or just a small portion, of the snare and the shuttle remain exposed outside the elongate body. The methods described herein may ensure the release of the suture loop from the snare and retraction of the snare and shuttle from the tip in a manner that prevents an operator from prematurely retracting the snare and shuttle prior to releasing the shuttle from the tip. FIGS. 16A-16G and 17A-17G may more clearly demonstrate these concepts. In FIGS. 16A-16G, a shuttle is released and retracted before tightening a suture loop. In FIGS. 17A-17G, a shuttle is released and retracted after tightening a suture loop.

FIG. 16A is a flowchart (1600) for one variation of a tissue closing process using the devices described herein. FIGS. 16B-16G are perspective views of a snare loop assembly and handle corresponding to the various steps in FIG. 16A. The flowchart (1600) begins with advancement of a closure device towards target tissue (1602). Once advanced to a desired position, a snare loop assembly may be closed around the target tissue (1604), as illustrated in FIGS. 16B and 16C. FIG. 16B illustrates an elongate body (1620) comprising a tip (1622), and a snare loop assembly (1624) comprising a shuttle (1626) positioned within a shuttle recess of the tip (1622). While the snare loop assembly (1624) is depicted without a suture loop and a retention member, the snare loop assembly may comprise both a suture loop and a retention member. The snare loop assembly (1624) is illustrated in the closed position, and the position of the snare loop assembly (and the size of the aperture formed by the snare loop assembly) may be modified by user operation of the handle (1628) shown in FIG. 16C. The snare control (1630) may slide along a track, but may be prevented from initiating retraction of the snare loop assembly (1624) and the shuttle (1626) into the elongate body (1620) and/or tip (1622) by a lock (1632) as depicted (and described in more detail with respect to FIGS. 11A-11D and 13A-13B), or a limiter as described in more detail with respect to FIGS. 14A-14B and 15A-15B. The snare loop assembly (1624) may be opened and closed as necessary to ensure that the target tissue is properly ligated. The handle (1628) may further comprise a suture control (1634) for tightening a suture loop, releasing the lock (1632) from the track, and/or releasing the shuttle (1626).

After the snare loop assembly (1624) is determined to be positioned properly relative to the target tissue and is closed around the target tissue, the suture loop (not depicted) may be released (1606) from the snare loop assembly (1624). A user may pull the suture control (1634) out from a base of a handle (1628) in order to release the suture loop from the snare loop assembly (1624). As least a portion of the suture control (1634) may then be inserted into an opening (e.g., a side opening) in the handle (1628) to engage the release assembly within the handle (1628), release (1608) the shuttle (1626) from the elongate body (1620), and unlock the lock (1632). FIGS. 16D and 16E depict the shuttle released from the shuttle recess of the tip (1622) of the elongate body (1620), and the lock (1632) unlocked and removed from the track. The shuttle (1626) and the portion of the snare loop assembly (1624) remaining outside of the elongate body (1620) may then be partially or fully retracted into the tip (1622) and the elongate body (1620).

In the illustrative variation of FIG. 16E, the shuttle (1626) may be released from the elongate body (1620) by removing the suture control (1634) from the handle (1628) and inserting a portion of the suture control (1634) into an opening in the handle in order to engage the inserted portion of the suture control (1634) with a release assembly (not shown) provided within the handle (1628). For example, as the suture control (1634) engages with or otherwise moves the release assembly, a lock wire coupling the shuttle (1626) to the tip (1622) may retract, which may release the shuttle (1626) from the tip (1622) of the elongate body (1620). The engagement of the suture control (1634) with the release assembly may, in some variations, further simultaneously release/unlock the lock (1632) or a limiter. Removal of the lock (1632) or disengagement of a limiter may allow the snare control (1630) to move proximally further along a track of the handle (1628). Movement of the snare control (1630) proximally to an end of the track may retract the snare loop (e.g., the portion of the snare and retention member that remain outside of the elongate body) and the shuttle into the lumen.

Next, FIGS. 16F and 16G illustrate retraction (1610) of the shuttle (1626) into the elongate body (1620) such as into a lumen (1636) of the tip (1622) and/or a corresponding lumen in the elongate body (1620). For example, in variations comprising a tip (1622), retraction of the shuttle (1626) may result in a portion of the snare loop becoming positioned within a lumen of the elongate body and a portion of the snare loop becoming positioned within a lumen of the tip (1622), or may result in the entirety of the snare loop becoming positioned within a lumen of the elongate body (1620). It should be appreciated that after the shuttle is released, the snare loop may no longer have a loop configuration. After retraction, the shuttle may be positioned within a lumen of the tip (1622), within a lumen of the elongate body (1620), partially within the lumens of both the tip (1622) and the elongate body (1620), or partially within the lumen of the tip (1622) and partially extending from a distal end of the device. In variations in which a tip is not used, retraction of the shuttle (1626) may result in the snare loop and the shuttle becoming positioned within a lumen of the elongate body. Retraction of the snare loop assembly (1624) and the shuttle (1626) into the tip (1622) and/or elongate body (1620) may be controlled by sliding the snare control (1630) along an end portion (second portion) of the track previously covered by the lock (1632) or previously blocked by the limiter. FIG. 16G shows the snare control (1630) at the end portion of the track (e.g., at a proximal end of the track) to fully retract the shuttle (1626) and snare loop assembly (1624) into the elongate body (1620) and tip (1622), and FIG. 16F depicts the snare loop and the shuttle fully retracted into the lumen (1636) of the tip (1622) and/or a corresponding lumen in the elongate body (1620).

Once the shuttle and snare are retracted into the elongate body, the suture loop may be tightened, or further tightened, around the target tissue (1612) using, for example, any of the tensioning devices described in U.S. patent application Ser. No. 13/490,919, entitled "Tissue Ligation Devices and Tensioning Devices Therefor" and filed on Jun. 7, 2012, the contents of which are incorporated by reference herein in their entirety. Finally, the closure device may be withdrawn from the body (1614). As illustrated in FIGS. 16A-16G, the snare loop assembly (1624) and the shuttle (1626) may not be retracted until the shuttle (1626) is released from the tip (1622). In this manner, premature retraction is prevented, thereby improving operability and safety of the closure device.

FIG. 17A is a flowchart (1700) for another variation of a tissue closing process. FIGS. 17B-17G are perspective views of a snare loop assembly and a handle corresponding to the various steps in FIG. 17A. The flowchart (1700) begins with advancement of a closure device towards target tissue (1702). Once advanced to a desired position, a snare loop assembly may be closed around the target tissue (1704).

FIG. 17B illustrates an elongate body (1720) comprising a tip (1722), and a snare loop assembly (1724) comprising a shuttle (1726) positioned within a shuttle recess of the tip (1722). The snare loop assembly (1724) is illustrated in the open position, and may be modified by user operation of the handle (1728) shown in FIG. 17C. In this configuration, the snare control (1730) may slide along the track, but is prevented from initiating a retraction operation of the snare loop assembly (1724) and shuttle (1726) by a lock (1732). A limiter as described with respect to FIGS. 14A-14B and 15A-15B may alternatively be coupled to the snare control (1730) to prevent premature retraction of the snare loop assembly. The snare loop assembly (1724) may be opened and closed as necessary to ensure that the target tissue is properly ligated. The handle (1728) may further comprise a suture control (1734) for tightening a suture loop.

After the snare loop assembly (1724) is determined to be positioned properly, the suture loop may be released (1706) from the snare loop assembly (1724). A user may pull the suture control (1734) out from a base of a handle (1728) in order to release the suture loop from the snare loop assembly (1724). The closed snare loop assembly (1724) may then be opened (1708), as shown in FIG. 17B. After opening the snare loop assembly (1708), the suture loop may be tightened (1710) around the target tissue. Then, the shuttle (1726) may be released (1712) from the elongate body (1720), as illustrated in FIGS. 17D and 17E. The release of the shuttle (1726) from the shuttle recess of the tip (1722) is shown in FIG. 17D and allows retraction of the snare loop assembly (1724) and the shuttle (1726) into the tip (1722) and the elongate body (1720).

In the illustrative variation of FIG. 17E, the shuttle (1726) may be released from the elongate body (1720) by removing the suture control (1734) from the handle (1728) and inserting the suture control (1734) into an opening in the handle to contact a release assembly (not shown) provided within the handle (1728). For example, the suture control (1734)

may engage with the release assembly, which may retract a lock wire to release the shuttle (1726) from the elongate body (1720), as described above. The engagement of the suture control (1734) with the release assembly may, in some variations, further simultaneously release/unlock the lock (1732). The lock (1632) may then be removed from the track to allow the snare control (1730) to be moved further proximally along the track of the handle (1728).

Next, FIGS. 17F and 17G illustrate retraction (1714) of the shuttle (1726) into the elongate body (1720) such as into a lumen (1736) of the tip (1722) and a corresponding lumen in the elongate body (1720). The snare loop assembly (1724) and the shuttle may be retracted (1714) into the tip (1722) and the elongate body (1720) by sliding or otherwise moving the snare control (1730) proximally along an end portion (second portion) of the track previously covered by the lock (1732). FIG. 17G shows the snare control (1730) at the end portion (e.g., a proximal end) of the track to fully retract the shuttle (1726) and snare loop assembly (1724) into the elongate body (1720).

Finally, the closure device may be withdrawn from the body (1716). As illustrated in FIGS. 17A-17G, the snare loop assembly (1724) and the shuttle (1726) may not be retracted until the shuttle (1726) is released from the tip (1722). In this manner, premature retraction may be prevented, thereby improving operability and safety of the closure device.

III. Systems

Described here are systems for closing tissue, for example, a left atrial appendage. In general, the systems may comprise any of the closure devices described herein, together with one or more additional components. For example, the system may comprise a guide device comprising a lumen therethrough. The lumen may be sized and configured to receive an elongate body of a closure device described here. In some embodiments, the system may comprise a first guide wire having a size and length adapted for accessing the left atrial appendage through the vasculature and comprising an alignment member, a second guide wire having a size and a length adapted for accessing the pericardial space from a subthoracic region and comprising an alignment member, and a closure device. The alignment member may be any suitable alignment member. For example, the alignment member may comprise radiopaque or echogenic markers, members configured to produce an audible response, one or more interconnecting members, one or more vacuum members, or magnets. The systems may further comprise instructions for use.

Although the foregoing implementations has, for the purposes of clarity and understanding, been described in some detail by of illustration and example, it will be apparent that certain changes and modifications may be practiced, and are intended to fall within the scope of the appended claims. Additionally, it should be understood that the components and characteristics of the devices described herein may be used in any combination. The description of certain elements or characteristics with respect to a specific figure are not intended to be limiting or nor should they be interpreted to suggest that the element cannot be used in combination with any of the other described elements.

We claim:

1. A method of closing a target tissue comprising:
   advancing a device towards the target tissue, wherein the device comprises an elongate body, a snare loop assembly comprising a snare and a suture loop, and a shuttle connected to the snare and releasably coupled to the elongate body;
   closing the snare loop assembly around the target tissue;
   releasing the suture loop from the snare loop assembly;
   releasing the shuttle from the elongate body;
   retracting the shuttle into a lumen of the elongate body; and
   tightening the suture loop around the target tissue.

2. The method of claim 1, wherein retracting the shuttle is performed prior to tightening the suture loop.

3. The method of claim 1, wherein tightening the suture loop is performed prior to releasing the shuttle from the elongate body.

4. The method of claim 3, further comprising opening the closed snare loop assembly, wherein tightening the suture loop is performed after opening the closed snare loop assembly.

5. The method of claim 4, wherein opening the closed snare loop assembly further comprises bending the distal end portion of the snare freely away from the elongate body.

6. The method of claim 1, wherein a maximum shuttle diameter is less than a diameter of the lumen of the elongate body.

7. The method of claim 1, wherein the suture loop is tightened via a suture control.

8. The method of claim 7, wherein the device further comprises a handle coupled to the elongate body, and wherein retracting the shuttle comprises inserting a portion of the suture control through an opening in the handle, engaging a release assembly with the inserted portion of the suture control, and disengaging a lock from the release assembly.

9. The method of claim 8, wherein the handle comprises a snare control and a track with a first portion and a second portion, and wherein retracting the shuttle further comprises removing the lock from a second portion of the track and moving the snare control along the second portion of the track.

10. The method of claim 1, wherein the device further comprises a handle attached to the elongate body, wherein the handle comprises a track, a snare control coupled to the track, and a lock configured to limit movement of the snare control along the track, and wherein the handle further comprises a release assembly configured to release the shuttle from the elongate body and allow movement of the snare control along the track.

11. The method of claim 10, wherein the track comprises a first portion and a second portion, and the lock limits movement of the snare control along the second portion of the track.

12. The method of claim 1, wherein retracting the shuttle is performed after tightening the suture loop.

13. A device for closing a target tissue comprising:
   an elongate body;
   a snare loop assembly comprising a snare and a suture loop releasably coupled to the snare, and the snare loop assembly extending at least partially from the elongate body;
   a shuttle releasably coupled to the elongate body, wherein the shuttle is connected to a distal portion of the snare; and
   a handle attached to the elongate body, the handle comprising a track and a snare control coupled to the track, wherein the handle further comprises a lock configured to limit movement of the snare control along the track and a release assembly configured to release the shuttle from the elongate body and allow movement of the snare control along the track.

14. The device of claim 13 further comprising a suture control configured to tighten the suture loop.

15. The device of claim 14, wherein the suture control comprises a proximal portion configured to engage the release assembly through an opening in the handle and disengage the lock from the release assembly.

16. The device of claim 13, wherein the lock comprises a stopper extending along a length of the track.

17. The device of claim 16, wherein the lock further comprises a lock engagement portion comprising an opening, wherein the opening is releasably coupled to the release assembly.

18. The device of claim 17, wherein the release engagement portion extends from a bottom surface of the stopper.

19. The device of claim 17, wherein the release assembly comprises a release engagement portion, and wherein the lock engagement portion is releasably coupled to the release engagement portion.

20. The device of claim 19, wherein the release engagement portion comprises a base and a protrusion, and wherein the protrusion is configured to fit within the opening of the lock to releasably couple the lock engagement portion and the release engagement portion.

21. The device of claim 17, wherein the lock further comprises an end plate.

* * * * *